United States Patent
Lapidot et al.

(10) Patent No.: US 6,642,365 B1
(45) Date of Patent: Nov. 4, 2003

(54) ANTI-(RETRO)VIRAL CONJUGATES OF SACCHARIDES AND ACETAMIDINO OR GUANIDINO COMPOUNDS

(75) Inventors: Aviva Lapidot, Rehovot (IL); Alexander Litovchick, Boston, MA (US); Artem G. Evdokimov, Fredrick, MD (US)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/869,437

(22) PCT Filed: Dec. 28, 1999

(86) PCT No.: PCT/IL99/00704

§ 371 (c)(1), (2), (4) Date: Jun. 28, 2001

(87) PCT Pub. No.: WO00/39139

PCT Pub. Date: Jul. 6, 2000

(51) Int. Cl.[7] ............................. C07H 1/00; A61K 31/70
(52) U.S. Cl. .................... 536/13.7; 536/13.6; 536/13.2; 536/16.6; 514/25; 514/39; 514/41
(58) Field of Search ............................... 536/13.7, 13.6, 536/13.2, 16.6; 514/25, 39, 41

(56) References Cited

U.S. PATENT DOCUMENTS 5,593,835 A * 1/1997 Rando et al. ................... 435/6

FOREIGN PATENT DOCUMENTS

| EP | 312 222 | * | 4/1989 |
| WO | WO 95/00177 | * | 1/1995 |

OTHER PUBLICATIONS

Luedtke et al. "Guanidinoglycosides: A novel family of RNA ligands." J. Am. Chem. Soc. 122, pp. 12035–12036, 2000.*
Park et al. "Rapid combinatorial synthesis of aminoglycoside antibiotic mimetics:." J. Am. Chem. Soc. 118, pp. 10150–10155 1996.*
Baisch et al. Bioorganic & Medicinal Chemistry, vol. 6, No. 7, pp. 749–762, 1996.*
Litovchick A et al. "Arginine–aminoglycoside conjugates that bind to HIV transactivation responsive element RNA in vitro" Febs Lett. (FEBLAL, 00145793); 1999; vol. 445 (1); pp. 73–79, XP000891778.

(List continued on next page.)

Primary Examiner—James O. Wilson
Assistant Examiner—Devesh Khare
(74) Attorney, Agent, or Firm—Browdy and Neimark

(57) ABSTRACT

Conjugates of a saccharide and an acetamidino- or guanidino-compound, of the formula:

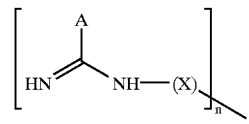

wherein A is $CH_3$ or $NH_2$; X is a linear or branched $C_1$–$C_8$ alkyl chain optionally containing hydroxy, amino and/or oxo groups; n is an integer from 1 to 6, and Sac is the residue of a mono-or oligo-saccharide, provided that when A is $NH_2$ and X is -$(CH_2)_3$—$CH(NH_2)$—$C(=O)$-, the monosaccharide residue is not substituted at the position 1, and n is an integer from 2 to 6 when Sac is the residue of an oligosaccharide, are useful as antiviral, particularly as antiretroviral, agents, and can be used either alone or together with other compounds used in AIDS treatment such as AZT and/or protease inhibitors, for the treatment of HIV-infection, AIDS and manifestations of AIDS such as Kaposi sarcoma. Particularly preferred compounds are aminoglycoside-arginine conjugates in which the saccharide is a natural aminoglycoside antibiotic such as kanamycin, gentamycin and neomycin that is conjugated to arginine residues.

23 Claims, 20 Drawing Sheets

OTHER PUBLICATIONS

Wang Y et al. "Specificity of Aminoglycoside Binding to RNA Constructs Derived from the 16S rRNA Decoding Region and the HIV–RRE Activator Region" Biochemistry (Bichaw, 00062960); 1997; vol. 36 (4); pp. 768–779, XP002135230.

Wong C H et al. "A Library Approach to the Discovery of Small Molecules That Recognize RNA: Use of a 1,3–Hydroxyamine Motif as Core" J. Am. Chem. Soc. (JACSAT, 0027863); 1998; vol. 120 (33); pp. 8319–8327, XP000901596.

Miyajima K et al. "Synthesis of Tn, sialyl Tn and HIV–1–derived peptide antigen conjugates having a lipid A analog as an immunoadjuvant for synthetic vaccines" Chem. Pharm. Bull (CPBTAL, 00092363); 1998; vol. 46 (11); pp. 1676–1682, XP000891781.

Huang X et al. "Glycosylation Affects Bothe the Three–Dimensional Structure and Aantibody Binding Properties of the HIV–1IIIB GP120 Peptide RP135" Biochemistry (BICHAW, 00062960); 1997; vol. 36 (36); pp. 10846–10856, XP000891780.

Elofsson M et al. "Preparation of Tn and sialyl Tn building blocks used in Fmoc solid–phase synthesis of glycopeptide fragments from HIV gp120" Tetrahedron (TETRAB, 00404020); 1997; vol. 53 (1); pp. 369–390, XP004105143.

Park W K C et al. "Rapid Combinatorial Synthesis of Amino Glycoside Antibiotic Mimetics: Use of a Polyethylene Glycol–Linked Amine and a Neamine–Derived Aldehyde in Multiple Component Condensation as a Stratedy for the Discovery of New Inhibitors of the HIV RNA Rev Responsive Element" J. Am. Chem. Soc. (JACSAT, 0027863); 1996; vol. 118 (42); pp. 10150–10155, XP000901595.

Huang X et al. "Structural comparison of a 15 residue peptide from the V3 loop of HIV–1IIIb and an O–glycosylated analog" Febs Lett. (FEBLAL, 00145793); 1996; vol. 393 (2,3); pp. 280–286, XP000891779.

Vuljanic T et al. "Piperidine is preferred to morpholine for Fmoc cleavage in solid phase glycopeptide synthesis as exemplified by preparation of glycopeptides related to HIV gp120 and mucins" Tetrahedron (TETRAB, 00404020); 1996; vol. 52 (23); pp. 7983–8000, XP004103905.

Baisch G et al. "Enzymic fucosylation of non–natural trisaccharides with cloned fucosyltransferase VI" Bioorg. Med. Chem. Lett (BMCLE8, 0960894X); 1996; vol. 6(7); pp. 759–762, XP004134950.

Baisch G et al. "Enzymic. Alpha. (2,3)–sialylation of non–natural disaccharides with coned sialytransferase" Bioorg. Med. Chem. Lett. (BMCLE8, 0960894X); 1996; vol. 6 (7); pp. 749–754.

Baisch G et al. "Enzymic galactosylation of non–natural glucosamine acceptors" Bioorg. Med. Chem. Lett. (BMCLE8, 0960894X); 1996; vol. 6 (7); pp. 749–754, XP004134948.

Lapidot A et al. "Tetrahydropyrimidine derivatives inhibit binding of a Tat–like, arginine–containing peptide, to HIV TAR RNA in vitro", pp. 33–38, XP–000940413.

* cited by examiner

Tat + TAR =

+ INHIBITOR = +

TAR + CONJUGATE PEPTIDOMIMETIC =

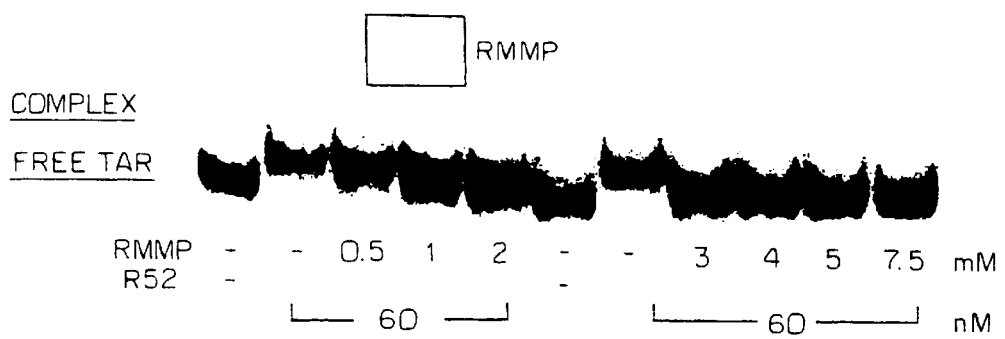
FIG. 3A
FIG. 3B
FIG. 3C
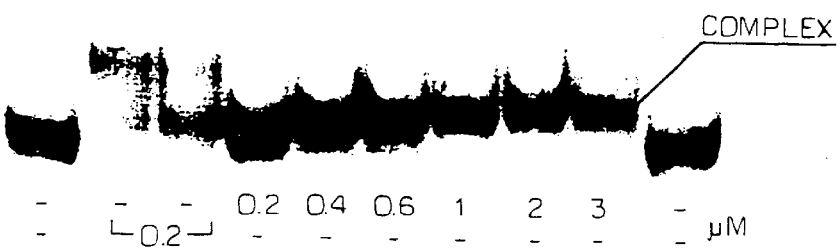
FIG. 3D

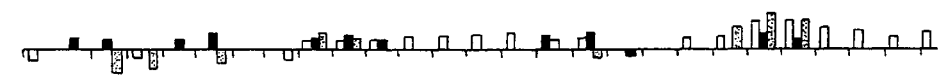
FIG. 5A
R52
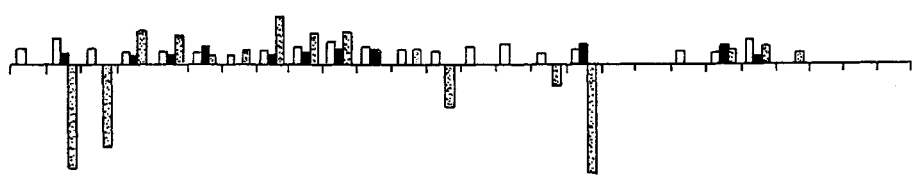
FIG. 5B
R4K
FIG. 5C
R3G
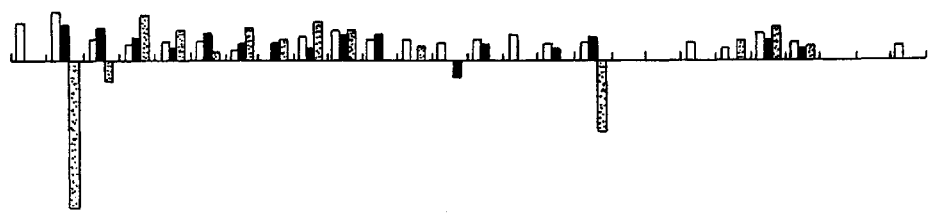
FIG. 5D
GB4K
☐ URANYL
■ LEAD
▨ RNase A

NUCLEOTIDE

☐ AAC
■ AAC(tRNA)

■ PROTECTION SITE NOT INHIBITED BY tRNA

⊙ PROTECTION SITE INHIBITED BY tRNA

⇨ CONFORMATIONAL CHANGES, THAT MAKE THE SITE MORE ACCESSIBLE FOR RNase A CLEAVAGE.

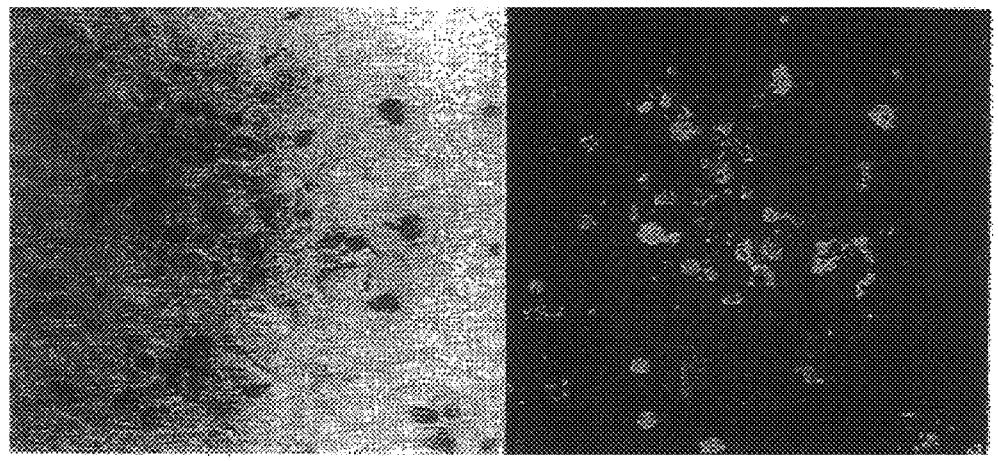
*FIG.11A*  *FIG.11C*
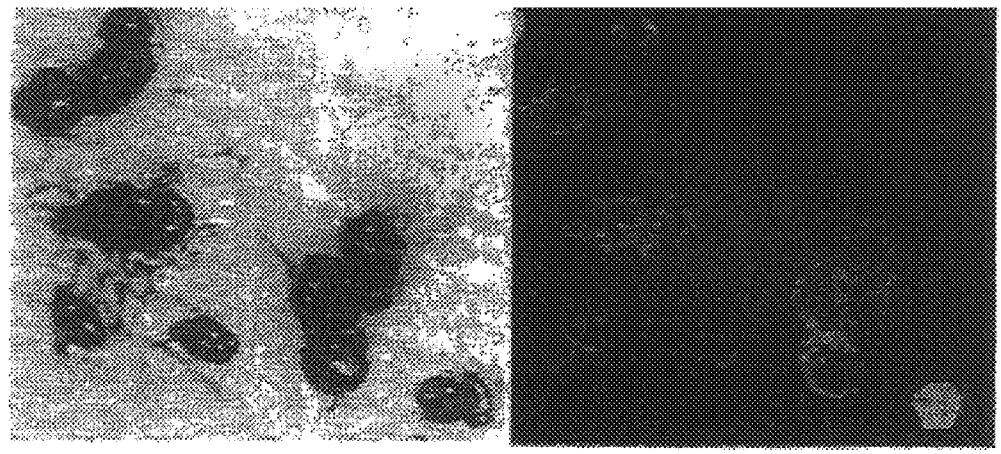
*FIG.11B*  *FIG.11D*

- ■ INFECTED CELLS, INCUBATED WITH R3G
- △ INFECTION IN THE PRESENCE OF R3G, INCUBATION WITHOUT R3G
- ✕ INFECTION IN THE PRESENCE OF R3G AND INCUBATION WITH R3G

- ■ INFECTED CELLS, INCUBATED WITH NeoR
- △ INFECTION IN THE PRESENCE OF NeoR, INCUBATION WITHOUT NeoR
- ✕ INFECTION IN THE PRESENCE OF NeoR AND INCUBATION WITH NeoR

CCR5 (2D7)

CXCR4 (12G5)

CD4 (Leu 3a)

R3G (25μg/ml)

R4K (25μg/ml)

MEAN FLUORESCENCE INTENSITY

ANTI-(RETRO)VIRAL CONJUGATES OF SACCHARIDES AND ACETAMIDINO OR GUANIDINO COMPOUNDS

REFERENCE TO RELATED APPLICATIONS

The present application is the national stage under 35 U.S.C. 371 of international application PCT/IL99/00704, filed Dec. 28, 1999 which designated the United States, and which international application was published under PCT Article 21 (2) in the English language.

FIELD OF THE INVENTION

The present invention relates to antiviral compounds, more particularly to peptidomimetic conjugates of saccharides, such as aminoglycoside antibiotics, with acetamidino and guanidino compounds, and to antiviral, including antiretroviral, pharmaceutical compositions comprising them.

ABBREVIATIONS AND DEFINITION

HIV: human immunodeficiency virus; RT: reverse transcriptase; RNAse: ribonuclease; UC781: a non-nucleoside RT inhibitor; AZT: azidothymidine; KS: Kaposi sarcoma; AIDS: acquired immunodeficiency syndrome; Tat: transactivator of transcription; TAR: trans-activation responsive RNA region; LTR: long terminal repeat; P-TEFb: positive transcription elongation factor b; CDK9: cyclin-dependent kinase; ALX40-4C: D-arginine nonapeptide; CGP64222: peptide peptoid mimetic of Tat basic domain; HeLa: human epithelial cell line derived from cervical cancer; CXCR4: CXC (α-chemotactic cytokines related to interleukin-8, containing C-X-C motif in their sequence, e.g. SDF-1α) chemokine receptor 4; CD4: cluster of differentiation 4 (characteristic receptor of T-helper cells); CCR5: CC (β-chemotactic cytokines, containing CC motif in their sequence) chemokine receptor 5; PBMC: peripheral blood mononuclear cells; T22: octadeca peptide, CXCR4 antagonist; AAC: aminoglycoside-arginine conjugates; R52: Tat-derived model undeca peptide, containing a single arginine moiety at position 52 of native Tat protein, in the strand of lysines; R4K: tetra-argininamido kanamycin A conjugate; R3G: tri-argininamido gentamicin C conjugate; MMP: α-methyl D-mannopyranoside RMMP: mono-argininamido MMP conjugate; R4GC1a: tetra-argininamido gentamicin C1a isomer conjugate; GABA: γ-aminobutyric acid; GB4K: tetra-γ-(N-guanidino) butyramido-kanamycin A conjugate; NeoR: hexa-argininamido neomycin B conjugate; EIAV: equine infectious anemia virus; ED: equine dermal fibroblasts; DMF: dimethyl formamide; DCC: dicyclohexyl carbodiimide; M.p.: melting point; Pd/C: palladium on charcoal catalyst; TFA: trifluoro acetic acid; FABHRMS: fast atom bombardment high resolution mass spectroscopy; HSQC: heteronuclear single-quantum coherence; TOCSY: total correlation spectroscopy; RRE: Rev responsive RNA element; CAT: chloramphenicol acetyl transferase; DTT: dithiotreitol; EDTA: ethylenediamine tetraacetic acid; $CI_{50}$: concentration of compound, that causes 50% inhibition of Tat-TAR interaction; $CE_{50}$: concentration of 50% elution from affinity column; $CD_{50}$: 50% binding concentration, related to $K_d$; $K_d$: dissociation constant; LAN-1: human neuroblastoma cell line; MPC-11: murine plasmocytoma cell line; MT-2, MT-4: human T-lymphoma cell lines, transfected with HTLV-I; HTLV-I, HTLV-II: Human-T-lymphoma virus type I or II; DMEM: Dulbecco modified Eagle's medium; FCS: fetal calf serum; polybrene: hexadimetrine bromide; pfu: plaque forming unit; ELISA: enzyme-linked immuno sorption assay; P4-CCR5 MAGI: human cell line of monocyte/macrophages origin; HUVEC: human umbilical vascular endothelial cells; SUP-T1: human T-cell line; cpe: cytopathic effect; $IC_{50}$: 50% inhibitory concentration; $CC_{50}$: 50% cytotoxic concentration; $EC_{50}$: 50% effective concentration; $TI_{50}$: 50% in vitro therapeutic index (ratio $CC_{50}/EC_{50}$); SDS: sodium dodecyl sulfate; PAGE: polyacrylamide gel-electrophoresis; TLC: thin layer chromatography; HRP: horseradish peroxidase; SDF-1α: stromal cell derived factor 1, subtype α, the natural ligand of CXCR4; IL2: interleukin 2; IgG: immunoglobulin G; mAb: monoclonal antibody; 12G5: anti-CXCR4 mAb; 2D7: anti-CCR5 mAb; Leu3a: anti-CD4 mAb; PE: phycoerythrin; FITC: fluorescein isothiocyanate; RANTES: regulated on activation normal T-cell expressed and secreted chemokine; MPD: methyl pentandiol; SIR: single isomorphus replacement; SIRA: single anomalous replacement; MAD: multiple anomalous diffraction.

BACKGROUND OF THE INVENTION

The transactivation responsive RNA (TAR) region of human immunodeficiency virus (HIV) long terminal repeat (LTR) regulates the viral gene expression via interaction with the HIV transactivator protein, Tat, and thus is an attractive target for drug design strategies (Gait and Karn, 1995). TAR is found at the 5' end of all HIV-1 transcripts. It adopts a hairpin secondary structure consisting of a highly conservative hexanucleotide loop and a three-nucleotide bulge flanked by two double-stranded stems (Calnan et al., 1991 a, b). TAR is a positive enhancer that stimulates the synthesis of productive transcripts. It is unique in terms of eukariotic transcription control because it only functions as an RNA element. The activation by Tat is entirely dependent on the presence of the TAR RNA sequence. Tat activates expression by specific binding to TAR, which increases viral mRNA production several hundred-fold by stimulation of the elongation capacity of RNA polymerase II (Kingsman and Kingsman, 1996). HIV Tat binds the cyclin T subunit of P-TEFb and recruits P-TEFb to the HIV-1 LTR promoter. This process requires binding of Tat to the TAR bulge and of cyclin T to the TAR loop. The cyclin T associated CDK9 kinase then induces phosphorylation of the C-terminal domain of RNA polymerase II, and of other polymerase II-associated proteins, leading to the transition from non-processive to processive transcription (Cullen, 1998).

Binding of Tat protein to TAR is mediated by the nine amino acid region RKKRRQRRR (residues 49–57) of the protein (e.g. Calnan et al., 1991 a, b; Churcher et al., 1993). The nona-arginine peptide ($R_9$) binds to TAR with the same affinity and specificity as the above wild-type Tat peptide, whereas the nona-lysine peptide ($K_9$) binds to TAR non-specifically and with a ten-fold lower affinity. The $R_9$-containing Tat mutant protein gives wild-type trans-activation activity and is 100-fold more active than the $K_9$-containing protein. Insertion of a single arginine moiety at position 52 or 53 (synthetic peptides R52 of the sequence YKKKRKKKKA or R53) restores RNA-binding affinity and specificity of the peptide as well as its trans-activation potency (Calnan et al., 1991 b). Mutagenesis studies on TAR RNA demonstrated that the bulge (U23-C24-U25) and two base pairs at both sides of the bulge (e.g. Cordingley et al,. 1990; Roy et al, 1990; Delling et al., 1992) are important for Tat binding. Full length Tat protein binds TAR with only moderate affinity and specificity in vitro. The first 37 N-terminal amino acids of the Tat protein decrease its affinity to TAR in comparison to the specific recognition Tat (38–72) peptide (Rana and Jeang, 1999). It was shown that human cyclin T1 promotes cooperative binding of Tat protein to TAR RNA in vitro and mediates trans-activation in vivo. Although cyclin T1 does not bind TAR RNA, it may interact with the TAR loop in a ternary complex of cyclin T1-Tat-TAR (Wei et al., 1998).

NMR structures of HIV TAR bound to different ligands, e.g. as peptides that mimic the basic region of Tat, arginine and arginineamide, show that the ligands bind to the TAR RNA major groove (Puglisi et al., 1992, 1993; Aboul-ela et al., 1995, 1996). The bulge structure allows ligands to access the major groove of TAR, which induces folding in the bulge and formation of unusual base-triples (Puglisi et al., 1992, 1993, Aboul-ela et al., 1995, 1996). The TAR RNA hairpin can adopt two major conformations. In the absence of ligands, the bulge nucleotides stack within the RNA stem, severely distorting its helical continuity (Puglisi et al., 1992; Aboul-ela et al., 1996). When either L-arginineamide or the Tat peptide bind to TAR, the bulge nucleotides loop out of the remaining stem, allowing the upper and the lower stem helices to stack coaxially (Puglisi el al., 1992, 1993). The NMR structure of L-arginineamide bound to TAR suggests proximity between the bulge and apical loop across the RNA major groove (Aboul-ela et al., 1995, 1996). The specific interactions between HIV Tat protein and TAR RNA are still unknown but could be modeled as a basic ax-helix of Tat peptide lying in the major groove of TAR (Mujeeb et al., 1996).

Tat-derived basic peptides, as well as the oligocationic peptide and peptoid Tat mimetics bind TAR RNA with high affinity in vitro (e.g . Calnan et al., 1991 a, b; O'Brien et al., 1996; Hamy et al., 1997; Huq et al. 1997, 1999 a). Tat-mimetic compounds ALX40-4C (O'Brien et al., 1996) and CGP64222 (Hamy et al., 1997), that target TAR RNA, demonstrate a pronounced antiviral activity. D-Tat peptide, derived from Tat 37-72 sequence, binds to TAR RNA major groove and interferes with the transcriptional activation by Tat protein in vitro and in HeLa cells (Huq et al., 1999 a).

The functions of Tat protein in viral progeny are not limited to HIV trans-activation event. Tat trans-activates a number of cellular genes and acts as chemokine analogue, while secreted extracellularly (Albini et al., 1998). Tat induces positive chemotaxis of human monocytes and monocyte-derived dendritic cells (Benelli et al, 1998). Extracellular Tat protein was shown to up-regulate the expression of CXCR4 chemokine receptor in primary-resting CD4+ T-cells (Secchiero et al., 1999) as well as CCR5 receptor on monocytes (Weiss et al., 1999), which serve as co-receptors of viral entry for T-tropic and M-tropic HIV strains, respectively (Berger et al., 1999). It was shown, that HIV Tat protein, released by infected cells, differentially induces CXCR4 and CCR5 expression in peripheral blood mononuclear cells (PBMC), and promotes infectivity of both M- and T-tropic HIV-1 strains (Huang et al., 1999). The discovery of chemokine receptors as cofactors involved in the entry of HIV in the host cell has renewed the interest in the early steps of virus replication as a target for therapeutic intervention. A number of compounds have been described to interact with CCR5, the chemokine receptor used by macrophage-tropic (MT, R5) strains of HIV (Simmons et al., 1997). Two other groups have also described newly identified CXCR4 antagonists: ALX40-4C (Doranz et al., 1997) and T22 (Murakami et al., 1997), an octadecapeptide with 8 positive charges or its derivatives (Arakaki et al., 1999).

Another function of Tat protein (in synergism with inflammatory cytokines) is in induction of angiogenesis and the development of Kaposi sarcoma in AIDS patients (Barillari et al., 1999). All the above Tat functions are dependent on the presence of the basic domain in the protein structure. However, Tat has multiple domains, and two of them mediate the cellular and viral effects of extracellular Tat. Peptides, derived from cystein-rich domain and (possibly in combination with) basic domain were found to mimic the effects of a whole Tat protein in HIV-infected cells (Boykins et al., 1999).

Among natural RNA targeting molecules, aminoglycoside antibiotics have interesting properties that make them similar to peptide RNA binders. They are known to bind efficiently to RNA, such as 16S RNA or introns type I (von Ahsen et al. 1992). Neomycin B and tobramycin inhibit HIV Rev-RRE interaction in vitro at concentrations of 1–10 $\mu$M, whereas kanamycin and gentamicin do not display any inhibition at 100 $\mu$M. Recent experiments have demonstrated that among the aminoglycoside antibiotics, neomycin has the greatest inhibitory effect on Tat binding to TAR in vitro in the range of 1–100 $\mu$M. This phenomenon was attributed to the direct association of the aminoglycoside antibiotic with TAR RNA in its lower stem (Wang et al., 1998).

SUMMARY OF THE INVENTION

It has now been found, in accordance with the present invention, that by combining a carbohydrate skeleton, either a mono or an oligosaccharide similar to aminoglycoside antibiotics with side-chains of variable length bearing a guanidine moiety or a chemical group with a similar geometry and/or charge properties resembling peptide side chains, a new class of peptidomimetic TAR RNA binders is obtained that are anti-HIV compounds and suppress viral replication (HIV-1 and EIAV) by inhibiting transactivation by Tat as well as by blocking viral entry to cells through chemokine-receptor-dependent mechanism. These relatively low molecular weight compounds, which mimic the functions of Tat protein basic domain, are the first examples of substances composed of a carbohydrate core conjugated to L-arginine or similar compounds with side chains, bearing guanidino or acetamidino groups that efficiently bind to TAR RNA as well as efficiently inhibit HIV-1 entry to T-cells.

The present invention thus relates to conjugates of saccharides and acetamidino or guanidino compounds of the formula I:

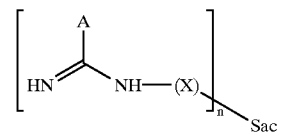

wherein
A is $CH_3$ or $NH_2$, X is a linear or branched $C_1$–$C_8$ alkyl chain optionally containing hydroxy, amino and/or oxo groups; n is an integer from 1 to 6, and Sac is the residue of a mono- or oligo-saccharide.

When A is $CH_3$, the conjugates are acetamidino saccharide conjugates, and when A is $NH_2$, the conjugates are guanidino saccharide conjugates. Sac may be the residue of a monosaccharide, in which case n is 1–5, or of an oligosaccharide, in which case n is 1–6.

Examples of monosaccharide conjugates according to the invention are methyl 6-deoxy-6-(N-acetamidino)-$\alpha$-D-mannopyranoside, methyl 6-deoxy-6-guanidino-$\alpha$-D-mannopyranoside and methyl 6-deoxy-6-(N-L-argininamido)-$\alpha$-D-mannopyranoside (the compounds 11, 10 and 12 herein) of the formulas shown in Scheme 1 herein.

The natural or synthetic oligosaccharides are, for example, an aminoglycoside antibiotic such as, but not limited to, neomycin, kanamycin or gentamicin, or synthetic oligosaccharides. The aminoglycoside-arginine conjugates of the invention will also sometimes be designated herein in the specification as AAC.

The invention further provides pharmaceutical compositions comprising a conjugate of the invention and a pharmaceutically acceptable carrier, particularly for use as antiviral, more particularly as antiretroviral, compositions, alone or together with other anti-AIDS agents such as AZT or protease inhibitors.

BRIEF DESCRIPTION OF THE FIGURES

FIGS. 3A–3D present electrophoretic mobility shifts of the complexes of TAR RNA with conjugates of the invention: (3A) Inhibition of Tat R52 peptide binding to TAR RNA by conjugate RMMP (compound 12) (60 nM of Tat R52, 6 nM TAR); (3B) Binding of conjugate R4K (compound 13) to TAR RNA (12 nM): a ratio of 2:1 R4K to TAR RNA in the complex is suggested; (3C) Binding of triargininamido gentamicin conjugate R3G (compound 14) mixture to TAR RNA (12 nM). Complexes of increasing molecular weight and precipitation of RNA in the wells are observed; (3D) tetraargininamido gentamicin conjugate R4GC$_{1a}$ (compound 15) binding to TAR RNA (20 nM): a ratio of 1:1 of R4GC$_{1a}$ to TAR RNA in the complex is suggested. The concentration of Tat R52 in the control lanes is 200 nM.

FIG. 5 is a summary of the TAR RNA footprinting studies of FIG. 4. The results are derived from densitometry of the gels presented in FIG. 4. Bars represent % of protection calculated for each band compared to "control" (in the absence of binders) in each method. Negative peaks stand for enhancement of cleavage at the nucleotide (mainly by RNase A). Lead acetate results allow accurate assignment of the binding site, RNase A mainly probes secondary structure changes, uranyl nitrate, at our conditions at low pH, probes both binding site and conformational changes.

7B. Band shift of TAR complexes with R52, R4K and R3G in the presence of an excess of yeast tRNA. 100 ng of yeast tRNA per lane do not inhibit the binding of Tat R52, R4K and R3G to TAR RNA. Band shifts suggest one molecule of aminoglycoside-arginine conjugate per one molecule of TAR RNA in the complex. In the presence of 1 μg tRNA per sample, the binding of both R52 and the conjugates was 90% inhibited.

7C. In the presence of 0.5 μg yeast tRNA, the RNase A footprinting of TAR complexes with R52, R4K, R3G and GB4K has similar pattern as seen in FIG. 4. Binding of conjugates to low affinity binding site on TAR is partially suppressed.

7D. Quantitation of band intensities of lane 5 of the gel, presented in FIG. 7C in comparison to lane 5 of the FIG. 4A.

7E. Schematic representation of conjugate binding to TAR RNA in the presence of excess of tRNA.

Figure 8A:
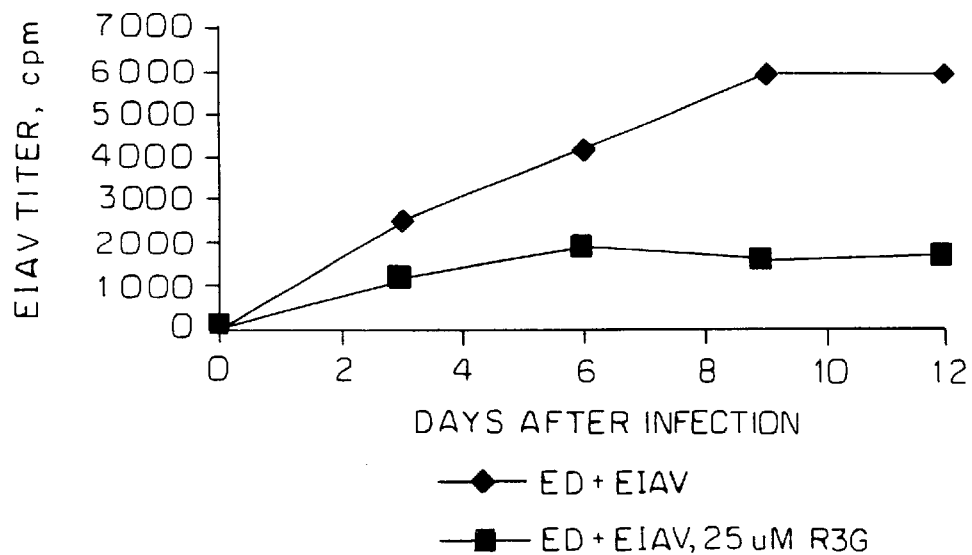
Figure 8B:
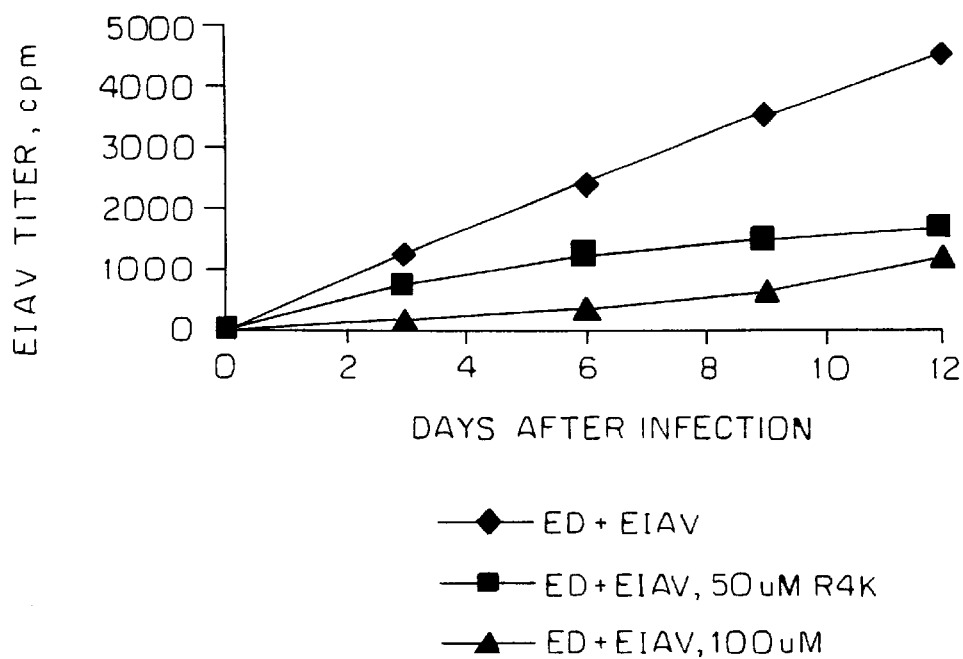

FIGS. 8A–8B show the effect of R3G (8A) and R4K (8B) on equine infectious anemia virus (EIAV) replication in equine dermal (ED) fibroblast cells. The cells were infected with 10 pfu EIAV per cell (superinfection) and were cultured in the medium, supplemented with $^3$H-uridine. R3G and R4K were added to the medium in a range of 12.5 to 100 μM. Viral titer was assayed every 3 days by radioactive uridine incorporation in the RNA of the viral particles. Each data point represents averages of 6 (R3G) and 4 (R4K) experiments (variation within 10%). R3G inhibited the viral growth at 12.5 and 25 μM, and R4K at 50 and 100 μM.

Figures 8C, 8D:
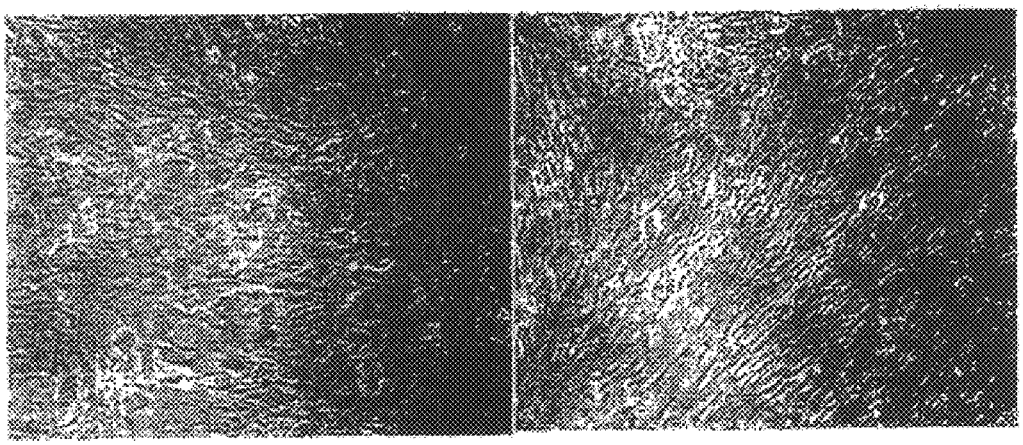

FIGS. 8C–8D depict optical microscopy images of the cytopathic effect (cpe) development in EIAV-infected ED cells in the presence of R3G. The images were taken with Axiovert 100M (Zeiss) microscope using 40x planar objective. C. After 13–15 days, EIAV-infected ED cells started to form syncytia, that indicates the onset of EIAV cpe, D. The cells treated with 25 μM R3G preserved normal fibroblast phenotype at the same day of the infection.

Figure 9A:
Figure 9B:
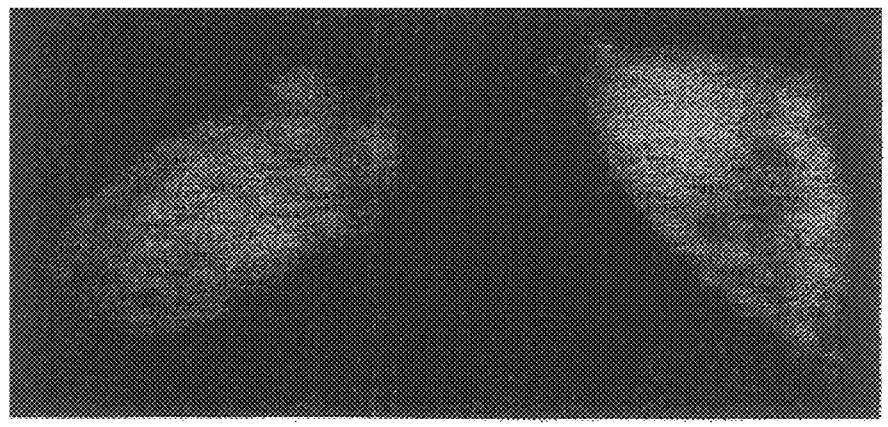

FIGS. 9A–9B show cellular uptake of the aminoglycoside conjugate R4K detected by a fluorescent probe. (9A) Accumulation of fluorescein-labeled conjugate R4K (R4K-fluorescein) probe in rat hippocampal neurons, detected by confocal laser-scanning microscopy. The cells were incubated in the presence of R4K-fluorescein (1 mg/ml) for 2 hours; (9B) Laser scanning allows observation of intracellular distribution of R4K-fluorescein in the neurons. Preferentially intranuclear accumulation of the probe is observed.

Figure 10A:
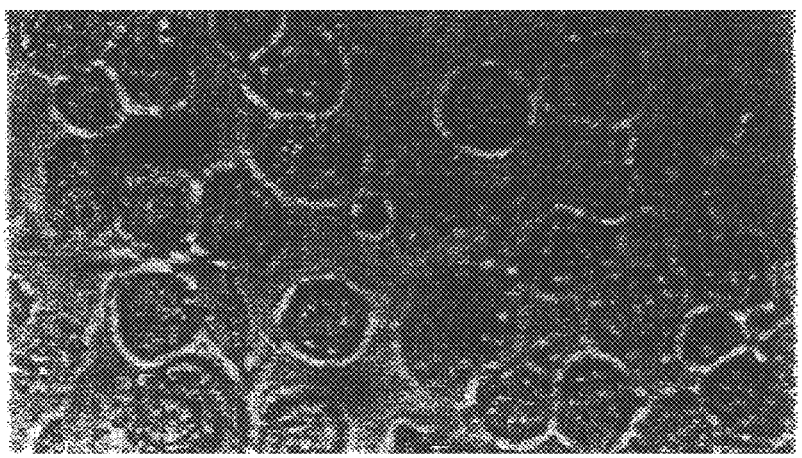
Figure 10B:
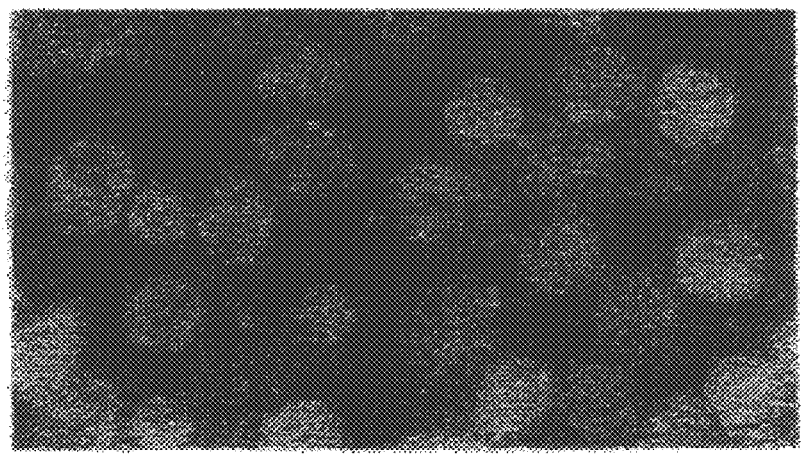
Figure 10C:
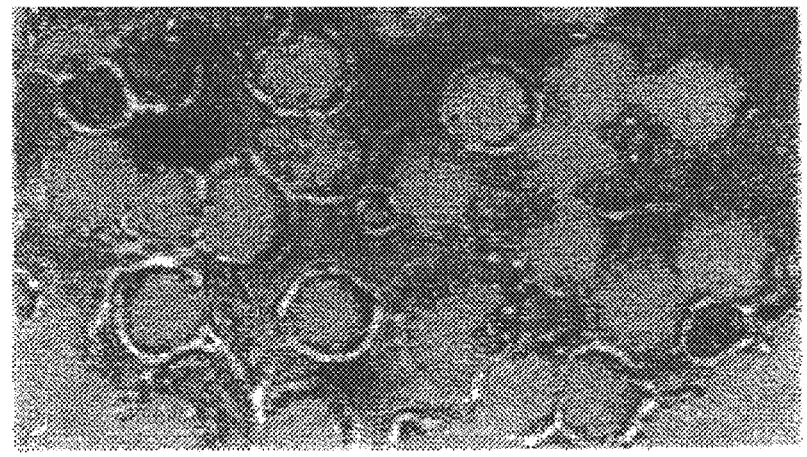

FIGS. 10A–10C show cellular uptake of the aminoglycoside conjugate R4K detected by a fluorescent probe. (10A) Light microscopy of human peripheral blood mononuclear cells (PBMC); (10B) The same field as in FIG. 10A showing accumulation of R4K-FITC in PBMC, detected by confocal laser-scanning fluorescent microscopy. The cells were incubated in the presence of R4K-FITC (1 mg/ml) for 1.5 hours; (10C) Superposition of FIGS. 10A and 10B: fluorescence is highly detectable in the nuclei of the cells.

FIGS. 11A–11D present confocal microscopy images of live EIAV-infected ED cells stained with R3G-FITC. The images were taken with Axiovert 100M (Zeiss) microscope using 63x water immersion objective. (11A) Optical microscopy of EIAV-infected ED cells, on day $16^{th}$. The cells are significantly damaged. (11B) The same fields, confocal fluorescent microscopy at 488 nm excitation. Fluorescent R3G derivative, R3G-FITC, accumulate in the cell nuclei. (11C) and (11D)—same as (11A) and (11B) at higher magnification (digital, 8x).

Figure 12:
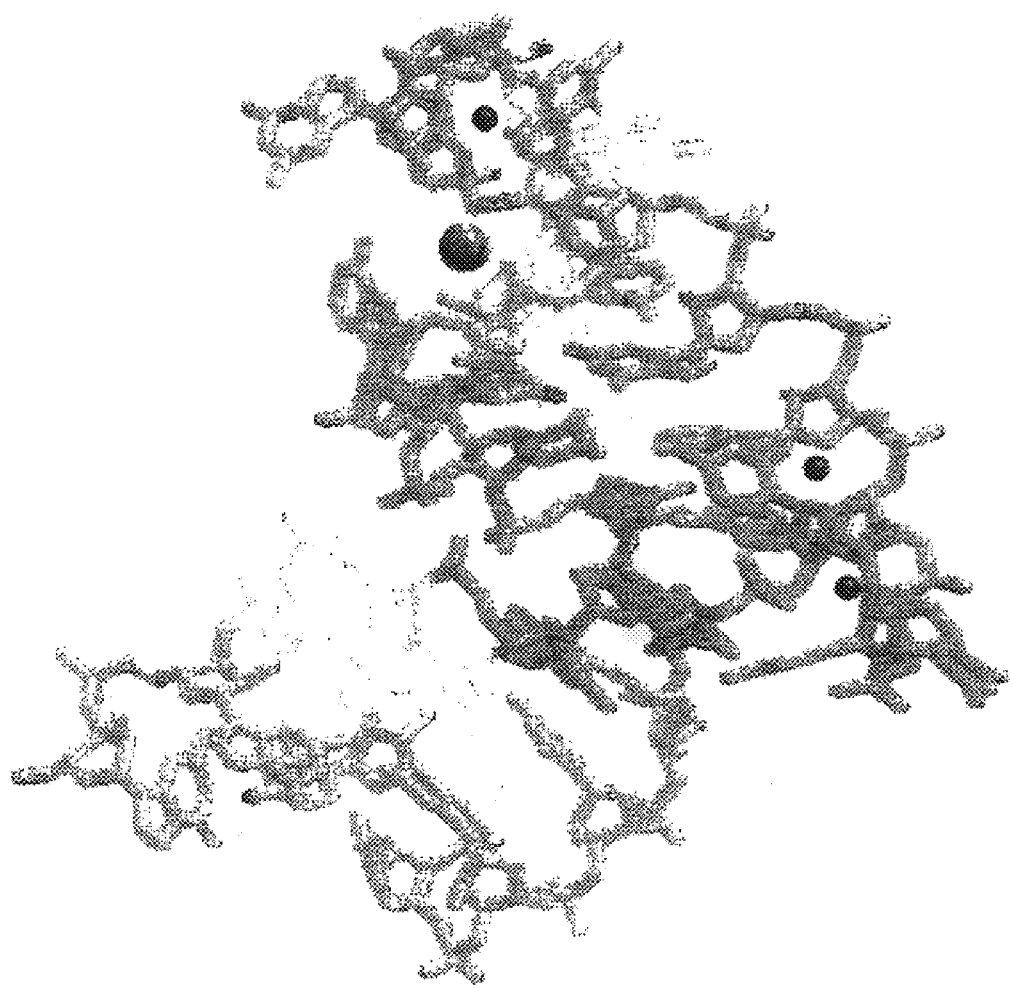

FIG. 12 is a schematic representation of binding sites of an aminoglycoside-arginine conjugate (AAC) of the invention on TAR RNA. The NMR average structure of TAR RNA complex with arginine amide, was obtained from Protein Data Bank, access code 1arj. Only nucleic acid chain is presented. Nucleotides highlighted in pink represent high affinity binding site for AAC and Tat peptide. Binding of AAC to this site is not inhibited by excess of tRNA. Nucleotides highlighted in blue represent low affinity binding site for AAC and aminoglycosides (e.g neomycin B). Binding of AAC to this site is inhibited by 10-fold excess of tRNA. Nucleotides highlighted in yellow represent sites of major conformational changes induced by AAC binding to TAR. These positions are cleaved by RNase A in TAR-AAC complex, but are not cleaved in the absence of AAC. Small green balls represent proposed $Mg^{++}$ and $Ca^{++}$ binding sites. Big yellow ball represents $UO_2^{++}$ binding site.

Figure 13A:
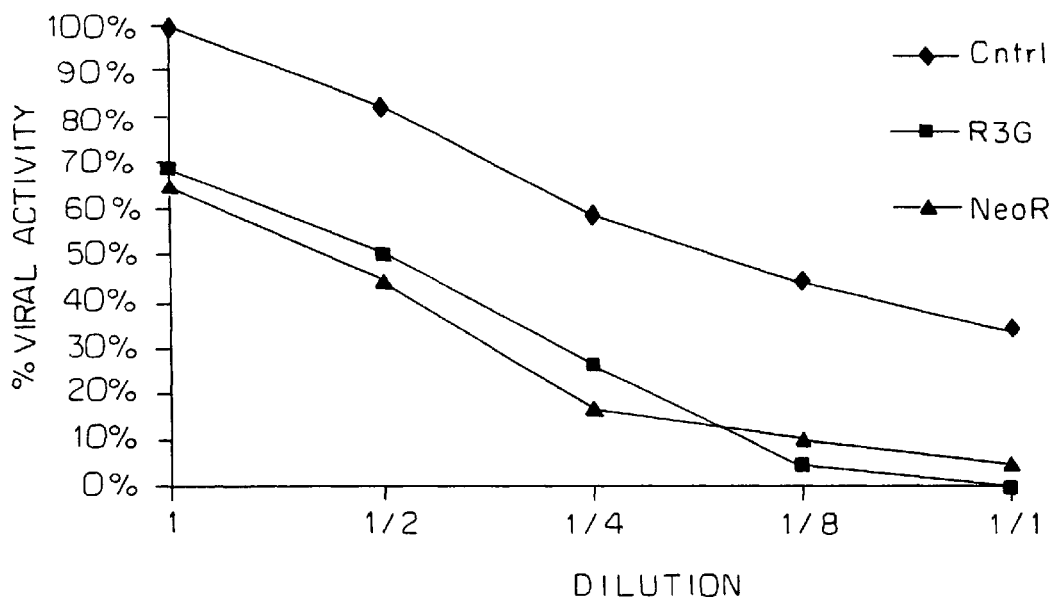
Figure 13B:
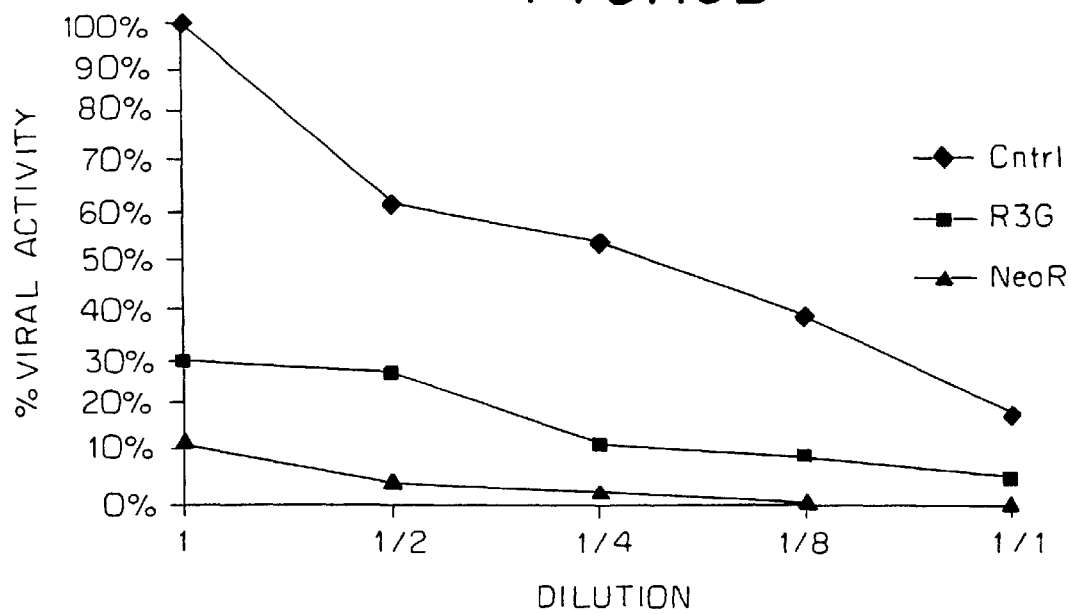

FIGS. 13A–13B present antiviral activity of conjugates R3G and NeoR (compounds 14 and 20, respectively) against different dilutions of HIV-1 2D strain and clade C clinical isolate. Infection of MT2 cells was carried out for 2 hrs with 1:1 to 1:16 dilutions of viral stock, followed by cell wash. Around $5 \times 10^4$ cells were seeded per well in 96-well plate and were incubated for 4 days with 20 μM R3G or 10 μM NeoR, until syncytia were observed. Cell viability was tested by the tetrazolium-based colorimetric method.

Figure 14A:
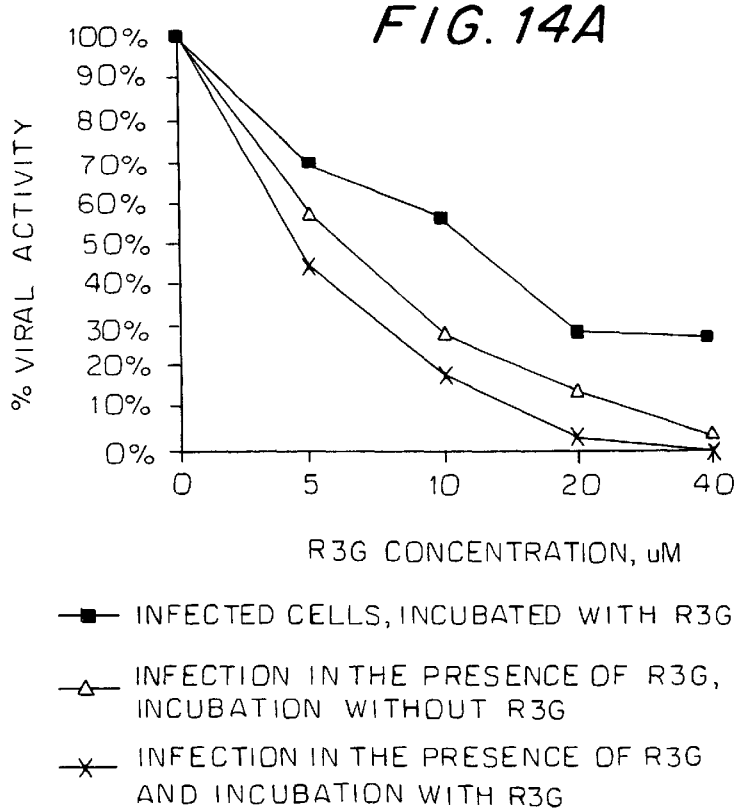
Figure 14B:
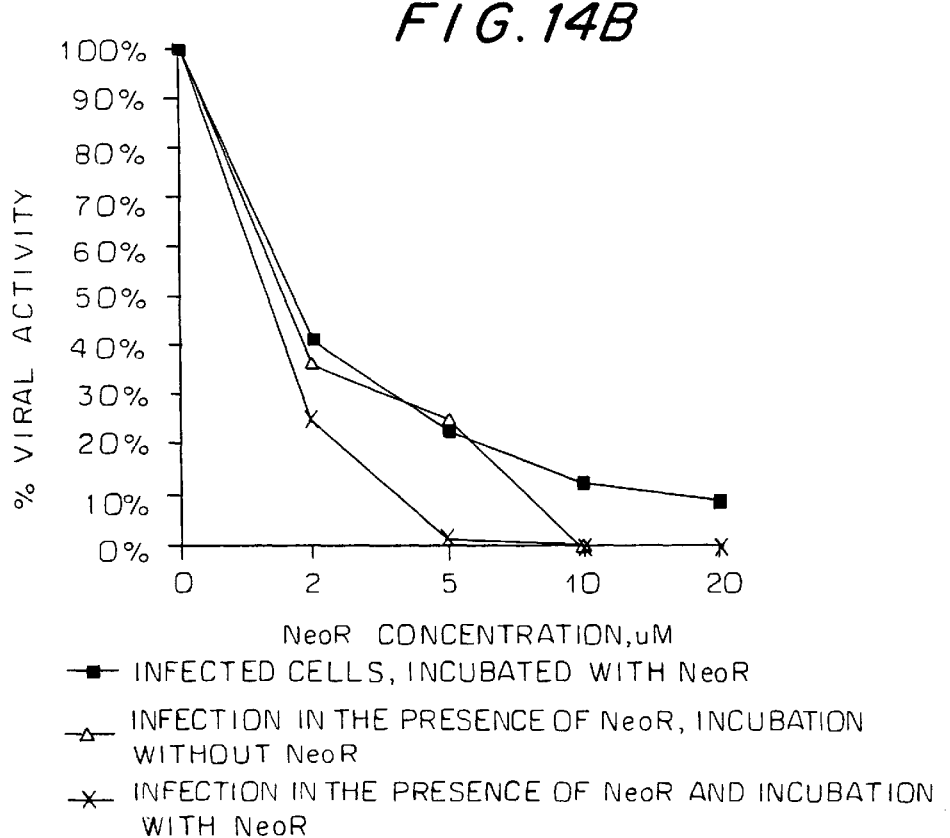

FIGS. 14A–14B show the effect of R3G and NeoR on HIV-1 clade C infection of MT2 cells. Infection of MT2 cells was carried out for 2 hrs with or without 20 μM R3G or 10 μM NeoR followed by cell wash. Around $5 \times 10^4$ cells were seeded per well in 96-well plate and were incubated for 3 days in the presence or absence of 10–20 μM R3G or 5–10 μM NeoR, until syncytia were observed (~25% cpe). Cell viability was tested by tetrazolium-based colorimetric method.

Figure 15A:
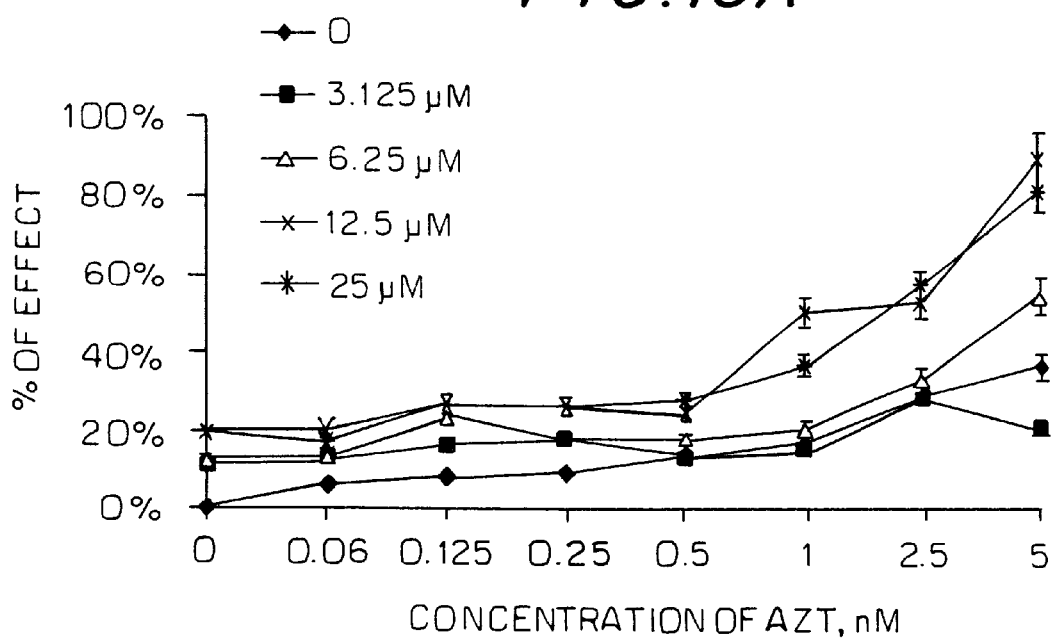
Figure 15B:
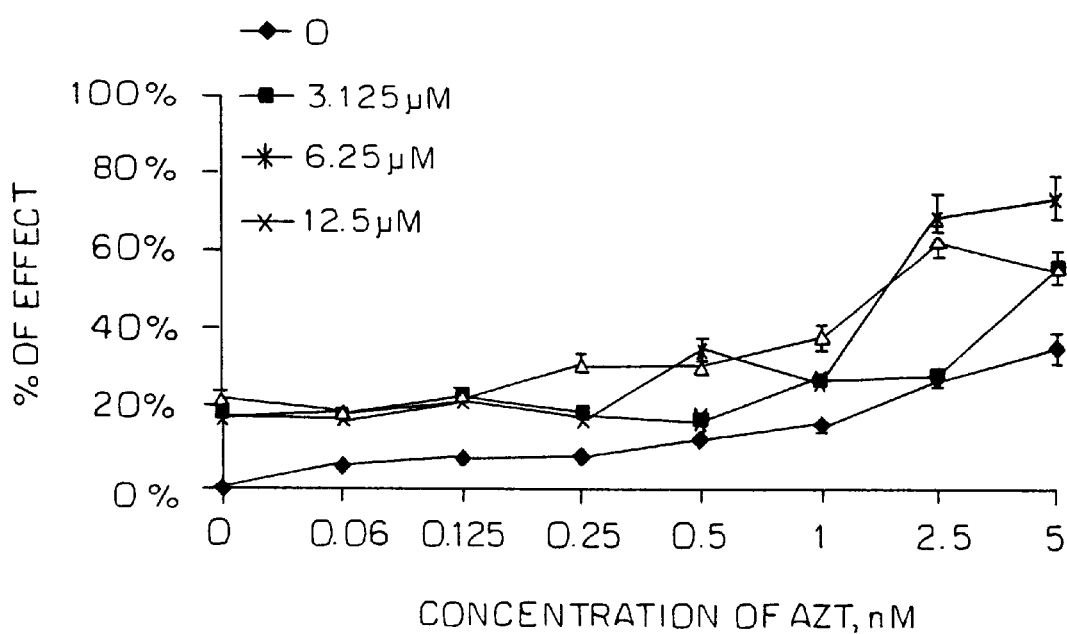

FIGS. 15A–15B show the additive antiviral effect of R3G (15A) or NeoR (15B) and AZT on HIV-1 2D strain. Infection of MT2 cells was carried out for 2 hrs followed by cell wash. Around $5 \times 10^4$ cells were seeded per well in 96-well plate and were incubated for 5 days with varying concentrations of R3G and AZT (15A) or NeoR and AZT (15B), until syncytia were observed. Cell viability was tested by tetrazolium-based colorimetric method.

Figure 16A:
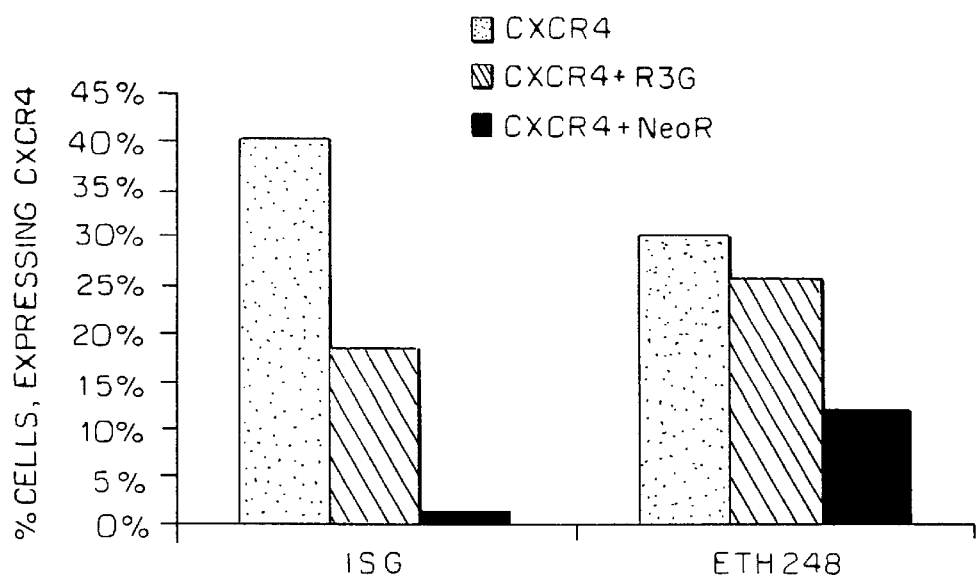
Figure 16B:
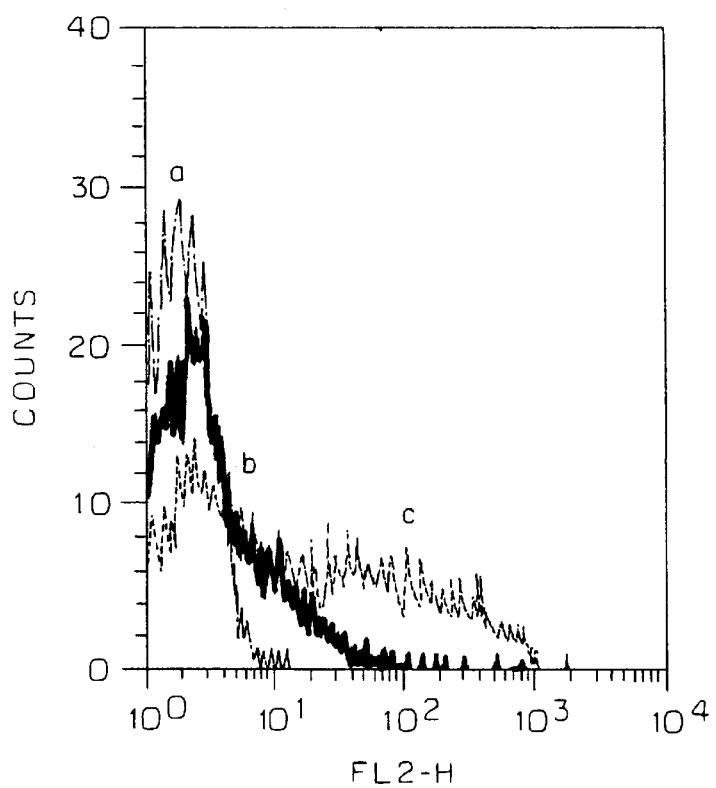
Figure 17A:
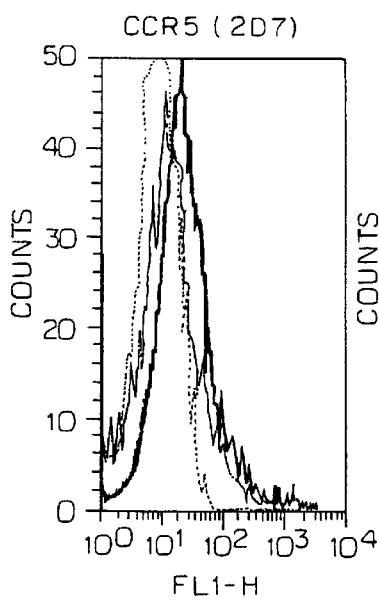
Figure 17B:
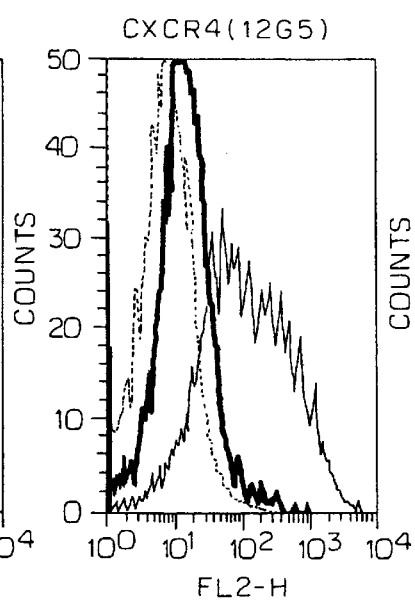
Figure 17C:
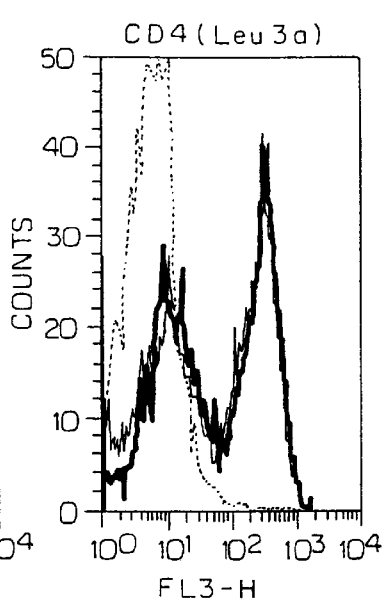
Figure 17D:
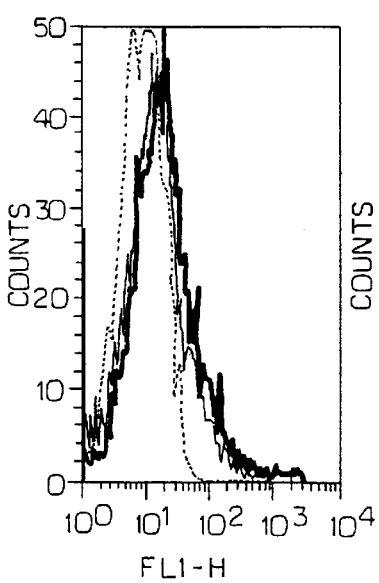
Figure 17E:
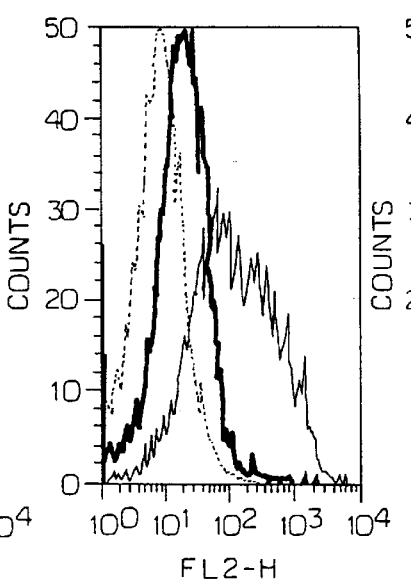
Figure 17F:
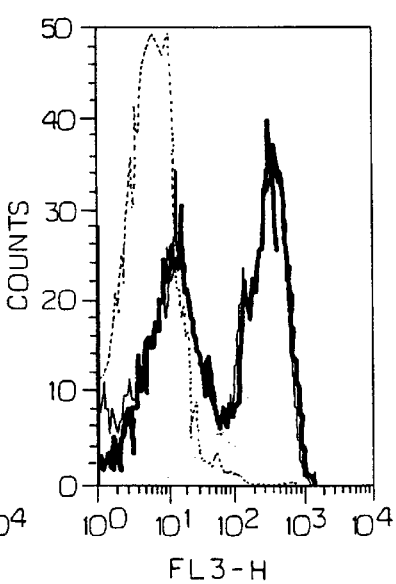

FIGS. 16A–16B show flow cytometry analysis of the interaction of R3G or NeoR with the chemokine SDF-1α receptor CXCR4 on PHA-activated PBMC. FIG. 16A. PMBC lines ETH, derived from an HIV-negative Ethiopian blood sample, and IS, derived from an HIV-negative Israeli blood sample (healthy controls) were incubated in RPMI 1640 containing 10% FCS in the presence of PHA for 24 hrs. Cells ($0.5 \times 10^6$) were washed in ice-cold PBS and incubated for 30 minutes at 4° C. with monoclonal antibody (mAb) 12G5 (anti-CXCR4), conjugated to phycoerythrin (PE) or with isotype control mAbs in the presence or absence of R3G or NeoR. Then, the cells were washed and fixed in 1% formaldehyde. For each sample 10,000 events were analysed in a FACScalibur™ System (Becton Dickinson). Data were acquired and analysed with CellQuest™ software (Becton Dickinson). In the presence of 5 μM R3G or NeoR, the binding of 12G5 to PHA-activated PBMC was suppressed. FIG. 16B. Effect of NeoR (5 μM) on binding of 12G5 mAb to CXCR4 in PHA-activated PBMC. For each experiment cells were incubated with isotype control mAb (a) or anti-CXCR4 mAb (12G5) conjugated to PE in the presence (b) or absence (c) of 5 μM NeoR. After 30 min incubation at 4° C., cells were washed with PBS and analysed by flow cytometry.

FIG. 17 shows the effect of R3G (25 μg/ml) and R4K (25 μg/ml) on binding of 2D7 mAb to CCR5, 12G5 mAb to CXCR4 and Leu3a mAb to CD4 in stimulated-peripheral blood mononuclear cells. For each experiment, cells were incubated with mAbs 2D7, 12G5 or Leu3a conjugated to FITC, PE or PerCP, respectively, or isotype control mAb (dotted line), in the presence (thick line) or absence (thin line) of 25 μ/ml of R3G (upper panels) or R4K (lower panels). After 30 min incubation at 4° C., cells were washed with PBS and analyzed by flow cytometry.

Figure 18A:
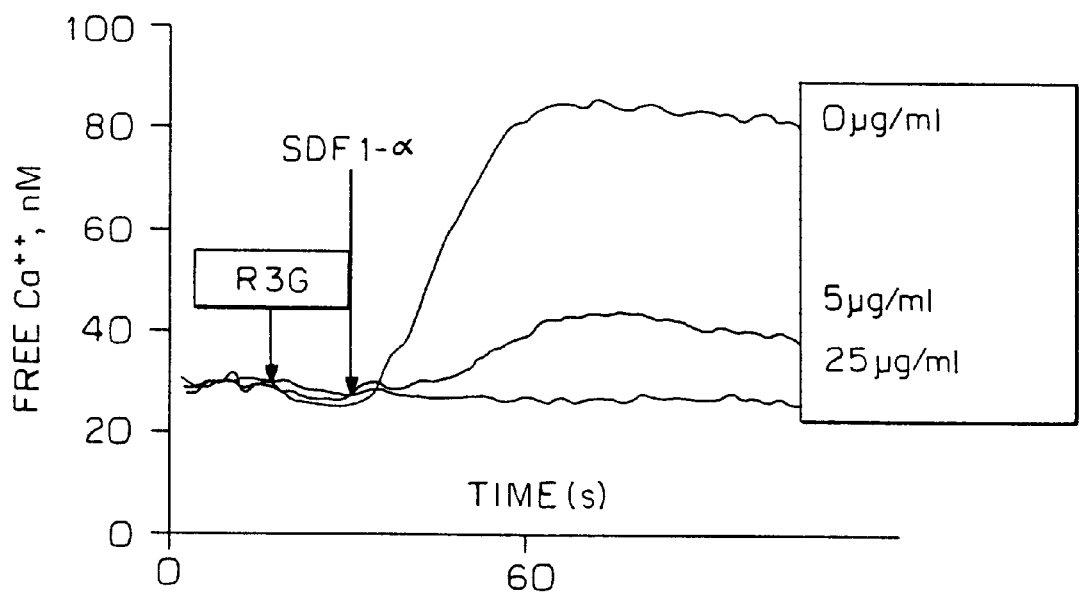
Figure 18B:
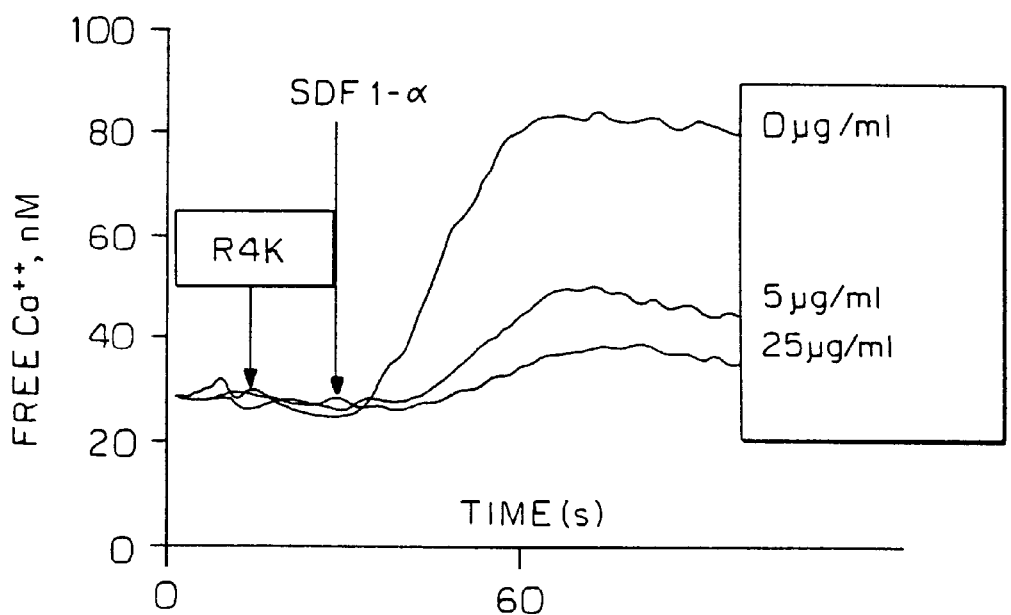

FIG. 18 shows that stromal cell-derived factor 1α (SDF-1α)-induced signaling via CXCR4 is blocked by R3G (upper panel) and R4K (lower panel). SUPT-1 cells were loaded with Fluo-3 fluorochrome and 10 sec after the first stimulation with the appropriate concentration of R3G or R4K, SDF-1α was given as a second stimulus at 20 ng/ml. Fluorescence was measured in a Fluoroskan fluorimeter as described in Methods.

Figure 19:
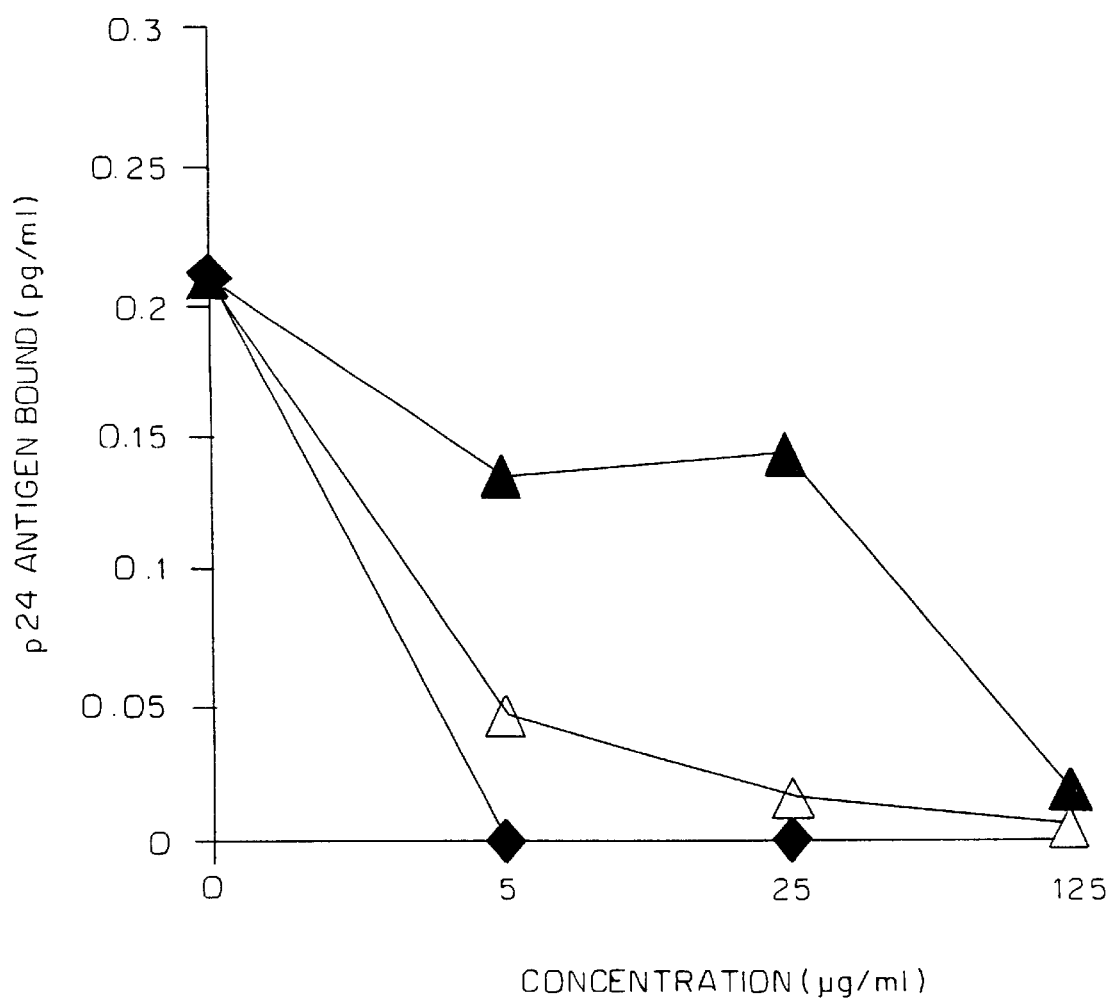

FIG. 19 shows that R3G and R4K inhibit binding of HIV-1 to CD4+ cells. MT-4 cells were infected with $1 \times 10^5$ pg of p24 antigen of HIV-1 (NL4-3) in the presence of different concentrations of the corresponding compound. After 1 hour incubation a 37° C., cells were washed 3 times in PBS and p24 antigen bound to cells was determined by an ELISA test: R4K (black triangles), R3G (white triangles), dextran sulfate (black diamonds).

DETAILED DESCRIPTION OF THE INVENTION

According to the present invention, conjugates of saccharides and acetamidino or guanidino compounds are provided. These conjugates display high affinity to TAR RNA, being almost as efficient as Tat R52 peptide.

The saccharide may be a simple monosaccharide such as a pentose, e.g. arabinose, xylose, ribose, or a hexose, e.g.

glucose, mannose, galactose, fructose It may also be an oligosaccharide such as a disaccharide, e.g. sucrose, maltose, lactose, cellobiose, a trisaccharide, e.g mannotriose, raffinose, melezitose, or a tetrasaccharide. Also encompassed within the definition of saccharide according to the invention are derivatives of saccharides such as, but not limited to, glucosides, ethers, esters, acids and amino sugars.

The saccharide residue may be linked to the spacer X through any suitable group, for example through an alkylene chain or, preferably, through an acylamino group. When the saccharide has no amino group, the amino group is introduced, for example at position 6 of the monosaccharide, by known methods such as by azide displacement on sugar sulphonates or halides, for example as described in Scheme 1 and Example 2c herein for the preparation of compound 7.

In a preferred embodiment, the saccharide is a natural aminoglycoside antibiotic such as, but not limited to, kanamycin, gentamicin, neomycin, seldomycin, tobramycin, kasugamycin, etc.; or synthetic polyamino oligosaccharides. The aminoglycoside-arginine conjugates of the invention are herein sometimes referred to as AAC. Preferred conjugates according to the invention are those herein identified as R4K, R3G and NeoR.

The conjugates of the invention can be prepared by standard methods. In one embodiment, the amino-sugar, e.g. aminoglycoside antibiotic, is reacted with arginine, thus obtaining conjugates of formula I wherein A is $NH_2$ and X is $—(CH_2)_3—CH(NH_2)—C(=O)—$. In another embodiment, the conjugates can be prepared by reaction of $\alpha,\omega$-diamino acids of varying chain length such as $\beta$-alanine, ornithine and lysine (2, 3 and 4 methylene groups, respectively) or co-amino acids such as glycine (aminoacetic acid), $\beta$-amino propionic acid or $\gamma$-amino butyric acid, with the aminoglycosides, and conversion of the terminal amino groups into guanidino or N-acetamidino moieties by treatment with a variety of guanilating agents such as O-methyl isourea, S-methyl isothiourea and others or with O-ethyl acetimidate, according to known procedures.

The conjugates of the invention were found to be non-toxic for cultured cells, even at relatively high concentrations.

Based on peptide models of TAR RNA binding, NMR structures of TAR-ligand complexes and aminoglycoside-RNA interactions, we designed and synthesized according to the present invention a set of novel peptidomimetic substances, conjugates of aminoglycoside antibiotics with arginine. The combination of arginine residues and an aminoglycoside core results in new compounds with structural features of both the oligocationic peptides and the aminoglycosides. These aminoglycoside-arginine conjugates (AAC) display high affinity to TAR RNA in vitro: $K_d$'s of AAC-TAR complexes measured by gel-shift technique were found to be in the range of 20–400 nM, comparable to the $K_d$ of the native Tat-TAR complex (6–12 nM). The finding that gel-electrophoretic mobilities of the AAC-TAR differ from peptide-TAR complexes, suggests that the stoichiometry of the complex between AAC and TAR RNA in vitro is not equimolar. Their binding sites on TAR RNA were assigned by RNase A, uranyl nitrate and lead acetate footprinting. The conjugates interact with TAR RNA in the widened major groove, formed by the UCU bulge and the neighbouring base pairs of the upper stem portion of TAR, the binding site of Tat protein and Tat-derived peptides (e.g. R52). Our results suggest an additional binding site of R4K and R3G compounds, in the lower stem-bulge region of TAR.

Aminoglycoside-arginine conjugates are non-toxic for cultured mammalian cells. The fluorescently labeled AAC of the invention efficiently accumulate in mammalian cell nuclei as was determined by confocal fluorescent microscopy studies. They are also expected to be resistant to enzymatic degradation that comprises one of the main problems for peptide therapies. They further inhibit EIAV proliferation in cultured equine dermal a fibroblasts, as well as HIV-1 infection and proliferation in cultured human lymphocytes.

Pharmaceutical compositions for use in accordance with the present invention may be formulated in conventional manner using one or more physiologically acceptable carriers or excipients. The carrier(s) must be acceptable in the sense that it is compatible with the other ingredients of the composition and are not deleterious to the recipient thereof.

The pharmaceutical composition will be administered by any suitable method including, but not being limited to, parenteral, e.g intravenous, intraperitoneal, intramuscular, subcutaneous, mucosal, e.g. oral, intranasal, intraocular.

For oral administration, the pharmaceutical preparation may be in liquid form, for example, solutions, syrups or suspensions, or in solid form as tablets, capsules and the like. For administration by inhalation, the compositions are conveniently delivered in the form of drops or aerosol sprays. For administration by injection, the formulations may be presented in unit dosage form, e.g. in ampoules or in multidose containers with an added preservative.

The dose of the conjugate of the invention to be administered will depend on the viral disease to be treated, on the individual's age and health condition, and other parameters as well known to physicians. The conjugates may be used for the purpose of prevention and treatment of HIV-infection and AIDS, either alone or in combination with other compounds used in AIDS treatment such as, but not limited to, AZT and/or protease inhibitors, as a part of anti-AIDS cocktails. The conjugates of the invention may be administered together with, before or after the AZT or protease inhibitors, in suitable administration forms and dosages as prescribed by the physicians. This combination therapy is suitable for the treatment of HIV-infection, AIDS and AIDS conditions/manifestations such as Kaposi sarcoma.

The invention further relates to a method for treatment of HIV-infection, AIDS or conditions/manifestations derived from HIV-infection and AIDS, which comprises administering to an individual in need thereof, an effective amount of a conjugate of the invention, either alone or in combination with appropriate compounds used in AIDS treatment, to achieve alleviation of said infection or condition. An example of such condition is Kaposi sarcoma and examples of compounds used in AIDS treatment are, without being limited to, AZT and protease inhibitors.

The invention will now be illustrated by the following non-limiting Examples.

EXAMPLES

For convenience and better understanding, the section of the Examples is divided into two subsections: (I) the Chemical Section describing the synthesis of the conjugates, and (II) the Biochemical and Molecular Biology Section describing the biological activity of the conjugates.

I CHEMICAL SECTION

In the Examples herein, the conjugates of the invention (10–20), other compounds prepared for testing their suitability as antivirals (4,7–9) and the intermediates (1–3, 5, 6) will be presented by their respective Arabic numbers in bold according to the following List of Compounds. The corresponding formulas appear in Scheme I (compounds 1–12), Scheme 2a (compound 13-R4K), Scheme 3a (compound 14-R3G), Scheme 3b (compound 15-R4GC$_{1a}$), Scheme 4 (compounds 16–17), Scheme 4a (compound 20) and Scheme 5 (compounds 18–19).

List of Compounds
1. Methyl α-D-mannopyranoside
2. Methyl 2,3,4-tribenzoyl-6-tosyl-α-D-mannopyranoside
3. Methyl 2,3,4-tribenzoyl-6cyano-α-D-mannopyranoside
4. Methyl 6-deoxy-6-cyano-α-D-mannopyranoside
5. Methyl 2,3,4tribenzoyl-6-azido-α-D-mannopyranoside
6. Methyl 6-deoxy-6-azido-α-D-mannopyranoside
7. Methyl 6-deoxy-6-amino-α-D-mannopyranoside
8. Methyl 6-deoxy-α-D-mannoheptopyranuronic acid amide
9. Methyl 6-deoxy-α-D-mannoheptopyranuronic acid amidoxime
10. Methyl 6-deoxy-6-guanidino-α-D-mannopyranoside
11. Methyl 6-deoxy-6-(N-acetamidino)-α-D-mannopyranoside
12. Methyl 6-deoxy6-(N-L-argininamido)-α-D-mannopyranoside (RMMP)
13. Tetraargininamido-kanamycin A conjugate (R4K)
14. Triargininamido-gentamicin conjugate (R3G)
15. Tetraarginamido-gentamicin (C$_{1a}$) conjugate (R4GC$_{1a}$)
16. γ-(N-acetamidino)butyramido-neomycin B conjugate
17. γ-(N-guanidino)butyramido-neomycin B conjugate
18. Tetra-γ-(N-acetamidino)butyramido-kanamycin A conjugate
19. Tetra-γ-(N-guanidino)butyramido-kanamycin A conjugate (GB4K)
20. Hexa/penta-argininamido-neomycin B conjugate (NeoR)

EXAMPLE 1.
Preparation of compound 4
The synthesis of the cyano-monosaccharide 4 was carried out as depicted in Scheme 1 herein, by tosylation of the 6-hydroxy and benzoylation of the 2,3,4-hydroxy groups of the starting compound 1, conversion of the 6-tosyl group of the obtained compound 2 into a 6-cyano group, and removal of the benzoyl protecting groups from the obtained compound 3.

1a. Preparation of compound 2
To an ice-cold solution of 5 g methyl α-D-mannopyranoside (1) in 75 cc of pyridine, a cold solution of 5.5 g of p-toluenesulphonyl chloride in 10 cc pyridine was added dropwise, and then the reaction mixture was kept at room temperature for 18 hrs, and the mixture was cooled again in an ice-bath, and 10 cc of benzoyl chloride was added. After an additional 20 hrs at room temperature, the reaction mixture was poured into 1 liter of ice water, which resulted in the precipitation of pasty mass. The aqueous solution was decanted, and the solid residue was triturated with 100 cc of 2% sodium bicarbonate solution, filtered and washed with water. The solid residue was refluxed with 50 cc of ethyl alcohol for 5 min, filtered while hot, and the extraction was repeated with another 50 cc of ethyl alcohol. The remaining insoluble compound 2 weighed 6.7 g after being dried over P$_2$O$_5$ overnight. M.p. 198° C.; $^1$H NMR (CDCl$_3$): δ 7.3–8.25 (d and m, 19H, tosyl and benzoyl), 5.95—5.7 (mm 3H, H$_{2-4}$), 5.015 (d, 1H, H$_1$), 4.38 (s 2H H$_{6,6'}$and m 1H H$_5$), 3.6 (s, 3H, OMe), 2.45 (s, 3H, Me$_{Ts}$). [s=singlet, d=doublet, dd=doublet of doublets, AB=AB system, m=multiplet, mm=multiple multiplets, not resolved].

1b. Preparation of compound 3
Compound 2 (14.26 g), NaCN (5.5 g) and tetrabutylammonium bromide (3.5 g) were dissolved in 100 cc of DMF. The reaction was allowed to proceed for 40 hrs at room temperature, after which the reaction mass was poured into 2 liter of water and centrifuged. A pasty pellet was triturated with boiling ethyl alcohol and filtered while hot to remove unreacted compound 2 (approximately 8%). Ethyl alcohol solution was decolorized with charcoal and evaporated in vacuo. Compound 3 was crystallized by addition of methyl alcohol and recrystallized from acetone-methyl alcohol, giving 4.8 g after drying over P$_2$O$_5$. M.p.144° C.; $^1$H NMR (CDCl$_3$): δ 8.22, 8.07, 7.92 (d,d,d, 2H each, benzoyl), 7.38–7.66 (m, 9H, benzoyl), 6.0–5.8 (mm, 3H, H$_{2-4}$), 5.12 (d, 1H, H$_1$), 4.43 (m, 1H, H$_5$), 3.70 (s, 3H, OMe), 2.90 (d, 2H, H$_{6,6'}$), $^{13}$C NMR (CDCl$_3$): δ 165.70, 165.41, 165.32 (C=O benzoyl), 133.81, 133.68, 133.31, 129.93, 129.85, 129.67, 128.68, 128.57, 128.32 (ring benzoyl), 116.38 (CN), 98.77 (C$_1$), 70.12, 69.66, 69.34, 66.65 (C$_2$–C$_5$), 55.79 (Me), 21.52 (C$_6$).

1c. Preparation of compound4
5 g of compound 3 were added to 50 ml abs. MeOH containing 0.08 g MeONa and stirred for 16 hrs at room temperature. Sodium methoxide was neutralized by addition of NH$_4$Cl (0.1 g), and the solution was evaporated in vacuo. Resulting syrup was twice partitioned between 3 cc of water and 50 cc of benzene, decanting benzene and evaporating water layer to dryness. Resulting syrupy compound 4 was dissolved in 30 cc of abs. acetone, filtered to remove salts, and evaporated in vacuo, giving, after drying over P$_2$0$_5$ in high vacuum, 1.95 g of pale yellow syrup. $^1$H NMR (D$_2$O): δ 4.76 (d, 1H, H$_1$), 3.4–3.95 (mm, 4H, H$_{2-5}$), 2.9 (AB, 2H, H$_{6,6'}$) $^{13}$C NMR (D$_2$O): δ 101.11 (C$_1$) 69.98, 69.69, 69.35, 67.87 (C$_{2-5}$), 54.76 (Me), 20.06 (C$_6$).

EXAMPLE 2.
Preparation of compound 7
The synthesis of the amino-monosaccharide 7 was carried out as depicted in Scheme 1 herein, by conversion of the 6-tosyl group of compound 2 into a 6-azido group, removal of the benzoyl protecting groups from the obtained compound 5, and conversion of the 6-azido group of the obtained compound 6 into a 6-amino group.

2a. Preparation of compound 5
10 g of compound 2 and 3 g of NaN$_3$ were dissolved in 100 cc of DMF. Reaction was allowed to proceed for 24 hrs at 70° C. after which the reaction mass was poured into 1 liter of water. Compound 5, obtained as a solid, was recrystallized from acetone giving 8 g (quant.) after drying over P$_2$O$_5$. M.p. 111° C.; $^1$H NMR (CDCl$_3$): δ 8.22, 8.07, 7.92 (d,d,d, 2H each, benzoyl), 7.38–7.66 (m, 9H, benzoyl), 6.0—5.96 (m, 2H, H$_{2,3}$), 5.8 (m, 1H, H$_4$), 5.13 (d, 1H, H$_1$), 4.47 (m, 1H, H$_5$), 3.69 (s, 3H, OMe), 3.62 (AB, 2H, H$_{6,6'}$).

2b. Preparation of compound 6
5.5 g of compound 5 were added to 50 ml abs. MeOH containing 0.08 g MeONa and stirred for 16 hrs at room temperature. Sodium methoxide was neutralized by addition of NH$_4$Cl (0.1 g), and the solution was evaporated in vacuo. Resulting syrup was twice partitioned between 3 cc of water and 50 cc of benzene, decanting benzene and evaporating water layer to dryness. Resulting syrupy compound 6 was dissolved in 30 cc of abs. ethyl alcohol, filtered to remove salts and evaporated in vacuo,, giving, after drying over $P_2O_5$ in high vacuum, 1.3 g of transparent syrup. $^{13}C$ NMR $(D_2O)$: δ 100.90 $(C_1)$ 71.11. 70.18, 69.69, 67.30 $(C_{2-5})$, 54.73 (Me), 50.92 $(C_6)$.

2c. Preparation of compound 7

1 g of compound 6 was dissolved in 20 cc of ethyl alcohol. 0.5 g of 10% Pd on charcoal was added to the solution, and the mixture was stirred overnight under an atmospheric pressure of hydrogen. The catalyst was removed by centrifugation, and the ethanol solution was evaporated in vacuo to yield, after drying over KOH, 0.85 g of title compound 7 as colorless transparent glass. $^1H$ NMR $(D_2O)$: δ 4.73 (d, 1H, $H_1$), 3.91, 3.7, 3.55–3.51 (mm, 4H, $H_{2-5}$), 3.39 (s, 3H, OMe), 2.85 (AB, 2H, $H_{6,6'}$) $^{13}C$ NMR $(D_2O)$: δ 100.73 $(C_1)$ 72.69, 70.33, 69.78, 68.09 $(C_{2-5})$, 54.53 (Me), 41.36 $(C_6)$.

EXAMPLE 3.

Preparation of compound 8

The synthesis of the amido-monosaccharide 8 was carried out as depicted in Scheme 1 herein, by conversion of the 6-cyano group of the compound 4 of Example 1 above into a 6-acetamido group.

Thus, 300 mg of compound 4 were dissolved in 20 cc of ethyl alcohol with 20 cc of 20% $H_{2O2}$, and 0.2 g of NaOH were added to the mixture. Reaction mixture was left overnight at 40° C. Resulting solution was passed through Amberlite IRC-50 ($H^+$) and Dowex 1×8 ($OH^-$) ion exchange resins, and concentrated to a thick syrup which was crystallized from ethyl alcohol/acetone, yielding 200 mg of compound 8 (dried overnight in a desiccator over $P_2O_5$). M.p. 177° C.; $^1H$ NMR $(D_2)$: δ 4.67 (d, 1H, $H_1$), 3.93, 3.73, 3.52 (mm, 4H, $H_{2-5}$), 3.37 (s, 3H, OMe), 2.63 (AB, 2H, $H_{6,6'}$) $^{13}C$ NMR $(D_2O)$: δ 176.27 $(C_{amide})$, 100.67 $(C_1)$, 70.18, 69.88, 69.78, 69.23 $(C_{2-5})$, 54.54 (Me), 37.44 $(C_6)$. Structure confirmed by single-crystal X-ray diffraction.

EXAMPLE 4.

Preparation of compound 9

The synthesis of the amidoximo-monosaccharide 9 was carried out as depicted in Scheme 1 herein, by conversion of the 6-cyano group of the compound 4 of Example 1 above into a 6-acetamidoximo group.

Thus, 300 mg of compound 4 were added to 10 ml of abs. ethyl alcohol containing 0.3 g hydroxylamine base. Solution was heated to 70° C. and, after 30 hrs, refluxed for 10 more hrs. Resulting solution was crystallized from abs. alcohol. Traces of hydroxylamine were removed by washing crystals with 95% alcohol. After desiccation over KOH, crystalline compound 9 weighed 160 mg. It decomposes at 155° C. without melting. $^1H$ NMR $(D_2O)$: δ 4.69 (d, 1H, $H_1$), 3.90, 3.75–3.45 (mm, 4H, $H_{2-5}$), 3.35 (s, 3H, OMe), 2.50 (AB, 2H, $H_{6,6'}$) $^{13}C$ NMR $(D_2O)$: δ 154.60 $(C_{amidoxime})$, 100.57 $(C_1)$, 70.21, 69.99, 69.74, 69.58 $(C_{2-5})$, 54.57 (Me), 32.08 $(C_6)$. Structure confirmed by single-crystal X-ray diffraction.

EXAMPLE 5.

Preparation of compound 10

The synthesis of the guanidino-monosaccharide 10 was carried out according to Yoshimura et al., (1974), as depicted in Scheme 1 herein, by conversion of the 6-amino group of the compound 7 of Example 2 above into a 6-guanidino group.

Thus, 630 mg of compound 7 and 620 mg S-methyl isothiourea sulfate were dissolved in 10 cc of 10% ammonia. The solution was left at room temperature for 4 days, then treated with Dowex 1×8 ($OH^-$) and applied to a column of Amberlite IRC-50 ($H^+$, 15 cc). The column was washed successively with deionized water (200 cc), 5% aqueous ammonia (200 cc) and water (200 ml) and then eluted with 0.5M HCl. The neutral effluent was collected until the pH changed, and it was evaporated to dryness. The dry residue was extracted with abs. ethyl alcohol, the extract was evaporated, redissolved in water and then passed through Dowex 1×8 ($OH^-$). Upon evaporation, the dry syrupy title compound 10 weighed 385 mg. $^1H$ NMR $(D_2O)$: δ 4.74 (d, 1H, $H_1$), 3.92, 3.73–3.39 (dd, mm, 6H, $H_{2-5,6,6'}$), 3.37 (s, 3H, OMe), $^{13}C$ NMR $(D_2O)$: δ 158.97 $(C_{guanidine})$, 102.16 $(C_1)$ 72.24, 71.57, 71.08, 68.77 $(C_{2-5})$, 55.99 (Me), 43.41 $(C_6)$.

EXAMPLE 6.

Preparation of compound 11

The synthesis of the acetamidino-monosaccharide 11 was carried out as depicted in Scheme 1 herein, by conversion of the 6-amino group of the compound 7 of Example 2 above into a 6-acetamidino group.

Thus, 400 mg of compound 7 and 600 mg of ethyl acetimidate hydrochloride (Pinner, 1883) were dissolved in 10 cc of abs. alcohol with 1 cc of triethylamine. The solution was left at room temperature for 6 hrs, then evaporated. The residue was dissolved in 10 cc of water and treated with Dowex 1×8 ($OH^-$) and applied to a column of Amberlite IRC-50 ($H^+$, 15 cc). The column was washed successively with deionized water (200 cc), 10% aqueous ammonia (200 cc) and water (200 ml) and then eluted with 0.5M HCl. The neutral effluent was collected until the pH changed, and it was evaporated to dryness. The dry residue was extracted with abs. ethyl alcohol, the extract was evaporated, redissolved in water and then passed through Dowex 1×8 ($OH^-$). After evaporation, and overnight storage over KOH, a dry syrupy compound 11 weighing 150 mg was obtained. $^1H$ NMR (hydrochloride, $D_2O$): δ 4.74 (d, 1H, $H_1$), 3.96, 3.89–3.58 (m,mm, 1H, 5H, $H_{2-5,6,6'}$), 3.40 (s, 3H, OMe), 2.28 (s, 3H, $CH_{3\ amidine}$) $^{13}C$ NMR $(D_2O)$: δ 165.84 $(C_{amidine})$, 100.79 $(C_1)$ 70.05, 69.63, 69.61, 67.28 $(C_{2-5})$, 54.64 (OMe), 42.58 $(C_6)$, 18.25 $(CH_{3\ amidine})$.

EXAMPLE 7.

Preparation of compound 12

The synthesis of the argininamido-monosaccharide 12 was carried out as depicted in Scheme 1 herein, by conversion of the 6-amino group of the compound 7 of Example 2 above into a 6-argininamido group.

Thus, 300 mg of compound 7 and 555 mg of L-Nα-carbobenzoxy, Nω-nitro arginine (Sigma Corp.) were dissolved in 4 cc of dry DMF. 324 mg of N,N-dicyclohexyl carbodiimide (DCC) were added and the solution was stirred at room temperature for 16 hours and then evaporated. The residue was washed with chloroform, dissolved in 15 cc of ethyl alcohol/dioxane (1:1 v/v) and filtered. The solution was hydrogenated, using 0.3 g of 10% Pd/C, at atmospheric pressure for 8 hrs, and then evaporated. The residue was dissolved in water and re-hydrogenated for additional 24 hours using the same catalyst. The filtered solution was passed through Dowex 1×8 ($OH^-$) and then applied to a column of Amberlite IRC-50 ($H^+$). The column was washed successively with deionized water, 2N aqueous ammonia and water and then eluted with 0.5M HCl. The neutral effluent was collected until a pH change, and evaporated to dryness. The dry residue was extracted with abs. ethyl alcohol, the extract was evaporated, re-dissolved in water and then passed through Dowex 1×8 ($OH^-$). The solution was evaporated and the residue stored over KOH overnight, resulting in the dry syrupy title compound 12 which weighed 140 mg. $^1H$ NMR $(D_2O)$ contained characteristic protons of the carbohydrate: δ 4.74 $(H_1)$, 3.36 (OMe) and argininamide: δ 3.62 $(H_{\alpha arg})$, 3.19 $(H_{\beta arg})$, 3.62 $(H_{\gamma-\delta arg})$ $^{13}C$ NMR $(D_2O)$: δ 180.63 $(C_{amide})$, 155.47 $(C_{guanidine})$ 103.70 $(C_1)$ 73.45, 73.18, 72.69, 70.96 $(C_{2-5})$, 57.53 (OMe), 57.22

($C_{\alpha arg}$) 43.60 ($C_6$), 42.737 ($C_{\beta arg}$), 34.25 ($C_{\gamma arg}$), 27.32 ($C_{\delta arg}$). DEPT158 experiment has confirmed the nature of $C_6$ and $C_{\gamma\text{-}\delta arg}$ peaks ($CH_2$).

EXAMPLE 8.

Preparation and characterization of the aminoglycoside-arginine conjugates 13–15, 20

8a. General procedure for preparation of conjugates 13–15, 20

Three general procedures were used for the preparation of the conjugates of the invention 13–15 and 20 between arginine and the aminoglycoside antibiotics kanamycin, gentamicin and neomycin, which is also appropriate for other aminoglycoside antibiotics.

Method 1.

1–10 mmoles of aminoglycoside antibiotic are dissolved in 10 cc of dry DMF. For each amino group of the aminoglycoside, one equivalent of the protected arginine derivative and 1.15 equivalent of DCC are added in 4–5 portions during 8 hours. The reaction is allowed to proceed for 32 hours at room temperature. The precipitated N,N-dicyclohexyl urea is removed by filtration and the precipitate is washed with 2 cc DMF. The filtrate is then evaporated in vacuo, and washed with water and chloroform. The residue is dissolved in 20 cc. ethyl alcohol/dioxane (1:1 v/v), containing 1 equivalent of acetic acid per each positively charged group of the conjugate (based on theoretical yield) and hydrogenated at atmospheric pressure for 12 hours over 0.5 g 10% Pd/C. The solvents are evaporated and the residue is dissolved in 20 cc. water and hydrogenation is continued for another 24 hours. The catalyst is removed by centrifugation and the solution is evaporated in vacuo, resulting in faintly yellow, strongly basic viscous syrup, which is dissolved in 15 cc. water. The solution is then passed through a column of Dowex 1×8 ion exchange resin ($OH^-$ form) to remove the free L-arginine and applied onto a column containing 20 cc. swollen Amberlite IRC-50 ion exchange resin ($H^+$ form). The column is washed successively with deionized water, concentrated (5N) ammonia and water, and then the conjugate is eluted with 0.5M HCl. The neutral fractions are collected and evaporated to dryness, and the solid residue is extracted with absolute alcohol. Extracts are evaporated and redissolved in 15 cc. of water. Solution is passed through Dowex 1×8 ion exchange resin ($OH^-$ form), and evaporated to dryness, resulting in 100–300 mg of glassy solid of the desired conjugate of 85% –90% purity. Overall yield: 10–15%. For higher purity, the crude conjugate was applied onto a 10×250 mm HiBar column (C-18, Merck) and chromatographed in a 40-min gradient from 0 to 40% acetonitrile/0.1% trifluoroacetic acid (TFA) at 2.5 ml/min. Peaks of interests were eluted at 22.5–27.5 min. The TFA salts of the conjugates were used only for in vitro studies; free bases conjugates were utilized in the cell culture experiments, due to significant toxicity of the TFA anion. The conjugates were characterized as described below.

Method 2.

1–10 mmoles of aminoglycoside antibiotic are dissolved in 3 cc of deionized water. For each amino group of the aminoglycoside, one equivalent of the protected arginine derivative is added in 10 cc of alcohol/dioxane/water mixture. The final composition of the solvent is around 1:1:1 alcohol/dioxane/water that allows solubility of both aminoglycoside and protected arginine. Equimolar quantity of a water-soluble carbodiimide (e.g. 1-ethyl, 3-(3-dimethyl aminopropyl) carbodiimide) is added in 4–6 portions during 12 hours at room temperature. The reaction progress is monitored by TLC on silicagel-coated plates in a buffer containing isopropyl alcohol:25% water ammonia:chloroform in a ratio of 2:0.5:1. Typical duration of the reaction is 24 hours. The reaction mixture is then evaporated in vacuo, and washed with water. The residue is extracted with alcohol. The remaining solid comprises 80–90% pure protected aminoglycoside-arginine conjugate (yield around 35%). It is hydrogenated and purified as described in Method 1. Overall yield: 15–25%.

Method 3.

1–10 mM of aminoglycoside antibiotic are dissolved in 10 cc of water/alcohol/dioxane mixture. For each amino group of the aminoglycoside, one equivalent of N-hydroxy succinimide ester of Nα-tert-butoxy carbonyl, Nω-carbobenzoxy-L-ornithine is added during 12 hours. The reaction mixture is evaporated, the residue is washed with deionized water and the carbobenzoxy protective group is removed by catalytic hydrogenation, as described in Method 1. The resulting conjugate of Nα-tert-butoxycarbonyl L-ornithine with the corresponding aminoglycoside antibiotic is treated with 12–15 equivalents of S-methyl isothiourea sulfate in 5% aqueous ammonia for 3–5 days. The resulting conjugate of Nα-tert-butoxycarbonyl L-arginine with the corresponding aminoglycoside antibiotic is deprotected in 100% TFA in the presence of 10 equivalents of dimethyl sulfide for 8 hours at room temperature. The further purification and characterization of the conjugate are performed as in Method 1 (overall yield: 25–35%).

8b. General procedures for characterization of conjugates 13–15, 20

1 and 2D, $^1H$ and $^{13}C$ NMR spectra of the compounds were taken in $D_2O$, (unless otherwise stated) at 21 ° C. using the following spectrometers: Bruker DPX 250 (250 MHz), Bruker DPX 400 (400 MHz) and Bruker DPX 500 (500 MHz). Mass spectra of the compounds were obtained with FAB high resolution mass spectroscopy.

8c. Preparation/characterization of kanamycin A tetraarginine conjugate 13 (R4K)

The starting antibiotic kanamycin (Fluka) was a mixture of three major components A, B and C (see Scheme 2), of which the A isomer was the most abundant ~80%). The conjugate of arginine with kanamycin was prepared by standard peptide chemistry methods as described in Example 8a above. As expected, the kanamycin A derivative comprised approximately 90% of the arginine-kanamycin conjugate (R4K) mixture.

R4K was characterized as a free base and consisted, according to HPLC, of essentially one product, the kanamycin A derivative. The $^1H$ NMR (400 MHz, $D_2O$) spectrum revealed the presence of the characteristic groups of the protons of arginine amide moieties at chemical shifts of (δ) 3.38 ($H_\alpha$), 3.21 ($H_\beta$) and 1.64 ppm ($H_{\gamma,\delta}$) All the characteristic kanamycin proton signals, in particular the anomeric hydrogens (as doublets at 4.99 and 5.15 ppm), were observed. Integration afforded 1:4 ratio of antibiotic to arginine components. A $^{13}C$ NMR (100,609 MHz 10% $D_2O$) spectrum of R4K revealed carbon resonances of the C-arginine amide moieties and the kanamycin moiety. The presence of antibiotic anomeric carbon signals at δ 101.77 and 101.07 ppm, the amide carbons at 181.13, 180.81, 180.38, 179.76 ppm and the guanidino carbons at 159.47 ppm 5 confirmed the structure of the aminoglycoside-arginine conjugate. FABHRMS of R4K revealed a mass peak of 1109.7 Da (calculated molecular weight of R4K: 1109.25 Da). A second peak of 1067.4 Da (−42.3 from mass peak) was attributed to a loss of aminoamino carbon fragment during ionization.

8d. 2D NMR studies of kanamycin A-tetra arginine conjugate R4K.

Since R4K consisted of essentially one substance, it was suitable for 2D NMR studies. Natural abundance [$^1$H; $^{13}$C] heteronuclear single-quantum coherence (HSQC) and total correlation spectroscopy (TOCSY) spectra of R4K were recorded on a Bruker DPX 500 MHz in D$_2$) at 21° C.

Figure 1A:
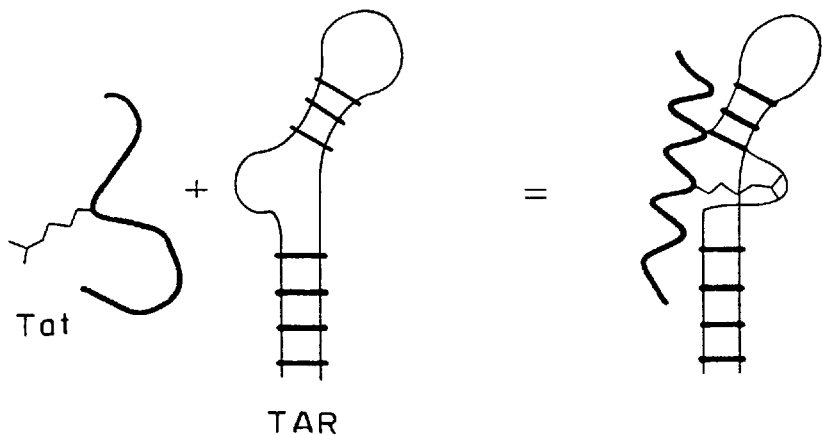
FIGS. 1A–1C are schematic presentations of: (1A) Tat peptide (R52) binding to TAR RNA fragment (31 nucleotides) containing the sequence 18–44 nt of HIV-1 LTR; (1B) Inhibition of Tat peptide (R52) binding to the same TAR RNA fragment by the monosaccharide conjugate of the invention methyl 6-deoxy- 6-(N-L-argininamido)-α-D-mannopyranoside (herein designated RMMP or compound 12); (1C) Binding of tetraargininamido-kanamycin A conjugate of the invention (herein designated R4K or compound 13) to TAR RNA.
Figure 1B:
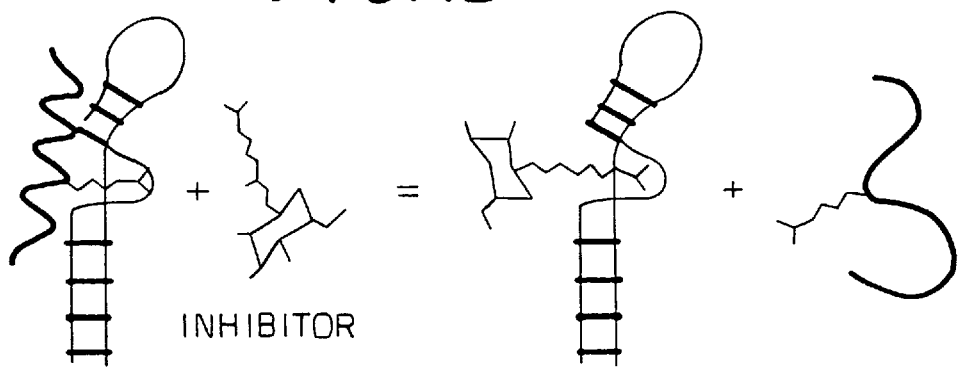
Figure 1C:
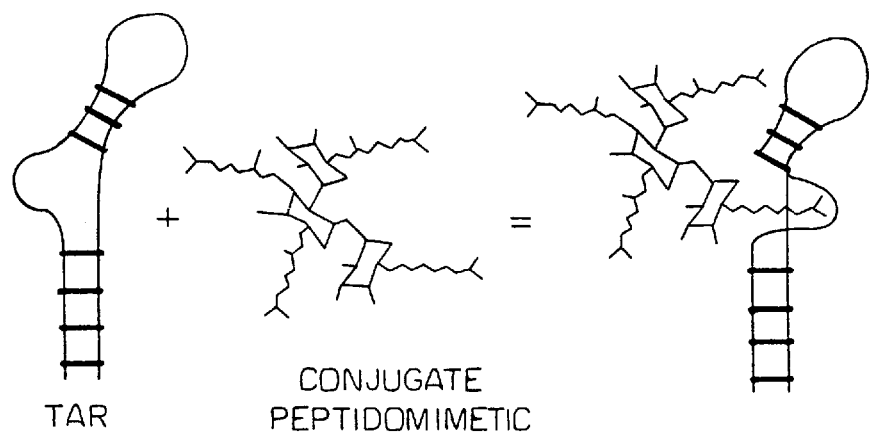
Figure 2:
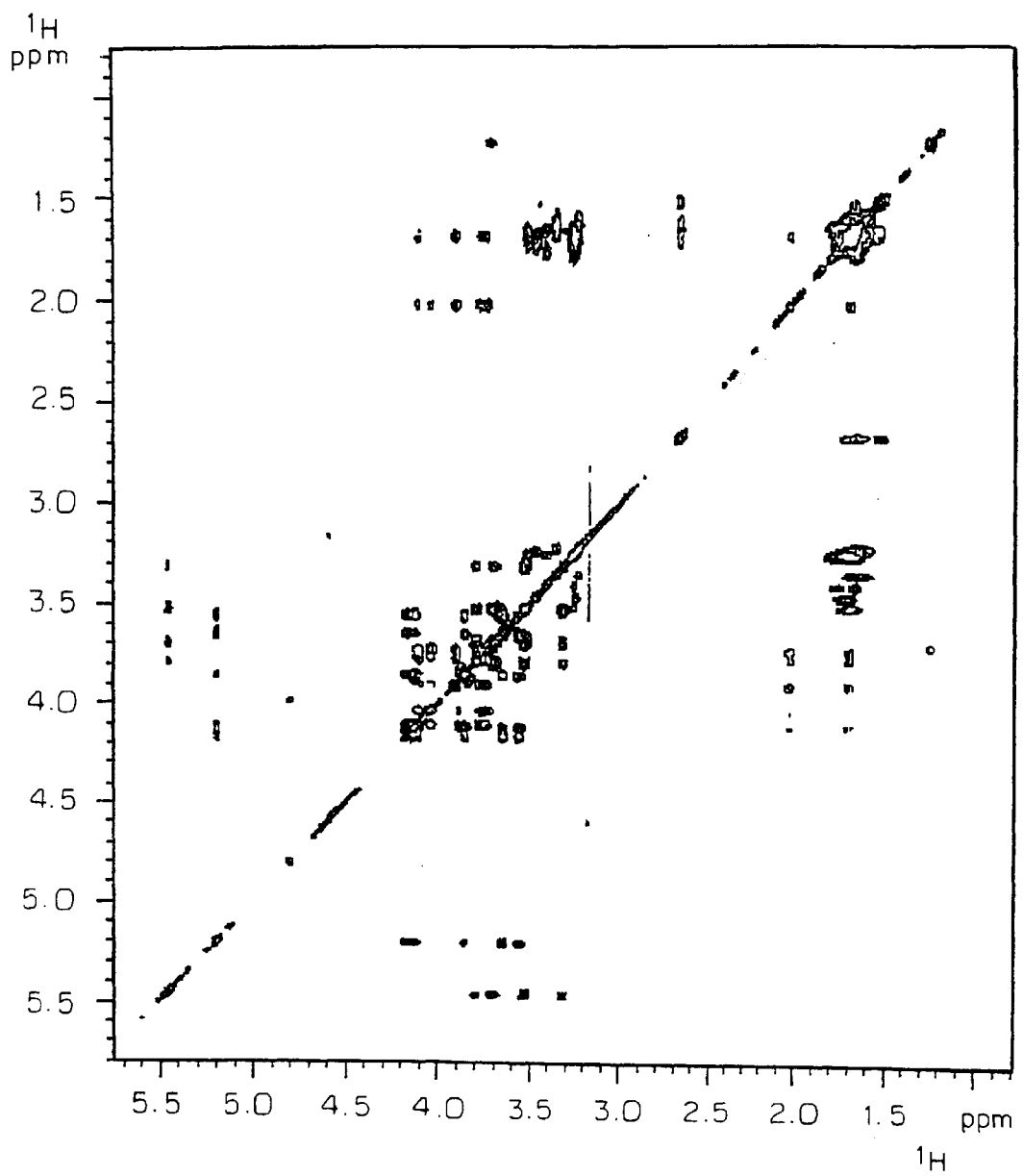
FIG. 2 depicts the $^1$H NMR TOCSY (total correlation spectroscopy) of tetraargininamido-kanamycin A conjugate R4K (compound 13) acquired at 120 ms mixing time, on Bruker DPX 500 MHz in $D_2O$ at 21° C. The spectrum reveals two sugar rings of kanamycin A, emphasized by a correlation with their anomeric protons (5.2 and 5.4 ppm). Additionally, one of the rings correlates with an AB system at 2.0–1.65 ppm (probably $CH_2$—OH). Areas of strong correlation at ~1.6 and ~3.28 correspond to arginine amide moieties.

HSQC reveals the characteristic proton and carbon signal cross-peaks, in particular from the two anomeric protons of the two saccharide rings (δ 4.99 and 5.15 ppm) with corresponding carbons (δ101.1 and 101.8 ppm). TOCSY of R4K (FIG. 2) was acquired at 120 ms mixing time. The spectrum reveals two sugar rings of the antibiotic emphasized by correlation with their anomeric protons at 5.2 and 5.4 ppm. Correlations between the deoxystreptamine axial and equatorial methylene protons (1.65 and 1.92 ppm) and the ring system are observed. Methylene protons at $C_\gamma$ and $C_\delta$ of arginine amide moieties (1.6–1.8 ppm) display correlation with the protons at $C_\beta$ (3.25–3.45) and it is possible to observe 4 arginine side chains (FIG. 3B.). Both spectra contributed much to the correct assignment of the R4K proton and carbon resonances.

8e. Preparation/characterization of gentamicin C$_1$ triarginine conjugate 14 (R3G)

The starting antibiotic gentamicin C (Nova-Biochem) was a mixture of 3 components C$_1$, C$_2$ and C$_{1a}$, that differ by methylation of a single amino group and adjacent CH$_2$ (see Scheme 3). The components were separated chromatographically, as previously described (Cooper et al., 1971). The ratio of the isomers was 4C$_1$: 3C$_2$: 1C$_{1a}$. The preparation of the arginine conjugate with gentamicin C$_1$, R3G (Scheme 3a) was carried out as described above in Example 8a.

R3G was characterized as an acetate salt (at pH 7.0). The substance is a mixture of three products (as was proved by analytical HPLC), the derivatives of gentamicin C isomers (C$_1$, C2 and C$_{1a}$). Since the structural difference between the three components is minor, the substance was used as a mixture in this study. Characteristic arginine amide $^1$H NMR resonances of R3G were observed at ca 3.4 (H$_\alpha$), 3.2 (H$_\beta$) and 1.6 (H$_{\gamma\delta}$) ppm and characteristic antibiotic proton resonances, in particular the anomeric hydrogens, as three groups of doublets at 5.0–5.35; methyl singlets at 2.51 (N-Me of C$_1$, C$_2$ and C$_{1a}$ isomers), 2.32 (N-Me of C$_1$), 1.21 (C-Me of C$_1$, C$_2$ and C$_{1a}$) ppm and methyl multiplet at 1.04 (N-Me of C$_1$, C$_2$). Integration afforded 1:3 average ratio of the gentamicin C components to arginine components, based on the composition of the antibiotic mixture used for the synthesis. A $^{13}$C NMR spectrum revealed carbon resonances at several distinct regions characteristic of C-arginine amide moieties and three gentamicin isomeric moieties. Several C-amide carbon signals at 179.8–179.3 ppm were observed as two groups of three peaks, as well as several minor peaks, indicating the presence of two major isomers, as suggested by the composition of the original antibiotic mixture. Guanidino carbon signals were detected at 160.04 ppm. FAB-HRMS of R3G revealed two prominent mass peaks of 948.3 and 934.3 Da (calculated 948.1 and 934.1 Da), which correspond to the triarginine derivatives of C$_1$ and C$_2$ isomers, differing by a methyl group. Loss of the iminoamino carbon fragment on chemical ionization by FAB-HRMS was also visible.

8f. Preparation and characterization of Gentamicin C$_{1a}$ tetraarginine conjugate 15 (R4GC$_{1a}$)

Preparation of the arginine conjugate of the pure C$_{1a}$ isomer of gentamicin, R4GC$_{1a}$ (Scheme 3b) was carried out as described above in Example 8a. As expected, 4 arginine moieties were found in the conjugate as revealed by $^1$H and $^{13}$C NMR spectroscopy.

8g. Preparation and characterization of hexa-argininamidoneomycin B conjugate 20 (NeoR)

Preparation of the hexa/penta-arginine conjugate of neomycin B (see Scheme 4a) was carried out as described above in Example 8a. Arginine moieties and aminoglycoside parts were found in the conjugate as revealed by $^1$H and $^{13}$C NMR spectroscopy. Integration afforded average 5.5:1 ratio of arginine to neomycin B parts, indicating the presence of hexaarginine and pentaarginine derivatives of neomycin B in the mixture.

EXAMPLE 9.

Synthesis of γ-(N-acetamidino)butyric acid-Neomycin B conjugate (compound 16) and γ-(N-guanidino)butyric acid-Neomycin B conjugate (comp 17)

Conjugates 16 and 17 were prepared by acetamidylation with ethyl acetimidate or guanylation with O-methyl isourea or S-methyl isothiourea of the corresponding γ-amino butyric acid neomycin B conjugate, as depicted in Scheme 4 herein.

9a. Preparation of the neomycin B conjugate with γ-amino butyric acid

The synthesis was carried out via the active ester of γ-amino butyric acid as depicted in Scheme 4, as follows:

2.2 g of N-hydroxysuccinimide ester of (Nγ-carbobenzoxy) γ-amino butyric acid, dissolved in additional 4 ml of formamide was added to 6 ml of neomycin B base (500 mg) solution in formamide. The mixture was stirred for 48 h at room temperature and then poured into 100 ml of 5% NaHCO$_3$ solution, centrifuged and the syrupy pellet washed with 100 ml of water, suspended in chloroform and acetone (20 ml each) to extract unreacted material. The pellet was dried and then dissolved in 20 ml of alcohol containing 0.7 ml of glacial acetic acid. The solution was hydrogenated at atmospheric pressure over 10% Pd/C for 24 h. After removing the catalyst by centrifugation and evaporation in vacuo the conjugate was deionized with Dowex 1×8 (OH form), absorbed on Amberlite IRC-50 (H$^+$form) and eluted from the Amberlite with 25% NH$_4$OH; 200–500 mg (20%–50% yield) of the conjugate was obtained after concentration of the eluate in vacuo. Methanol (abs.) can be substituted for formamide, especially in the case of kanamycin conjugate preparation.

Alternatively, synthesis may be accomplished using the standard DCC coupling protocol, as described above.

9b. Preparation of conjugate 16

For acetamidylation, the neomycin B/γ-amino butyric acid conjugate obtained in Example 9a above is treated with O-ethyl acetimidate in absolute ethanol for 1–2 days, resulting in acetimidylation of the terminal amino groups. The product is purified by ion exchange chromatography, yielding neomycin B/N-acetamidino butyric acid conjugate 16.

9c. Preparation of conjugate 17

For guanylation, the neomycin B/γ-amino butyric acid conjugate obtained in Example 9a above is treated with O-methyl isourea or S-methyl isothiourea in water at basic pH for 34 days, resulting in guanylation of the terminal amino groups. The product is purified by ion exchange chromatography, yielding the neomycin B/γ-guanidino butyric acid conjugate 17.

EXAMPLE 10.

Synthesis of tetra-γ-(N-acetamidino)butyric acid-kanamycin A conjugate (compound 18) and tetra-γ-(N-guanidino) butyric acid-kanamycin A 10 conjugate (compound 19, GB4K)

Conjugates 18 and 19 were prepared by acetamidylation with ethyl acetimidate or guanylation with O-methyl isourea or S-methyl isothiourea of the corresponding γ-amino butyric acid kanamycin A conjugate (see Scheme 5) as described in Example 9 above with some modification. It was not necessary to purify the intermediate GABA-kanamycin conjugate. Best results were obtained when methanol was used as a solvent for the acylation of the kanamycin amino groups by succinimide ester of (N-carbobenzoxy) γ-amino butyric acid.

GB4K was characterized as an acetate salt. Characteristic $^1$H signals of guanidino butyric acid amide chains were observed as multiplets at 3.19 ($H_\beta$), 2.32 (HO) and 1.86 ($H_{\gamma,\delta}$) ppm. All characteristic signals of the kanamycin moiety were found, in particular the anomeric protons as singlets at 5.32 and 5.11 ppm. Integration afforded 1:4 ratio of the antibiotic to guanidino butyric acid amide parts. A $^{13}$C NMR spectrum revealed characteristic groups of signals of both the guanidino-butyric acid amide and the antibiotic moiety. In particular, the antibiotic anomeric carbon signals were observed at 100.03 and 98.04 ppm; the amide carbons at 176.63, 176.22, 175.32 and 174.94 ppm and the guanidino carbons at 157.33 ppm. Using FABHRMS the mass peak was found to be 993.5 Da (calculated 993.1 Da). Loss of the iminoamino carbon fragment upon ionization was also observed.

II BIOLOGICAL SECTION

Materials and Methods (i) TAR RNA and Tat peptide preparation

The model Tat peptide (R52: YKKKRKKKKKA) was prepared by the Weizmann Institute Chemical Services and was purified by reverse phase HPLC (C-18) (Lapidot et al., 1995). A 31-nt TAR RNA fragment (5'-GGC CAG AUC UGA GCC UGG GAG CUC UCU GGC C-3') containing the sequence 18–44 of the HIV LTR (Aboul-Ela et al., 1995) was transcribed in vitro by T7 RNA polymerase (Promega) from a synthetic single strand DNA template containing the 17 base double-stranded T7 promoter (both DNA oligonucleotides were prepared by the Weizmann Institute Chemical Services). The RNA was transcriptionally labeled with α-$^{32}$P UTP, purified on a 12% polyacrylamide/7M urea gel (19:1 acrylamide:bis-acrylamide) and was eluted from the gel by 0.5M ammonium acetate, 10 mM magnesium acetate, 1 mM EDTA and 0.1% SDS. The sample was subjected to phenol extraction and the RNA was precipitated from 70% ethanol. Purified RNA was dissolved in diethyl pyrocarbonate-treated water (DEPC water), its concentration was determined by UV absorption at 260 nm and the specific radioactivity was determined by scintillation counting on a LS 1701 "Bruker" counter.

Alternatively, chemically synthesized TAR RNA oligonucleotide (Dharmacon) was 5'-end labeled with 1 μl (γ-$^{32}$P) ATP (6000 Ci/mmol, Amersham) per 1 nmol of RNA using T4 polynucleotide kinase (Promega) in a buffer containing 70 mM Tris-HCl pH 7.5, 10 mM $MgCl_2$ and 5 mM DTT. The labeled RNA was successively extracted with water-saturated phenol, phenol-chloroform (1:1) and chloroform, and precipitated from 75% ethanol. All RNA samples were annealed by heating them to 95° C. for 5 min, followed by slow cooling to room temperature in a buffer, containing 10 mM sodium cacodylate (pH 6.5) and 50 mM KCl. RNA purity was analyzed by denaturing gel-electrophoresis. The alkaline cleavage of TAR RNA was performed by incubation of 10 μl RNA samples (containing 50–100 ng of 5' $^{32}$P labeled TAR RNA) with 10 mM NaOH for 3–5 min at room temperature. The reaction was stopped by addition of 1 μl 150 mM acetic acid.

(ii) Gel-shift assays

To study the affinity of the test compounds to TAR, gel-shift and gel-shift inhibition experiments were performed. The binding reaction mixtures (20 μl) contained $^{32}$P-labeled TAR (18–44) RNA oligonucleotide (3–6 nM) and Tat R52 peptide (35–75 nM) in a binding buffer (10 mM Tris-HCl pH 7.5, 70 mM NaCl, 0.2 mM EDTA and 5% glycerol). The reaction mixtures were incubated for 10 minutes on ice and resolved by electrophoresis on a 10% non-denaturing polyacrylamide gel (40:1 acrylamide:bis-acrylamide) at 200V, for 3 h at 4° C. Gels were dried and visualized by autoradiography. Quantitations were obtained by optical densitometry of films. Alternatively, results were visualized by exposing the wet gels to Fuji phosphoimager plates, which were read on a "Storm 820" (Molecular Dynamics) phosphoimager. Different concentrations of TAR RNA (6, 12 and 20 nM) were titrated with various concentrations of Tat R52 in the binding reactions. $CD_{50}$ values were defined as the Tat peptide concentration that displayed 50% binding to TAR RNA.

Binding inhibition by the monosaccharide derivatives was measured by adding several concentrations of each compound to reaction mixtures containing 60 nM Tat 52 and 6 nM $^{32}$P TAR, attaining 100% binding of Tat TAR in the absence of inhibitors (Lapidot et al., 1995). The binding inhibition values, $CI_{50}$, were defined as inhibitor concentrations that displayed 50% inhibition of Tat TAR binding.

Binding of aminoglycoside-arginine conjugates (AAC) to TAR RNA was measured by adding varying concentrations of each conjugate to reaction mixtures (20 μl) which contained 12 nM $^{32}$P-labeled TAR RNA. The reactions were analyzed as described above. $CD_{50}$ values were defined as the conjugate concentrations that displayed 50% binding to TAR RNA.

(iii) Affinity chromatography on L-arginine-Amberlite column

Experiments with L-arginine-Amberlite affinity column were performed to obtain further evidence of the specificity of the conjugates binding to TAR (Geiger et al., 1996). The L-arginine-Amberlite resin was prepared as follows: Carboxyl groups of Amberlite IRC-50 resin were covalently modified with ethanolamine using 1-(3-dimethylaminopropyl) 3-ethylcarbodiimide, a water-soluble coupler. The hydroxy ethyleneamide resin obtained was washed and dried, and L-arginine (12–16 μmols per ml of resin) was coupled to the hydroxy groups of the resin via an isourea moiety using a standard cyanogen bromide protocol. The final concentration of arginine residues was 12–16 μmol per ml of resin. The swollen L-arginino-Amberlite resin (200 μl) was packed into a plastic mini-column and equilibrated with buffer containing 40 mM Tris HCl, pH 7.5, 250 mM NaCl, 0.5 mM EDTA and 5 mM $MgCl_2$ (buffer A). Approximately 1 ng of $^{32}$P-UTP labeled TAR RNA in buffer A was loaded on the column. The column was eluted 3 to 5 times with 400 μl portions of buffer A, until no radioactivity was detected in the eluent. The total radioactivity in the eluents did not exceed 3% of the total radioactivity loaded. Each of the test compounds was dissolved in buffer A and passed through the column in 300 μl portions. Radioactivity of the eluates was determined by scintillation counting on a LS 1701 "Bruker" counter. $CE_{50}$ values, the concentrations of inhibitors eluting 50% of the radioactive material from the column, were determined. The eluate samples were proven to contain labeled TAR RNA by electrophoresis on a denaturing 12% polyacrylamide/7M urea gel, followed by autoradiography.

The L-arginine-Amberlite affinity resin described above was found to be more mechanically stable and of better affinity properties than the L-arginine-agarose resin previously used (Tao and Frankel., 1992). This may be due to the higher arginine concentration and 6-atom spacer between the polymer and the arginine residues.

(iv) RNase A footprinting.

In a typical experiment 10 μl of 5 mM cacodylate buffer pH 6.5, containing 25 mM KCl and 50–100 ng 5' $^{32}$P-labeled TAR RNA (approximately 0.5–1 μM) were incubated with 200 pM RNase A (Sigma) at room temperature for 10 minutes in the presence of Tat R52 and the conjugates of the invention at various concentrations. In the competition experiments, the mixture was supplemented with 0.5 μg yeast tRNA (Sigma). After the incubation, 10 μl of formamide/bromphenol blue loading buffer was added to the samples. The samples were heated to 80° C. for 2 min and were resolved by electrophoresis on 40 cm×0.8 mm 20% polyacrylamide denaturing gel (7M urea) for 3 hours at 55° C. The results were visualized by a phosphoimager as described above and quantitated using ImageQuant software.

(v) Lead acetate footprinting.

In a typical experiment, 10 μl of 50 mM cacodylate buffer pH 6.5, containing 100 mM KCl, 1 mM MgCl$_2$ and 0.5 μg yeast tRNA were incubated with 50 ng 5' $^{32}$P labeled TAR RNA (approximately 0.5 μM) in the presence of varying concentrations of Tat R52 and the AAC of the invention at room temperature for 5 minutes. Cleavage reactions were initiated by addition of Pb(OAc)$_2$ to final concentrations of 0.1 mM. After 20 min incubation, 10 μl of 90% formamide/bromphenol blue loading buffer, containing 100 mM EDTA, was added to the samples. The samples were heated to 80° C for 2 min and were resolved by electrophoresis and quantitated as described above.

(vi) Uranyl nitrate photocleavage.

The procedure for photoinduced cleavage of TAR RNA by uranyl cation was as following: 50 μM uranyl nitrate were added to 10 μl of 5 mM cacodylate buffer pH 6.5 or 5 mM KMOPS buffer, pH 7.5, containing 25 mM KCL and 1 μM 5' $^{32}$P labeled TAR RNA. Inhibitors or divalent metal salts were added to the mixture at various concentrations. Tracing of the hypersensitive cleavage sites was performed in the presence of 37.5 μM citrate. The samples were irradiated for 10–20 minutes at room temperature under a Philips T1 40 W/03 fluorescent tube, emitting light at wavelength of 420 nm. Following irradiation, the samples were treated, resolved by electrophoresis and quantitated as described above.

(vii) Cytotoxicity measurements

All the conjugates of the invention that were found to inhibit Tat-TAR interaction or to bind TAR RNA were tested for toxicity in the following cell cultures: LAN 1 (human neuroblastoma), MPC 11 (murine plasmacytoma), MT4 (human T-lymphocytes) and ED (equine dermal fibroblasts). Approximately 2.5×10$^4$ cells were seeded per each well of the standard 96-well "Falcon" tissue culture plate in 200 μl DMEM containing 10% heat-inactivated fetal calf serum (FCS). Different concentrations of the compounds were added to the wells in triplicates. After 24 to 48 hours incubation the cells were washed and the medium was changed for the same amount of DMEM/10% FCS containing 0.5 μCi of $^3$H-thymidine per well for 1 hour. Then the medium was removed, the cells were washed with saline and the DNA was precipitated by ice-cold 10% trichloroacetic acid. The precipitate was solubilized in 50 μl of IN NaOH, mixed with 4 ml of Ultima Gold® scintillation liquid (Packard) and counted on a LS 1701 "Bruker" scintillation counter.

(viii) Cellular uptake using fluorescent probes

Uptake of the conjugate compounds by cells and intracellular distribution was studied using fluorescent probes (Wells and Johnson, 1994). The fluorescent derivative of the aminoglycoside-arginine conjugate (R4K=13) was prepared by reacting the conjugate 13 with fluorescein isothiocyanate (FITC, "Sigma") in water-methanol-dimethyl sulfoxide mixture for 24 hours. FITC was added in 1:1 molar ratio to the conjugate, which enabled only one random amino group of the conjugate to react with FITC. The fluorescein-labelled conjugate was purified by extraction with acetone and absolute alcohol.

Hippocampal neurons from rat puppies were grown over rat glia cells on polylysine-coated glass cover slides. The cells were incubated in HEPES-buffered saline containing 1 mg/ml of R4K-fluorescein probe for 2 hours. The slides were washed several times with saline and studied by confocal laser-scanning microscopy on "Axiovert 100M" ("Zeiss") microscope, using excitation at 488 nm (argon-ion laser) and emission detected at 505–550 nm. The intense fluorescence, observed in the cells, indicated an efficient uptake of the probe; even higher fluorescence was detected in the cell nuclei (FIG. 4), suggesting that the R4K-fluorescein is associated with nucleic acids, as was expected. The uptake of R4K into peripheral blood mononuclear cells (PBMC) was also studied, using the same technique. Human PBMC were separated from fresh blood sample on Ficoll gradient by standard procedure. They were grown on polylysine-coated glass cover slides in RPMI medium, containing 10% fetal calf serum, for 24 hours. The cells were treated as above, R4K-fluorescein concentration was 0.1 mg/ml. As was expected, the fluorescent probe was observed in the nuclei in almost all cells (FIG. 5), indicating binding to nucleic acids.

Equine infectious anemia virus (EIAV)-infected equine dermal fibroblasts (ED) at the late stage of infection were plated on collagen-coated glass slides and incubated in HEPES-buffered saline in the presence of 10 μg/ml of FITC-labeled compounds (R4K and R3G) for 0.5–1 hour. The slides were washed several times with saline and studied by confocal laser-scanning microscopy on the Axiovert 100M (Zeiss) microscope, using 488 nm excitation (argon-ion laser) and 505–550 nm emission band.

(ix) Antiviral activity in EIAV-infected ED fibroblasts.

Both equine dermal fibroblasts (ED) and Equine Infectious Anemia Virus (EIAV), Wyoming isolate (Malmquist et al., 1973) were gifts from Profs. A. Yaniv and A. Gazit, from the Sackler Medical School of the Tel-Aviv University, Israel. ED cells were plated on plastic 6-well tissue culture plates (Nunclone) at density of 5×15 cells per well in 2 ml of DMEM/10% FCS (fetal calf serum). The medium was removed after 12–20 hours and the cells were inoculated for 2 hours with 0.5 ml DMEM/10% FCS containing 5×10$^6$ pfu (plaque forming units) of EIAV and 10 μg/ml of polybrene (hexadimetrine bromide, Sigma) (Carpenter and Chesebro, 1989). Following the incubation, another 2.5 ml of DMEM/10% FCS was added to each well. On the following day, the medium was discarded and was substituted for 2 ml of DMEM/10% FCS, containing 0.5 μCi/ml of 5,6-$^3$H uridine (Amersham). Different concentrations of the conjugates were added to the wells in duplicates. Every 34 days, 1.2 ml samples of the medium were collected and replaced with same amount of medium, containing radioactive uridine and the tested. The samples were clarified from cell debris by spinning at 12000 rpm for 5 minutes on the Eppendorf centrifuge. Viral particles from the clarified supernatants were collected by ultracentrifugation at 75000 rpm, 4° C. on the Beckman TL 100 centrifuge using TLA 100.2 rotor (Cheevers et al., 1977). The supernatants were carefully discarded and the pellet was resuspended in 200 μl of 1%

SDS/5% Tritone X-100, mixed with 1 ml Ultima Gold scintillation liquid (Packard) and counted on LS 1701 Bruker scintillation counter. Typical duration of the experiment was 15 days; EIAV growth curves in the presence of various concentrations of the conjugates in the medium were obtained. Development of the cytopathic effect (cpe) in the infected ED cells was monitored by light microscopy.

(x) Anti-HIV assay.

The HIV-1 strains NL4-3 and Ba-L and the CD4$^+$ lymphocytic cell lines SUP-T1, MT-4 and MT-2 and P4-CCR5 MAGI cells were obtained from the MRC AIDS reagent program or the NIH, AIDS Research and Reference Reagent Program.

T-tropic HIV-1 laboratory strains III$b$, 2D as well as AZT-resistant and UC781-resistant strains were utilized in this study, along with clinical isolate (clade C). HIV-1 clinical isolate, resistant to AZT is a generous gift from Dr. Mark A. Wainberg, McGill AIDS Center, McGill University, Montreal, Canada. HIV-1 laboratory strain (IIIB) resistant to UC781 was developed in vitro by increasing concentrations of UC781 to 100×IC$_{50}$ as described previously (Borkow et al., 1999).

MT-2 or MT-4 cells were cultured in RPMI 1640 supplemented with 10% fetal calf serum (FCS), 0.2 mM glutamine and penicilline/streptomycin/nistatin mixture. The cells were propagated in 96-well tissue culture plates at the density of 5×10$^4$ cells per well. Peripheral mononuclear blood cells (PMBC) were separated from whole blood samples by centrifugation in Ficoll gradient for 10 min at 400 g. PMBC were cultured in the same medium in 24-well tissue culture plates at the density of about 10$^6$ cells per well.

Anti-HIV activity and cytotoxicity measurements in MTA cells were based on viability of cells that had been infected or not infected with HIV-1 exposed to various concentrations of the test compound. The cells were infected by incubation with different titers of the HIV-1 strains for 2 hrs at 37° C. in the presence or absence of the AAC of the invention. Then the cells were washed from the virus by centrifugation at 400 g and the supernatants were discarded. The cells were resuspended in culture medium, supplemented with different concentrations of the test compounds. The cells were allowed to proliferate for 5 days, the number of viable cells was quantified by a tetrazolium-based colorimetric method (CellTiter 96® AQ$_{ueous}$ One solution Cell Proliferation Assay, Promega). Anti-HIV activity in P4-CCR5 MAGI cells was done as follows: cells (1×10$^5$/ml) were infected with 10 ng/ml of p24 antigen of HIV-1 Ba-L in the presence of varying concentrations of the test compound. 24 hours post infection, cells were washed twice with PBS and resuspended in the medium containing the appropriate drug concentration. Five days after infection the cells were washed with PBS and evaluated for β-galactosidase activity.

(xi) Flow cytometry analysis

Measurement of chemokine receptors CXCR4, CCR5 and the CD4 receptor on phytohemagglutinin (PHA)-activated PBMC was performed by flow cytometry analysis. Briefly, 0.5×10$^6$ cells were washed in ice-cold phosphate-buffered saline (PBS) and incubated for 30 minutes at 4÷C. with fluorescent labelled mAb 12G5 and 2D7 and Leu3a (Becton Dickinson, San Jose, Calif.) or with isotype control mAbs in the presence or absence of the test compound. Then, the cells were washed with ice-cold PBS and were fixed in PBS containing 1% formaldehyde. For each sample, 10,000 events were analysed in a FACScalibur™ system (Becton Dickinson). Data were acquired and analysed with CellQuest™ software (Becton Dickinson).

(xii) Measurement of intracellular calcium concentration

The intracellular calcium concentrations $[Ca^{2+}]_i$ were determined using the following procedure: SUP-T1 cells or THP-1 were loaded with Fluo-3 (Sigma, St. Louis, Mo.). Fluorescence was measured in a Fluoroskan Ascent fluorometer (Labsystems, Helsinki, Finland). Cells were first stimulated with dilution buffer (control) or test compound at different concentrations. As a second stimulus, SDF-1α (20 ng/ml) or RANTES (1 μg/ml) were used to induce $[Ca^{2+}]_i$ increase. The second stimulus was added 10 sec after the first stimulus. The compound concentration required to inhibit the $[Ca^{2+}]_i$ increase by 50% ($IC_{50[Ca2+]i}$) was calculated.

(xiii) Virus-binding assay.

MT4 cells (5×10$^5$) were incubated with supernatant containing 1×10$^5$ pg of p24 antigen of wild type HIV-1 in the presence of different concentrations of the test compound. One hour after infection, cells were washed 3 times with PBS and p24 antigen bound to the cells was determined by a commercial ELISA test (Coulter, Spain).

(xiv) Reporter gene transactivation inhibition

Transactivation inhibition is measured in HeLa cells transfected with two plasmids, HIV LTR-reporter gene construction and Tat protein expression vector. Reporter gene expression is dependent on Tat binding to TAR element while transcription from LTR promotor occurs. The level of transactivation is determined by measuring the activity of the reporter gene product by its characteristic reaction, for example, chloramphenicol acetyl transferase (CAT) acetylates chloramphenicol (Kessler and Mathews, 1992). Cell extracts containing CAT are incubated with $^{14}$C-labeled chloramphenicol in the presence of acetyl coenzyme A, extracted with ethyl acetate and resolved by thin layer chromatography (TLC). Results are observed as spots of acetylated and non-acetylated antibiotic after autoradiography of TLC plates (e.g. Calnan et al., 1991 a, b). Incubation of the cells after transfection in the presence of various concentrations of the aminoglycoside conjugate in cell culture medium and with further treatment as described above, a decrease or disappearance of acetylated chloramphenicol spots on TLC suggest inhibition of transactivation by the added conjugates.

xv) Inhibition of Tat-induced Kaposi sarcoma and endotelial cells proliferation.

Kaposi sarcoma (KS) cells, obtained from biopsy of KS lesions of AIDS patients, and human umbilical vascular endothelial cells (HUVEC) were cultured in RPMI 1640 medium supplemented with 10% FCS and conditioned medium, obtained from HTLV-II infected T-cell lymphoma culture medium as described (Salahuddin et al., 1988; Fiorelli et al., 1999). Cells are seeded at 10$^4$ cells/well in 96-well plate, coated with gelatin. After 24 hrs Tat protein (10 ng/ml-1 ng/ml), 0.5–1 μCi [$^3$H] thymidine (Amersham) and different concentrations of an AAC of the invention are added per well. Cells are harvested after 72 hrs and radioactive thymidine incorporation is measured using a beta counter.

(xvi) Crystallization trials.

Synthetic 31-nucleotide TAR RNA oligonucleotide (5'-GGC CAG AUC UGA GCC UGG GAG CUC UCU GGC C-3') containing sequence 18–44 of HIV-1 LTR, purified by PAGE and reverse-phase HPLC (Dharmacon, Inc) is used for crystallization trials. Crystallization efforts of TAR RNA will start with the use of Hampton Research crystallization screens beginning with the 48 conditions of the Natrix™ (nucleic acid sparse matrix). These involve varying of pH in the range of 5.6 to 8.5, using various polyethylene glycols, isopropanol, MPD and 1,6 hexanediol as precipitants and various mono and divalent cations as additives. An additional Hampton Research screen (nucleic acid mini screen) with MPD as precipitant, pH range of 5.5 to 7.0, polyamines as cobalt hexamine and spermine and chlorides of mono- and di-valent cations as additives, will be employed as well. Once we obtain crystals, their quality as potential X-ray diffracting candidates will be improved through minute variation of the crystallization conditions like temperature, crystallization method (sitting drops, hanging drops), speed of crystal formation and others. Nucleic acids have a built-in advantage over proteins in their ability to incorporate Br or I atoms in the 5 position of uracil. X-ray diffraction of RNA containing 5-Br uracil or 5-I uracil can provide phasing information used by the SIR (single isomorphous replacement), SIRA (single anomalous replacement) or MAD (multiple anomalous diffraction) for structure solution. Once successful crystallization conditions are established, the Br and I uracil derivatives of TAR RNA will be prepared, crystallized and subjected to X-ray diffraction collection in order to provide the phasing needed for obtaining a good electron density map.

EXAMPLE 11.

Monosaccharide conjugates with acetamidino and guanidino compounds inhibit Tat binding to TAR In order to determine which one of the side chains attached to a monosaccharide would display a better affinity to TAR RNA, several derivatives of methyl α-D-mannopyranoside (MMP), compounds 4 and 7–12, were tested for their affinity to TAR on an L-arginine-Amberlite column, and their potential inhibition of Tat binding to TAR, using the gel-shift assay as described above. The results are presented in the Table 1. The gel-shift assays (FIG. 3) demonstrated that compounds 10 and 11 inhibited the binding of 60 nM Tat R52 peptide to 6 nM TAR RNA with $CI_{50}$ values of 9 and 11 mM, respectively (Table 2). These $CI_{50}$ values were normalized to the conditions presented by Frankel et al. (Tao and Frankel, 1992), giving apparent $K_i$ values of around 1 mM, suggesting that compounds 10 and 11 are stronger inhibitors of Tat-TAR binding than the free arginine, and are similar to L-argininamide and agmatine (Tao and Frankel, 1992), and to neomycin (Zapp et al., 1993). All other monosaccharide derivatives did not show significant inhibition of Tat binding to TAR (Table 2). These results indicate that a a compound comprised of a carbohydrate "core" attached to a single strongly basic group with the geometry resembling that of guanidine, may serve as a specific inhibitor of Tat binding to TAR.

The gel-shift assay revealed that compound 12 inhibited the Tat-TAR interaction with a $CI_{50}$ of 1.8 mM which corresponds to an apparent $K_i$ of approximately 160 μM (normalized as above) (Table 2). $CI_{50}$ (or $K_i$) values (FIG. 3A and Table 2) obtained for compounds 10, 11 and 12, suggest, that not only a carbohydrate core facilitates the binding to TAR RNA of inhibitors, containing guanidinium or acetamidinium groups, but a chain, such as that of arginine, connecting the core and the charge-bearing moiety, is beneficial.

TABLE 1

Concentrations of the compounds that elute 50% of TAR RNA ($CE_{50}$) from L-arginine-Amberlite affinity column.

| Compound | $CE_{50}$, mM |
|---|---|
| Tat R52 peptide | 0.5 |
| Arginine HCl | 1500 |

TABLE 1-continued

Concentrations of the compounds that elute 50% of TAR RNA ($CE_{50}$) from L-arginine-Amberlite affinity column.

| Compound | $CE_{50}$, mM |
|---|---|
| 6-cyano MMP (4) | 1200 |
| 6-amino MMP (7) | >1500 |
| 6-amido MMP (8) | >1500 |
| 6-amidoximo MMP (9) | >1500 |
| 6-guanidino MMP (10) | 650 |
| 6-(N-acetamidino) MMP (11) | 730 |
| RMMP (12) | 310 |
| R4K (13) | 2.5 |
| R3G (14) | 1.4 |

EXAMPLE 12.

Binding of aminoglycoside-arginine conjugates to TAR RNA

The ability of aminoglycoside-arginine conjugates to bind TAR RNA using L-arginine-Amberlite affinity column is shown in Table 1. This result suggests that the aminoglycoside-arginine conjugates bind to TAR RNA with similar efficiency as the Tat peptide and compete for the same arginine-binding site on TAR.

The molecular weights of the aminoglycoside-arginine conjugates (ca 940, 1076 and 1109 Da for R3G (14), $R4GC_{1a}$ (15) and R4K (13), respectively) are close to that of the Tat R52 peptide (1434 Da), thus their binding to TAR RNA was clearly observed as electrophoretic band shifts (FIG. 3). All the conjugates displayed high affinity to TAR RNA.

TABLE 2

Concentrations of the compounds that displayed 50% inhibition ($CI_{50}$) and 50% binding ($CD_{50}$) in gel-shift experiments on TAR RNA.

| Compound | $CI_{50}$, mM | $CD_{50}$, nM | TAR RNA, nM |
|---|---|---|---|
| Tat R52 peptide | | 6–12 | 2 |
| Tat R52 peptide | | 35 | 6 |
| Tat R52 peptide | | 75 | 12 |
| Tat R52 peptide | | 200 | 20 |
| Arginine HCl | 4 | | 2 |
| Arginine HCl | 38 | | 6 |
| 6-cyano MMP (4) | 46 | | 6 |
| 6-amino MMP (7) | 56 | | 6 |
| 6-amido MMP (8) | >50 | | 6 |
| 6-amidoximo MMP (9) | >50 | | 6 |
| 6-guanidino MMP (10) | 9 | | 6 |
| 6-(N-acetamidino) MMP (11) | 11 | | 6 |
| RMMP (12) | 1.8 | | 6 |
| R4K (13) | | 2500 | 12 |
| R3G (14) | | 500 | 12 |
| $R4GC_{1a}$ (15) | | 200 | 20 |

The $CD_{50}$ of R4K (13) to 12 nM $^{32}$P-labeled TAR (in the gel-shift assay) is 2.5 μM (FIG. 3B, Table 2). The band shifts observed for the R4K (13) complex with TAR remained unchanged at increasing concentrations of R4K in the range of 1 to 5 μM. Since a Tat-TAR complex has a 1:1 stoichiometry and the band shift of R4K-TAR complex was observed to be approximately twice than that of Tat R52-TAR one (FIG. 3B), a 2:1 ratio is suggested for the R4K conjugate to RNA in the complex.

The R3G (14) conjugate displayed binding to 12 nM of TAR with a $CD_{50}$ of ca 500 nM (FIG. 3C, Table 2). The gel mobility of R3G-TAR complexes declined significantly with the increase of R3G concentration in the range of 0.5 to 4 μM, as was observed from the increase of the band shifts and an increasing precipitation of the complexes in the wells (FIG. 3C). At the same concentration of TAR (12 μM), the $CD_{50}$ of Tat R52 was found to be 75 nM (Table 2).

The $R4GC_{1a}$ (15) conjugate formed a complex with 20 nM of TAR RNA at concentrations starting from 200 nM. The $CD_{50}$ of Tat R52 at the same concentration of TAR RNA was 200 nM. By comparing the gel shift of $R4GC_{1a}$ (15) -TAR to that of Tat R52, it is suggested that the ratio of $R4GC_{1a}$ to the RNA in the complex is 1:1 (FIG. 3D, Table 2). An approximate linear dependence of Tat R52 $CD_{50}$ values on TAR RNA concentrations was observed (Table 2). We have normalized the $CD_{50}$ values obtained in our experiments to the reported conditions (Calnan et al., 1991 b), and apparent $K_d$ values, suitable for comparison with reported data are available. The apparent $K_d$ values for the conjugate complexes with TAR RNA were found to be 416 nM for R4K, 83 nM for R3G, and approximately 20 nM for $R4GC_{1a}$. Thus, a trisaccharide core bearing three or four arginine residues can successfully mimic the binding pattern of Tat.

EXAMPLE 13.

Figure 4A:
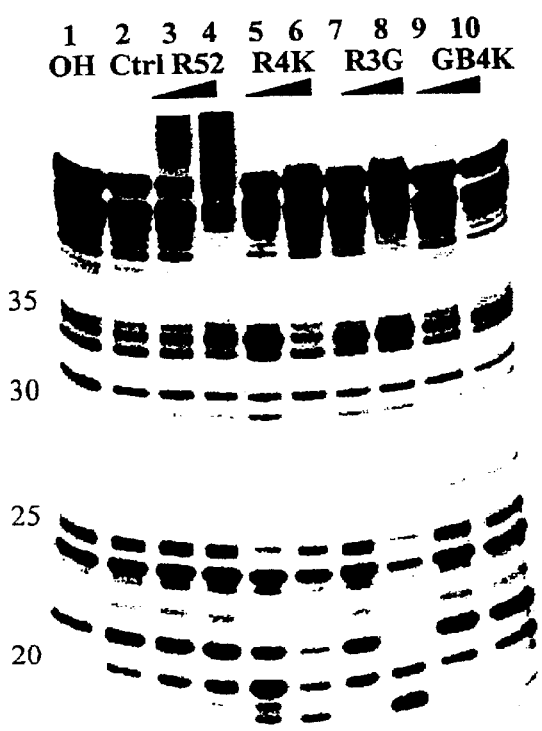
FIGS. 4A–4C present footprinting studies of the binding sites of aminoglycoside-arginine conjugates of the invention on TAR RNA. Approximately 100 nM 5'$^{32}$P end-labeled TAR was used per lane. Lane "OH" represents alkaline hydrolysis of TAR. Concentrations: Tat R52 peptide: 2 to 4 μM (lanes 3, 4); R4K (compound 13): 10 to 20 μM (lanes 5, 6); R3G (compound 14): 4 to 8 μM (lanes 7, 8); GB4K (compound 19): 20 to 40 μM (lanes 9, 10). (4A) RNase A footprinting. Lane "ctrl" represents RNase cleavage in the absence of the binders. (4B) Uranyl photocleavage. The reactions were performed in cacodylate buffer pH 6.5 (slightly acidic conditions modulate the uranyl cleavage, reflecting the conformational changes of nucleic acids). The samples were irradiated for 10 min at 420 nm. Lane "ctrl" represents uranyl photocleavage in the absence of the binders. (4C) Lead acetate footprinting. Lane "ctrl" represents lead acetate cleavage in the absence of the binders. The gels were analysed using Storm 820 phosphoimager, quantitations were obtained using ImageQuant program.
Figure 4B:
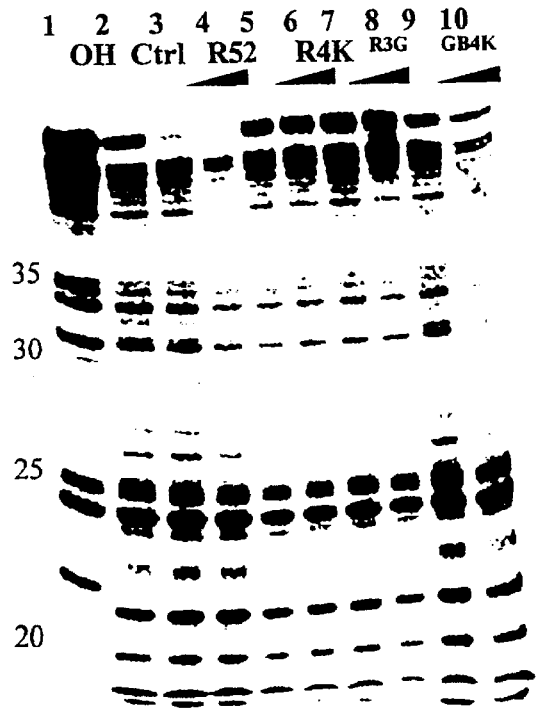

Determination of the conjugates' binding sites on TAR RNA a. RNase A footprinting TAR RNA and RNase A concentrations were established by co-titration. To produce a "single-hit" kinetics conditions, 1 μM TAR versus 200 pM RNase A were selected. Tat R52 and AAC concentrations were determined by titration. Effective protection of 1 μM TAR was observed with 2 μM Tat R52, 10 μM of R4K and 4 μM R3G. GB4K did not exhibit binding to TAR RNA, neither in gel-shift experiments (up to 50 μM) nor in the protection experiments (at 40 μM). RNase A cleaved TAR RNA in an uneven manner (FIG. 4A., lane 2). The most susceptible regions for cleavage were the single-stranded loop, nucleotides U31–G34 as well as C24 and U25 of the bulge. Strong cleavage was also observed at G21–G41 and A20–U42 pairs (lower stem). Binding of R52 (2–4 μM) caused a weakening of the bands in the upper stem region, (G26-C39, A27-C38, as well as U40) (FIG. 4A., lanes 3, 4). At 4 μM R52, the cleavage at G34 (loop) was enhanced, as well as a certain enhancement of bands A20, G21, U23 and U25 was observed. Remarkably, the band corresponding to the R52-TAR complex still was observed on the gels even after electrophoresis under strongly denaturing conditions. In the presence of R4K (10–20 μM), the upper stem (G26-C29), the lower stem and the bulge (G21-U23, partially C24 and U25) were protected as well as C38, C39 and U40. Cleavage at C19 and A20 of the lower stem and C30, G33 and G34 of the loop was enhanced by 10 μM R4K, whereas with 20 μM R4K the protection of C30, G34 and A20–G21 was observed (FIG. 4A., lanes 5, 6). R3G (4–8 μM) displayed similar behavior; protection of the lower stem and the bulge was more pronounced with 8 μM R3G than with 20 μM R4K. Cleavages at C19-A20 in the lower stem as well as at G30 and G34 in the loop were observed (FIG. 4A., lanes 7, 8). In the presence of GB4K (20 μM) no significant protection was observed. With 40 μM GB4K, U25 (bulge), U31, G33, A35 (loop) as well as nucleotides 37–42 were partially protected, whereas the bands of A20, C30 and G34 were partially enhanced (FIG. 4A., lanes 9, 10).

b. Uranyl nitrate photoprobing of TAR RNA $UO_2^{++}$ has high affinity to DNA and RNA backbone phosphates. Irradiation of the uranyl-nucleic acid complex with light, at a wavelength of 420 nm leads to the oxidation of a proximal deoxyribose/ribose ring, resulting in a cleavage of the backbone (Nielsen et al., 1992). Slightly acidic conditions (pH 6.5 and lower) modulate the uranyl cleavage, reflecting the conformational changes of nucleic acids. For probing the conjugates' interactions with TAR RNA, the best results were obtained in cacodylate buffer pH 6.5, 25–50 μM uranyl nitrate and 10–20 min irradiation. 1 μM TAR was cleaved by 50 μM uranyl nitrate after 10 min irradiation, in an uneven manner. Nucleotides of the lower stem (C18–G21 and U40) and of the loop (U31 and G33) were better cleaved by the uranyl cation than those of the upper stem (G26-C29). The bulge (U25 and C24) was hypersensitive to cleavage (FIG. 4B., lane 2).

Figure 4C:
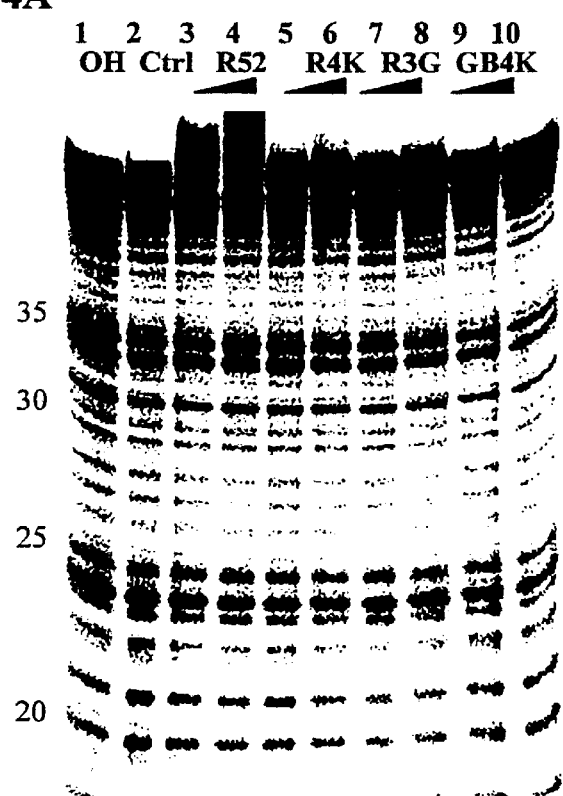

In the presence of Tat R52 (4 μM), protection of the loop and the upper stem (A27–A35) as well as U38-G44 (the opposite strand) was observed, but no changes were observed in the bulge region. Cleavage at C18 and G21 was enhanced (FIG. 4B., lanes 3, 4). With 10–20 μM R4K (FIG. 4B., lanes 5, 6) and 4–8 μM R3G (FIG. 4B., lanes 7, 8) the whole TAR RNA molecule appeared protected against cleavage. GB4K (20 μM), under the same conditions, did not affect TAR RNA uranyl photocleavage (FIG. 4B., lanes 9). 40 μM GB4K displayed protection of the upper stem (A27–C29), C39–G44 of the opposite strand and the loop (C30-A35).

c. Lead acetate footprinting $Pb^{++}$ cations cause cleavage predominantly of phosphoester bonds of RNA single-stranded regions. Cleavage also may occur in double-stranded regions if they contain weak, bulged or destabilized base pairs (Wallis et al., 1997). Lead acetate footprinting was found to be a suitable and accurate method for the studies of AAC binding to TAR. In the presence of R52, A22–U40 and G26C39 pairs were protected as well as C19, A20, A27 and G28 (FIG. 4C, lanes 3, 4). Protection was also observed at G33 and G34 of the loop. In the presence of AAC, the protection of the bulge region with flanking base pairs was observed, along with some protection at G34 of the loop (FIG. 4C, lanes 5–8).

EXAMPLE 14.

Specificity of binding of aminoglycoside-arginine conjugates to TAR RNA.

Figure 6:
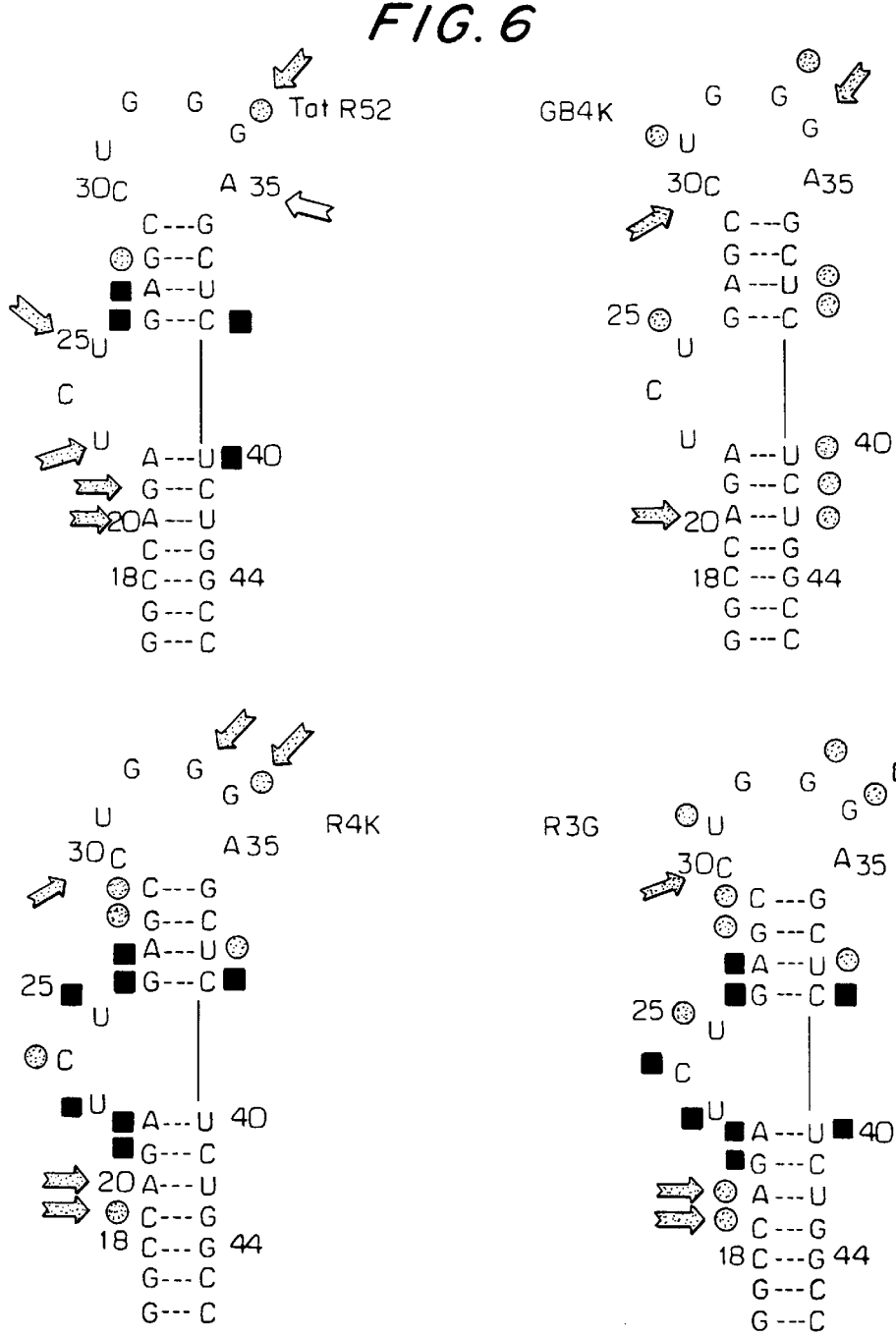
FIG. 6 is a schematic representation of Tat R52, R4K, R3G (compound 14) and GB4K binding sites on TAR RNA. The results indicate that more than one molecule of R4K and R3G bind per one molecule of TAR. High affinity binding site, similar to that of Tat R52, is located in the bulge region. Low affinity binding site is assigned to loop-stem junction.

Binding of R3G and R4K to a variety of short RNA oligonucleotides, including $rG_{15}$, $rG_{15}$-$rC_{15}$ duplex and truncated TAR RNA sequences, was tested by gel-shifts. The conjugates did not display any binding to these RNAs in the micromolar concentration range (data not shown). Binding competition experiments were performed with $^{32}P$ labeled TAR RNA in the presence of various amounts of unlabeled yeast tRNA (Sigma). In gel-shift experiments, a ten-fold excess of tRNA did not inhibit complex formation between TAR and R52 or the conjugates (FIGS. 7A, 7B) A hundred-fold excess of tRNA inhibited complex formations (over 90% inhibition, data not shown). This demonstrates similar specificity of the binding of Tat R52 and AAC to TAR RNA. In the "single-hit" RNase A footprinting, the presence of a ten-fold excess of yeast tRNA in the reaction mixtures did not affect the protection pattern significantly. However, a trend of AAC binding inhibition to definite positions on TAR under these conditions was quite obvious (FIG. 7C). Densitometry quantitations, as described above, showed these positions to be G21–U25, G28 and U38 (FIGS. 7D, 7E). Positions not affected by tRNA excess resemble Tat R52 binding site (FIG. 6, FIG. 7E).

EXAMPLE 15.

Binding sites of AACs of the invention on TAR RNA.

Gels were analyzed by densitometry using a "Storm 820" phosphoimager, and the intensities of the bands were determined by the ImageQuant program. The results of the measurements are presented in FIG. 5 as the relative intensity of each band to the respective control band. Zero line stands for the abscence of any effect (within 10% experimental error), positive peaks denote protection of the nucleotide from cleavage and negative peaks represent cleavage enhancement (by RNase A) at certain positions due to conformational changes of TAR RNA. From these graphs, the binding sites for R52 and AAC were derived (FIG. 6).

Based on the footprinting results (FIGS. 4–6), we can suggest that R52 makes contacts with TAR at the G26-C39 pair, the base-pair that was determined to be crucial for TAR major groove recognition by ligands (Gelus et al, 1999); contacts with A27, G28 and G40 were also assigned. The whole region between the bulge and the loop acquires a certain buried conformation (as can be concluded from uranyl footprinting results). Binding of R52 causes conformational changes in the bulge, making U23 and U25, as well as A20 and G21 more accessible to RNase A cleavage. In the loop, G34 and A35 become more exposed to RNase digestion, whereas in uranyl and lead footprinting experiments, G34 is found to be protected. G34-G33, shown later on, is a metal-binding site. The results of our footprinting experiments suggest that the binding site for R52 (FIG. 6) is similar to that for Tat peptide and in accordance to a model of Tat peptide-TAR RNA complex (Seewald et al., 1998).

The binding of an AAC of the invention to TAR differs significantly from R52 binding, while R4K and R3G bind similarly to TAR (FIGS. 4–6). The contacts with TAR can be assigned at the A22–U40, G26-C39 and A27–U38 pairs (A27 with R4K) as well as at G21. The whole bulge region in each case is involved in the binding. C19 and A20 (with R3G) are protected in $UO_2^{++}$ and $Pb^{++}$ footprinting experiments, while they are readily cleaved by RNase A. C30, U31(only with R3G), G33 (only with R4K) and G34 are more exposed to RNase A digestion upon AAC binding, whereas in uranyl and lead footprinting, there is protection at G34 with both compounds. This behavior resembles R52 binding to TAR. Molecular weights of AAC are smaller then of R52, and, assuming R52 is folded as β-hairpin, similarly to the described model of Tat basic nonapeptide bound to TAR (Seewald et al., 1998), we can suggest that an AAC occupy approximately ⅔ of the peptide molecular volume. AAC makes more contacts with TAR than R52 (FIG. 6); thus it is plausible that there are two molecules of AAC in the complex with TAR RNA. This suggestion is supported by the gel-shifts and the fact that the whole TAR RNA molecule in the presence of AAC is protected against $UO_2^{++}$ cleavage (uranyl footprinting under our conditions reflects conformational changes in RNA). In contrast, upon R52 binding, only the upper stem part of TAR is protected. There is a certain similarity in AAC protection of TAR RNA to that of neomycin B, which protects the C19–G43 and A22–U40 pairs of the lower stem, U23 and U25 of the bulge and G26 of the upper stem (Wang et al., 1998). Thus, we can conclude that an AAC of the invention possesses both aminoglycoside-like and peptide-like features of binding to TAR. We suggest that one of the AAC molecules binds in the lower stem-bulge region, whereas the second one binds in the upper stem, similarly to R52, but inducing different conformational changes in the TAR RNA loop (FIG. 6).

It was unexpected that GB4K, which is very similar to R4K, differs so drastically in TAR RNA binding. GB4K is a very weak TAR RNA binder and presumably forms only non-specific electrostatic contacts with TAR. Nevertheless, in the presence of GB4K, U38–U42 are found to be protected as well as U25, U31 and G33. Conformational changes upon GB4K binding in TAR, similarly to AAC, induce cleavages by RNase A at A20, C30 and G34, which is probably a general feature of binding of this class of ligands to TAR RNA (FIG. 6). We conclude that in the context of aminoglycoside-based peptidomimetic TAR binders, not any guanidine bearing side-chains are suitable for the efficient recognition; so far only arginine residues were properly recognized by TAR RNA. It is worth noting that streptomycin, bearing two guanidino groups on the deoxystreptamine ring, binds to TAR (Wang et al., 1998), but is not an efficient inhibitor of the Tat-TAR interaction (Mei et al., 1995). We suggest that the α-amino groups of the conjugated arginine moieties are essential for this interaction.

Figure 7A:
FIGS. 7A–7E show the effect of yeast tRNA on TAR RNA band shifts and RNase A footprinting in the presence of Tat R52, R3G and R4K. 7A. Band shifts of TAR RNA induced by binding of R4K and R3G (reproduced from FIG. 3). 20 μl samples containing 10–12 nM $^{32}$P-labeled TAR RNA and 1–5 μM R4K or 0.5–4 μM R3G in 10 mM Tris-HCl (pH 7.5) buffer, containing 70 mM NaCl, 0.2 mM EDTA and 5% glycerol, were incubated for 10 minutes at 0° C. Following the incubation, the samples were analyzed by electrophoresis on 10% native polyacrylamide gel (40:1). Gels were dried and visualized by autoradiography. R4K (left) forms 2:1 complexes with TAR RNA. R3G (right) forms complexes of increased molecular weight, and caused precipitation of TAR RNA in the wells (not shown).
Figure 7B:
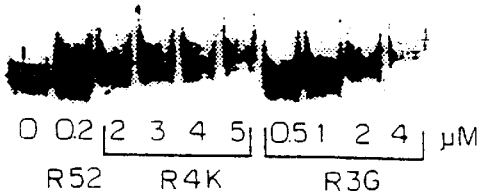
Figure 7C:
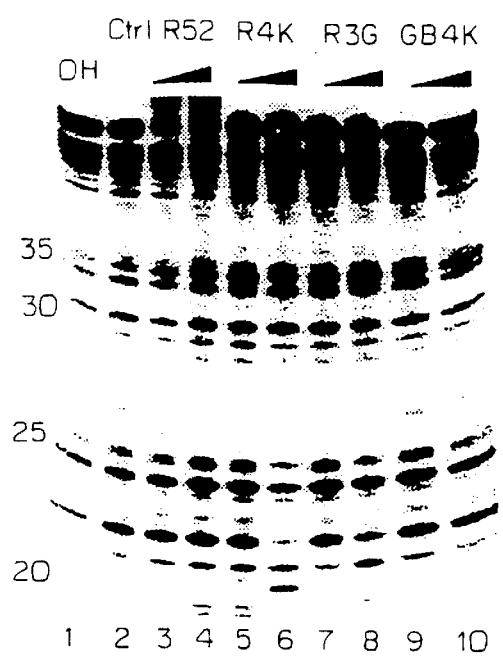
Figure 7D:
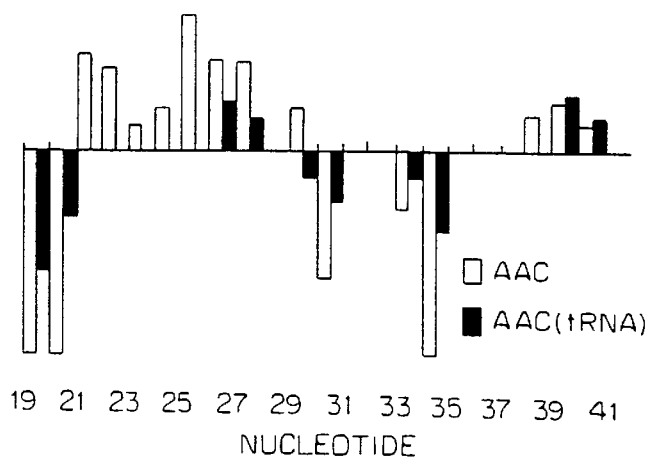
Figure 7E:
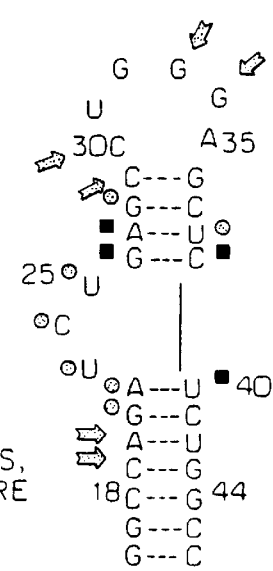

Previously, we suggested that TAR forms the complex with two molecules of R4K (FIGS. 3B, 7A,). The difference in band shifts in the presence of tRNA (FIG. 7B) may indicate that the TAR-R4K complex, under this condition, contains only one molecule of R4K. The same may be true for the R3G-TAR complex, whose band shifts are more complicated for interpretation, since R3G is a mixture of isomers. These observations support our suggestion that R4K and R3G bind to at least two sites on TAR RNA, which are different in affinity. These sites could be distinguished by RNase A footprinting in the presence of an excess of tRNA. The AAC protection pattern in the presence of tRNA tends to be similar to that of R52, while the protection of G21–U25 was inhibited (FIG. 7D). The site with higher affinity involves the bulge and the flanking base pairs, similar to the Tat peptide (like R52) binding site, while the low affinity site is in the lower stem-bulge region, similar to neomycin B binding site (FIG. 7E, FIG. 12). It is worth noting that 1D NMR spectra taken at different ratios of R4K to TAR suggest that R4K preferentially binds first to one, then to the second site on TAR (in collaboration with Professor T. L. James, UCSF, unpublished results).

EXAMPLE 16.

Cytotoxicity measurements

All the compounds were tested for their toxicity in the HeLa, LAN-1 and ED cell lines. None of the compounds up to concentrations of 1 mM caused any cell growth inhibition, as measured by $^3$H-thymidine incorporation.

EXAMPLE 17.

Intracellular accumulation and distribution of fluorescent-labelled conjugates.

An R4K fluorescent derivative (R4K-fluorescein) was prepared and its uptake by rat neurons (FIG. 9) and human peripheral blood mononuclear cells (FIG. 10) was demonstrated. Similar experiments were performed using equine dermal fibroblasts (ED cells), both uninfected and infected with EIAV. After 30–60 min incubation with 10 μg/ml of either R4K-FITC or R3G-FITC, an intense fluorescence was observed in the cell nuclei (FIGS. 11B, 11D). This indicates that the conjugates efficiently penetrate into the ED cell nuclei of uninfected as well as EIAV-infected cells.

EXAMPLE 18.

Antiviral activity of R3G and R4K conjugates.

18 a. EIAV-infected ED cells.

Equine infectious anemia virus (EIAV) of Wyoming strain is adapted to grow in equine dermal fibroblasts (ED), without damaging them with a titer of 1 μfu per cell (Malmquist virus). We used a significantly higher infection level (superinfection), around 10 pfu per cell, in order to accelerate the viral growth and to cause the development of the EIAV-induced cytopathic effect (cpe) in the cells at the late stage of the infection. In the absence of inhibitors, EIAV proliferated in the ED cells reaching a plato 9–12 days after infection (FIG. 8). After 15 to 17 days, the viral titer in the medium dropped and the cells appeared as cpe phenotype (FIG. 8C): cell nuclei were condensed, vacuoles were observed in the cytoplasm and the cells formed syncytia. Development of cpe started 10–12 days after infection, reaching a maximum on days 15–17, followed by rapid cell death and exfoliation from the plastic bottom of the well.

Addition of 50–100 μM of R4K and 12.5–50 μM of R3G to the EIAV-infected cells caused a significant (3–5 fold) inhibition of the viral growth in a dose-dependent manner (FIG. 8). After day 12, a slight increase of the EIAV titer was observed. GB4K (100–250 μM) did not show any effect on the viral growth. Toxicity of the conjugates for ED cells was tested by $^3$H-thymidine incorporation as described above. The compounds, up to 1 μM, concentration did not inhibit DNA synthesis in the cells.

A noticeable inhibition of the cpe development was observed at 25 and 50 μM R3G, even after 13–15 days (FIGS. 8C, 8D). Untreated cells at the same time displayed cpe development, whereas cell treated by R3G preserved normal phenotype. This observation correlates with the viral production. Moreover, when R3G was added to the infected cells during the cpe onset (day 12–13), at day 15 the development of cpe was inhibited and cell damage was not noticeable. The viral titer decreased at least twice compared to control. At the same time, untreated cells developed massive cpe phenotype and were significantly damaged by day 15 (data not shown).

18 b. HIV-infected human cells.

The activity of AACs of the invention against HIV-1 NL4-3, RF, and NL4-3 AMD3100-resistant T-tropic strains, T-tropic HIV-1 AZT-resistant clinical isolate AOM as well as M-tropic HIV-1 Ba-L strain are presented in Table 3.

The 50 % cytotoxic concentrations ($CC_{50}$) were found to be >1130 μM for R4K and >3940 μM for R3G. R3G and R4K inhibited HIV-1 NL3-4 proliferation at 50% effective concentrations ($EC_{50}$) of 15 μM and 31 μM, respectively. The chemokine stromal-derived factor SDF-1α was active against HIV-1 NL4-3 at $EC_{50}$ of 0.04 μM.

R3G was active against T-tropic HIV-1 RF strain and AOM clinical isolate as well as M-tropic HIV-1 Ba-L strain at $EC_{50}$ of 16–35 μM.

The NL4-3 AMD3100-resistant virus was cross-resistant to SDF-1α (>25-fold) to R4K (>4-fold) and R3G (>9-fold), suggesting that these compounds share a similar mode of action.

TABLE 3

Anti-HIV-1 activity of the AAC, AZT and the CXC-chemokine SDF-1α.

| | $EC_{50}^a$ (μM) | | | | | |
|---|---|---|---|---|---|---|
| | | | | HIV-1 | | |
| | HIV-1 | HIV-1 | HIV-1 | AMD | HIV-1 | $CC_{50}^b$ |
| Compound | NL4-3 | RF | AOM | 3100res | Ba-L$^c$ | (μM) |
| R4K | 31 | >113 | 67 | >113 | >113 | 1130 |
| R3G | 15 | 35 | 16 | >133 | 29 | >3940 |
| SDF-1α | 0.04 | — | — | >1 | — | >0.1 |
| AZT | 0.01 | 0.02 | 3.7 | 0.005 | 0.2 | >7.5 |

$^a$$EC_{50}$: 50% effective concentration, or concentration of the compound required to inhibit HIV-1 replication by 50%, as measured by the MTT assay.
$^b$$CC_{50}$: 50% cytotoxic concentration, or concentration of the compound required to reduce the viability of MT-4 cells, as measured by the MTT assay.
$^c$$EC_{50}$: 50% effective concentration, or concentration of the compound required to inhibit HIV-1 replication by 50%, as measured by β-galactosidase activity in P4-CCR5 cells infected with the HIV-1 Ba-L strain.

The toxicity of the conjugates R3G and NeoR to MT-2 cells as well as PMBC lines ETH, derived from Ethiopian blood sample and IS, derived from Israeli blood sample (healthy controls) was determined after 2 days incubation of the cells in the presence of the conjugates. 50% cytotoxic concentrations ($CC_{50}$) of the conjugates were determined to be >500 μM for R3G and 250 μM for NeoR (Table 4). The activity of the AAC against HIV-1 IIIb and 2D laboratory strains as well as against AZT resistant, UC781 resistant HIV-1 strains and clade C HIV-1 clinical isolate, are presented in Table 4. The 50% effective concentrations ($EC_{50}$) of R3G and NeoR were 6–10 μM and 3–4 μM, respectively.

TABLE 4

Anti-HIV-1 activity of AAC.

| Compound | HIV-1 IIIB | HIV-1 2D | HIV-1 AZTres$^a$ | HIV-1 UC781res$^b$ | HIV-1 Clade C$^c$ | $CC_{50}$ (μM)$^e$ | $TI_{50}^f$ |
|---|---|---|---|---|---|---|---|
| | | | $EC_{50}$ (μM)$^d$ | | | | |
| R3G | 10 | 10 | 8 | 6 | 6 | 500 | 50–85 |
| NeoR | 3 | 4 | 3 | 3 | 3 | 250 | 60–85 |

$^a$HIV-1 clinical isolate, resistant to AZT.
$^b$HIV-1 laboratory strain (IIIB) resistant to UC781.
$^c$HIV-1 clinical isolate (clade C).
$^d$The 50% effective concentration. Inhibition of HIV-1 replication was determined by assessing syncytium formation and by a tetrazolium based colorimetric assay (CellTiter 96 ® Aq$_{ueous}$ One solution Cell Proliferation Assay, Promega). The data is the average of two independent experiments done in duplicates.
$^e$The 50% cytotoxic concentration was determined by a tetrazolium based colorimetric assay as in $^d$ above. The data is the average of two independent experiments done in duplicates.
$^f$The 50% in vitro therapeutic index (ratio $CC_{50}/EC_{50}$).

MT-2 cells were infected with different dilutions of HIV-1 clade C or 2D strains (1: 1 to 1:16) and incubated for 4 days with 10–20 μM R3G or 5–10 μM NeoR (FIG. 13). Cells infected with HIV-1 clade C developed more than 50% cpe, whereas cells infected with 2D strain developed only around 25% cpe at the same period of time. The efficacy of the AAC of the invention is significantly increased with viral dilutions. At earlier stage of infection (2D strain, 25% cpe) the inhibition by the AAC was significantly more pronounced than at later stage of the infection (clade C, >50% cpe).

To determine the effect of the AAC of the invention on viral infectivity, the infection of MT-2 cells by HIV-1 was performed in the presence and absence of 20 μM R3G or 10 μM NeoR (FIG. 14). When the cells were infected with HIV-1 clade C in the presence of the AAC and then incubated for 3 days in the absence of the AAC (reaching 25% cpe), the virus growth was inhibited by 30% for R3G and 60% for NeoR (FIG. 14). Presence of the AAC during infection depressed viral proliferation. When the cells were incubated with the AAC after the infection, the antiviral effect of the conjugates was significantly increased (FIG. 14).

The effect of the AAC in the presence of AZT was tested in HIV-1 2D and clade C. The antiviral effect of both R3G and NeoR seems to be additive to that of AZT (FIG. 15). Interaction with chemokine receptors.

In order to elucidate whether the anti-HIV activity of aminoglycoside-arginine conjugates is due to their interaction with CXCR4, we have tested their capacity to inhibit the binding of a mAb to CXCR4 (12G5). SDF-1α, the natural ligand of CXCR4, was used for comparison. Table 5 shows the concentrations of 50% inhibition ($IC_{50}$) of 12G5 mAb binding ($IC_{50-12G5}$) by R3G, R4K, NeoR and SDF-1α. The conjugates R3G, R4K and NeoR showed high affinity for CXCR4 (as measured by the inhibition of 12G5 binding to SUP-T1 cells or PMBC) which is consistent with their anti-HIV activity. None of the compounds inhibited the binding of 2D7, a monoclonal antibody directed to CCR5 or an anti-CD4 antibody (Leu3a) in IL-2/PHA-stimulated PBMC.

TABLE 5

Inhibition of anti-CXCR4 mAb (12G5) binding to CXCR4+ cells

| Compound | $IC_{50-12G5}$[a] (μM) SUP-T1 cells | PMBC |
|---|---|---|
| R4K | 3.7 | 2.2 |
| R3G | 7.7 | 2.7 |
| NeoR | — | 2.4 |
| SDF-1α | 0.013 | — |

[a]$IC_{50-12G5}$: 50% inhibitory concentration, or concentration of the compound required to inhibit by 50% the binding of 12G5 mAb to CXCR4+ cells.
—: not tested.

We have found that in the presence of 5 μM NeoR, the binding of anti-CXCR4 monoclonal antibody (mAb) 12G5 to PHA-activated PMBC was suppressed significantly more than in the presence of 5 μM R3G (FIG. 16A). The effect of NeoR (5 μM) on binding of 12G5 mAb to CXCR4 is presented in FIG. 16B. The effect of R3G (25 μg/ml) and R4K (25 μg/ml) on the binding of 2D7 mAb to CCR5, 12G5 mAb to CXCR4 and Leu3a mAb to CD4 in PHA-stimulated PBMC is presented in FIG. 17.

To further evaluate the interaction of aminoglycoside-arginine conjugates with CXCR4, we tested the capacity of SDF-1α to induce an intracellular $Ca^{2+}$ signal in the presence of these conjugates. Both R3G and R4K inhibited the SDF-1α-dependent $Ca^{2+}$ signal in a dose dependent manner (FIG. 18). R3G and R4K did not inhibit the intracellular $Ca^{2+}$ signal induced by RANTES in THP-1, CCR5+ cells (data not shown).

Inhibition of virus binding to CD4+ cells.

Our experiments showed that R4K and R3G inhibit the binding of HIV-1 NL4-3 to MT-4 cells in a dose dependent manner. Dextran sulfate was also active, while SDF-1α at the concentration of 0.5 μg/ml did not inhibit the binding of HIV-1 to MT-4 cells (FIG. 19). Similarly, R4K and R3G inhibited the binding of the R5 strain Ba-L to MT-4 cells in a dose dependent manner (data not shown)

REFERENCES

1. Albini, A., Ferrini, S., Benelli, R., Sforzoni, S., Guincuiglio, D., Aluigi, M. G., Proundfoot A. E. I., Alouani, S., Wells, T. N. C., Mariani, G., Rabin, R. L., Farber, J. M., and Noonan, D. M. (1998) *Proc. Natl. Acad. Sci. USA* 95, 13153–13158.
2. Arakaki R, Tamamura H, Premanathan M, Kanbara K, Ramanan S, Mochizuki K, Baba M, Fujii N, and Nakashima H. (1999) *J Virol* 73, 1719–1723.
3. Aboul-Ela, F., Karn, J., Varani, G. (1995) *J. Mol. Biol.* 253, 313–332.
4. Aboul-Ela, F., Karn, J., and Varani, G. (1996) *Nucleic Acids Res.* 24, 3974–3981.
5. Barillari, G., Sgadari, C., Palladino, C., Gendelman, R., Caputo, A., Morris, C. B., Nair, B. C., Markham, P., Nel, A., Sturzl, M., and Ensoli, B. (1999) *J. Immunol.* 163, 1929–1935.
6. Benelli, R., Mortarini, R., Anichini, A., Guincuiglio, D., Noonan, D. M., Montalti, S., Tacchetti, C., and Albini, A. (1998)*AIDS* 12, 261–268.
7. Berger, E. A., Murphy, P. M., and Farber, J. M. (1999) *Annu. Rev. Immunol.* 17, 657–700.
8. Borkow, G., Arion, D., Wainberg, M. A., Parniak, M. A. (1999), *Antimicrob. Agents Chemother.* 43, 259–263
9. Boykins, R. A., Mahieux, R., Shankavaram, U. T., Gho, Y. S., Lee, S. F., Hewlett, I. K., Wahl, L. M., Kleinman, H. K., Brady, J. N., Yamada, K. M., and Dhawan, S. (1999) *J. Immunol.* 163, 15–20.
10. Calnan, B. J., Biancalana, S., Hudson, D., Frankel, A. D. (1991 a) *Genes Dev* 5, 201–210.
11. Calnan, B. J., Tidor, B., Biancalana, S., Hudson, D., Frankel, A. D. (1991 b) *Science* 252, 1167–1171.
12. Carpenter, S., and Chesebro, B. (1989) *J. Virol.* 63, 2492–2496.
13. Cheevers, W. P., Archer, B. G., and Crawford, T. B. (1977) *J Virol.* 24, 489–497.
14. Churcher, M. J., Lamont, C., Hamy, F., Dingwall, C., Green, S. M., Lowe, A. D., Butler P. J. G., Gait, M. J., Karn, J. (1993) *J. Mol. Biol.* 230, 90–110.
15. Cooper, D. J., Ydis, M. D., Marigliano, H. M., Traubel, T. (1971) *J.Chem.Soc.* C60, 2876–2888.
16. Cordingley, M. G., LaFemina, R. L., Callahan, P. L., Condra J. H., Sardana, V. V., Graham, D. J., Nguyen, T. M., LeGrow, K., Gotlib, L., Schalabach, A. J., and Colonno, R. J. (1990) *Proc.Natl.Acad.Sci. USA* 87, 8985–8989.
17. Delling, U., Reid, L. S., Barnett, R. W., Ma, M. Y.-X., Climie, S., Sumner-Smith, M. and Sonnenberg, N. (1 992) *J. Virol.* 66, 3018–3025.
18. Doranz B J, Grovit-Ferbas K, Sharron M P, Mao S H, Goetz M B, Daar E S, Doms R W, and O'Brien W A. (1997) *J Exp Med* 186, 1395–1400.
19. Este J. A,., Cabrera, C., de Clercq, E., Struyf, S., van Damme, J., Bridger, G., Skerlj, R. T., Abrams, M. J., Henson, G., Gutierrez, A., Clotet, B., and Schols D. (1999) *Mol Pharm* 55, 67–73.
20. Fiorelli, V., Barillari, G., Toschi, E., Sgadari, C., Monini, P., Sturzl M., Ensoli, B.(1999). *J. Immunol.* 162, 1165–1170.

21. Fourmy, D., Yoshizawa, S., and Puglisi, J. D. (1998 a) *J. Mol. Biol.* 277, 333–345.
22. Fourmy, D., Recht, M. I., and Puglisi, J. D. (1998 b) *J. Mol. Biol.* 277, 347–362
23. Gait, M. J., and Karn, J. (1995) *Trends Biotech.* 13, 430–438.
24. Geiger, A. et al. (1996) *Nucl.Acid Res.* 24, 1029–1038.
25. Gelus, N., Hamy, F., and Bailly, C. (1999) *Bioorg Med Chem* 6, 1075–1079.
26. Hamy, F., Felder, E. R., Heizmann, G., Lazdins, J., Aboul-Ela, F., Varani, G., Karn, J., and Klimkait, T. (1997) *Proc.Natl.Acad.Sci. USA* 94, 3548–3553.
27. Huang, L., Bosch, I., Hofmann, W., Sodorski, J., and Pardee, A. B. (1998) *J. Virol.* 72, 8952–8960.
28. Huq, I., Wang, X., and Rana, T. M. (1997) *Nature Struct. Biol.* 4, 881–882.
29. Huq, I., Ping, Y.-H., Tamilarasu, N., Rana, T. M. (1999) *Biochemistry* 38, 5172–5177.
30. Kessler, M., Mathews, M. B. (1992) *J.Virol.* 66, 4488–4501.
31. Kundrot, C. E. (1997) *Methods in Enzymology* 276, 143–157.
32. Malmquist, W. A., Barnett, D., and Becvar, C. S. (1973) *Arch. Gesamte Virusforsch.* 42, 361–370.
33. Mei, H-Y., Galan, A. A., Halim, N. S., Mack, D. P., Moreland, D. W., Sanders, K. B., Truong, H. N., and Czarnik, A. W. (1995) *Bioorg.Med.Chem.Letts.* 5, 2755–2760.
34. Mei, H.-Y., Mei, C., Heldsinger, A., Lemrow, S. M., Loo, J. A., Sannes-Lowery K. A., Sharmeen, L., and Czarnik A. W. (1998) *Biochemistry* 37, 14204–14212.
35. Mujeeb, A., Parslow, T. G., Yuan, Y. C., and James, T. L. (1996) *J. Biomol. Struct. Dyn.* 13, 649–661.
36. Murakami T, Nakajima T, Koyanagi Y, Tachibana K, Fujii N, Tamamura H, Yoshida N, Waki M, Matsumoto A, Yoshie O, Kishimoto T, Yamamoto N, and Nagasawa T. (1997). *J Exp Med* 186, 1389–1393.
37. Nielsen, P. E., Hiort, C., Sonnichsen, S. H., Buchard, O., Dahl, O., and Norden, B. (1992) *J. Am. Chem. Soc.* 114, 4967–4975.
38. O'Brien, W. A., Sumner-Smith, M., Mao S.-H., Sadeghi, S., Zhao, J.-Q., and Chen, I. S. Y. (1996) *J. Virol.* 70, 2825–2831.
39. Pinner, D. (1883) *Berichte.* 16, 1654.
40. Puglisi, J. D., Chen, L., Blanchard, S., Frankel, A. D. (1995) *Science* 270, 1200–1203.
41. Puglisi, J. D., Chen, L., Frankel, A. D., Williamson, J. R. (1993) *Proc. Natl. Acad. Sci. USA* 90, 3680–3684.
42. Puglisi, J. D., Tan, R., Calnan, B. J., Frankel, A. D., Williamson, J. R. (1992) *Science* 257, 76–80.
43. Rana, T. M., and Jeang K.-T. (1999) *Archives Biochem. Biophys.* 365, 175–185.
44. Roy, S., Deling, U., Chen, C. H., Rosen, C. A., Sonnenberg, N. (1990) *Genes Dev* 4, 1365–1373.
45. Scaringe, S. A., Wincott, F. E., and Caruthers, M. H. (1998) *J. Am. Chem. Soc.*120, 11820–11821.
46. Salahuddin, S. Z., Nakamura, S., Biberfield, P., Kaplan, M. H., Markham, P. D., Larsson, L., Gallo, R. C. (1988) *Science* 242, 430–433.
47. Simmons G, Clapham P R, Picard L, Offord R E, Rosenkilde M M, Schwartz T W, Buser R, Wells T N C, and Proudfoot A E. (1997) *Science* 276, 276–279.
48. Seewald, M. J., Metzger, A. U., Willbold, D., Rosch, P., and Sticht, H. (1998) *J.Biomol. Struct. Dyn.* 16, 683–692.
49. Tao, J., Frankel, A. D. (1992) *Proc. Natl Acad. Sci. USA* 89, 2723–2727.
50. Wallis, M. G., Streicher, B., Wank, H., von Ahsen, U., Clodi, E., Wallace, S. T., Famulok, M., and Schroeder, R. (1997) *Chem Biol* 4, 357–366.
51. Wang, S., Huber, P. W., Cui, M., Czarnik, A. W., Mei, H. Y. (1998) *Biochemistry* 37, 5549–5557.
52. Wei, P., Garber, M. E., Fang, S.-M., Fischer, W. H., and Jones, K. A. (1998) *Cell* 92, 451–462.
53. Weiss, J. M., Nath A., Major, E. O., and Berman, J. W. (1999) *J. Immunol.* 163, 2953–2959.
54. Wells, S. and Johnson, I. in *Tree-Dimentional Confocal Microscopy: Volume Investigation of Biological Specimens*, J. K. Stevens, L. R. Mills and J. E. Trogadis. Eds. Academic Press, (1994) pp. 101–129.
55. Wu-Baer, F., Lane, W. S., Gaynor, R. B. (1995) *Genes Dev.* 5, 2128–2140.
56. Yoshimura, J., Sekiya, T., Ogura, Y.(1974) *Bull. Chem. Soc. Japan.* 47, 1219–1233.
57. Zapp, M. L., Stern, S., Green, M. R. (1993) *Cell,* 74, 969–980.

Scheme 1.
Synthesis of the monosaccharide compounds.

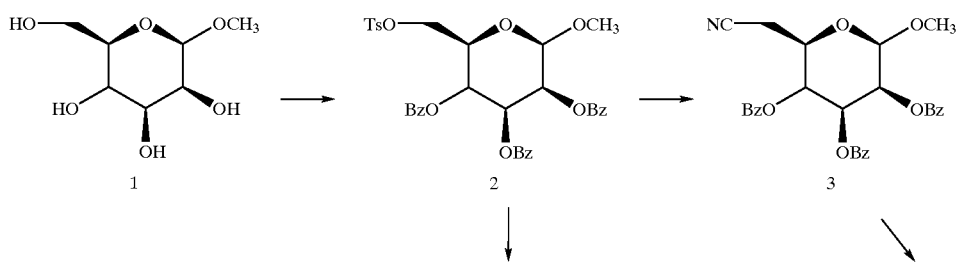

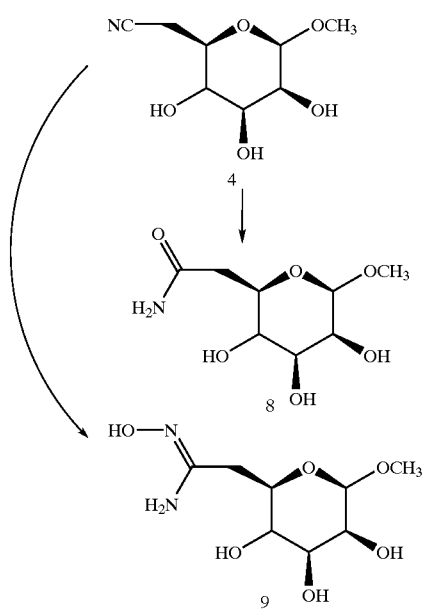
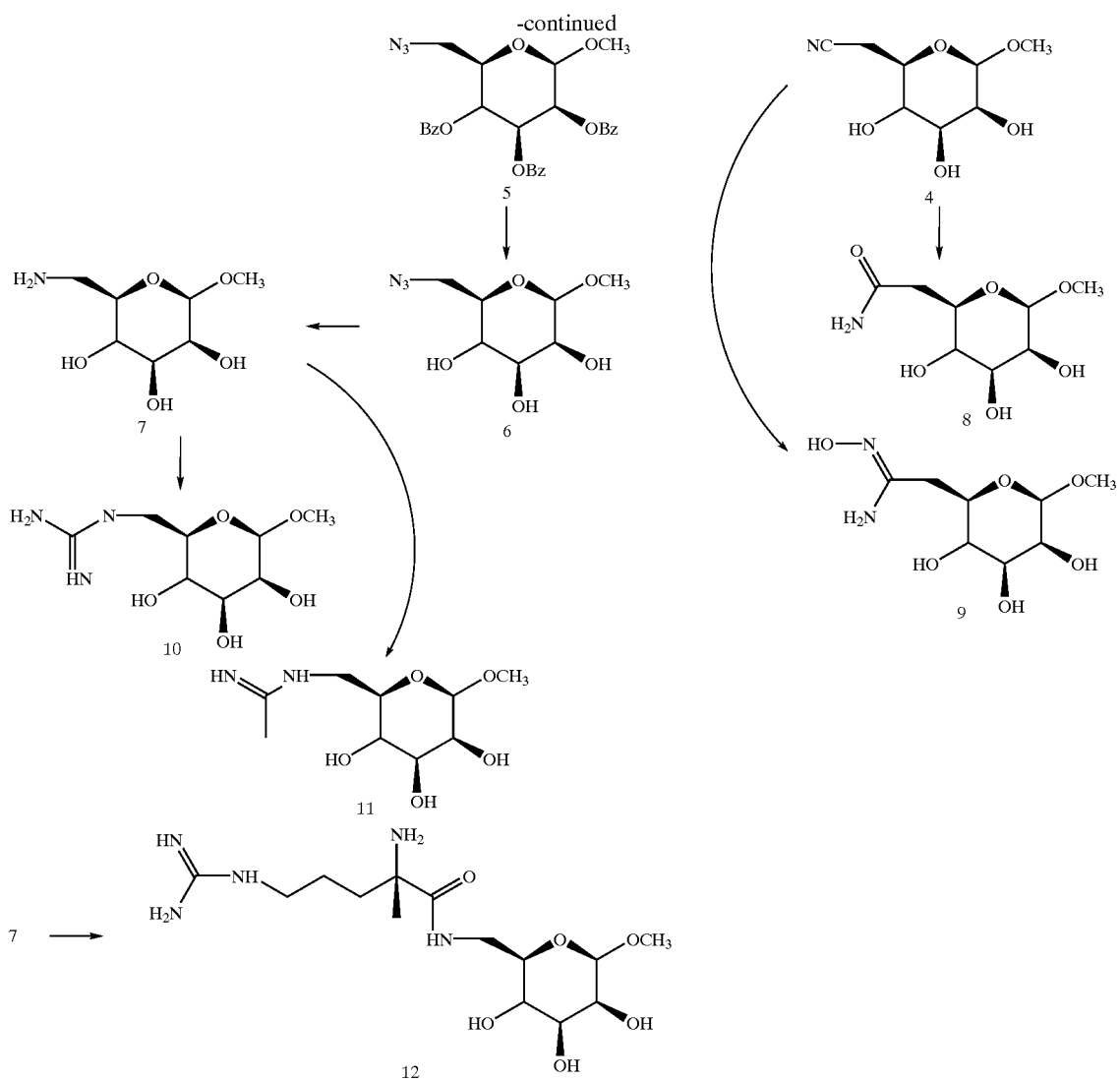
Scheme 2.
Kanamycin conjugates.
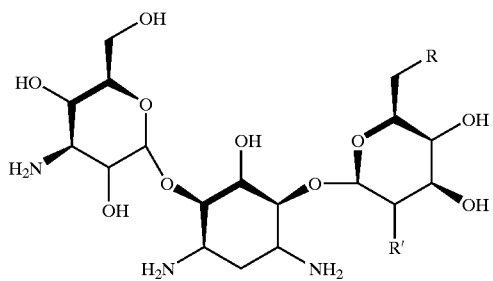
|   | A | B | C |
|---|---|---|---|
| R | NH₂ | NH₂ | OH |
| R' | OH | NH₂ | NH₂ |
Kanamycin isomers
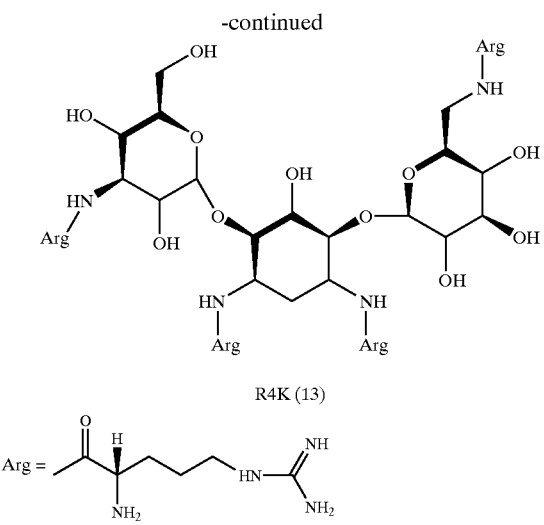

Scheme 3.
Gentamicin C conjugates.
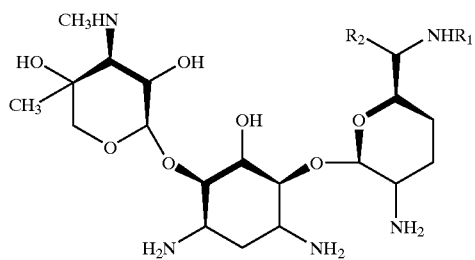
C$_1$: R$_1$ = R$_2$ = CH$_3$
C$_2$: R$_1$ = H  R$_2$ = CH$_3$
C$_{1a}$: R$_1$ = R$_2$ = H
Gentamicin C (Garamycin) isomers
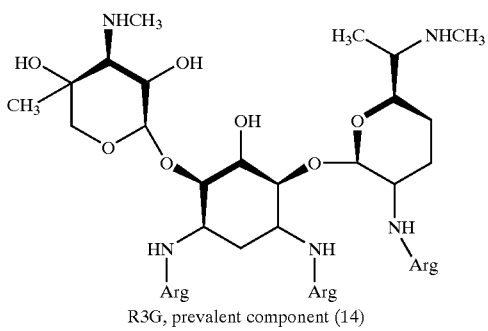
R3G, prevalent component (14)
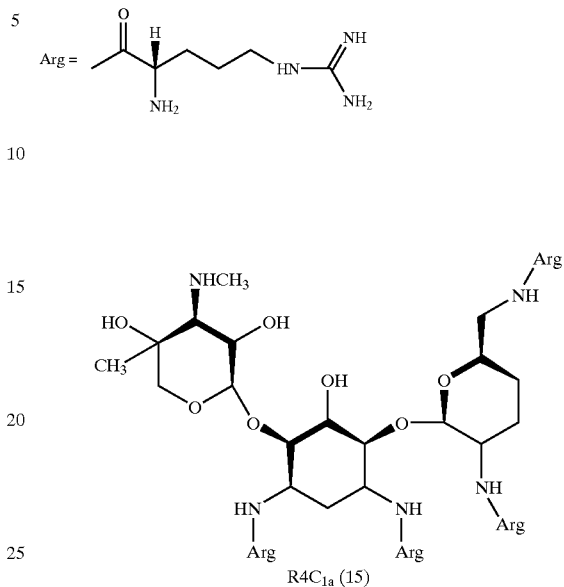
R4C$_{1a}$ (15)
Scheme 4.
Preparation of neomycin B conjugates.
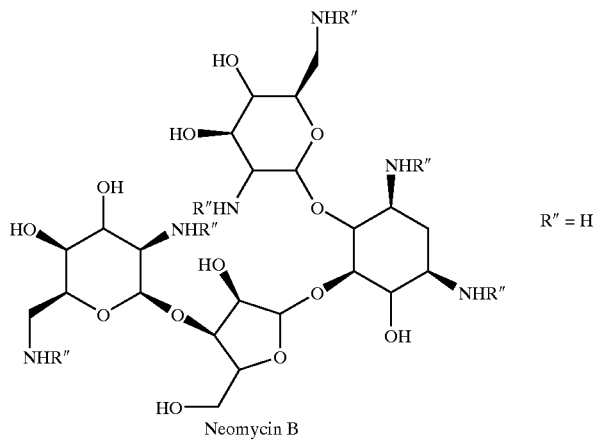
Neomycin B
R″ = H
1) a) Y = H, with DCC
   or
   b) Y = N-succinimidyl
2) atm, H$_2$, Pd/C Neomycin B - γ amino butyric acid conjugate
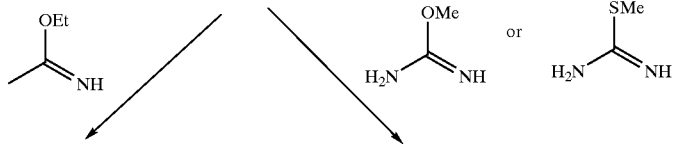
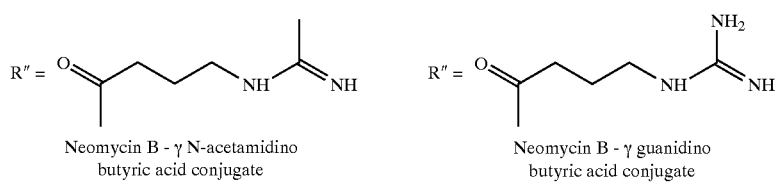
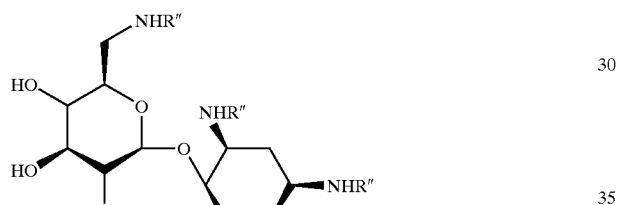
Neomycin B - γ N-acetamidino butyric acid conjugate
Neomycin B - γ guanidino butyric acid conjugate
Scheme 4a.
Preparation of argininamido-neomycin B conjugate
(NeoR, compound 20).
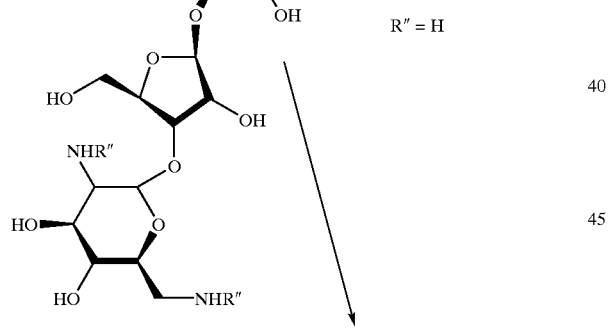
R″ = H
Argininamido-neomycin B conjugate
NeoR
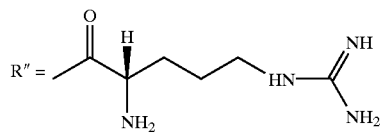

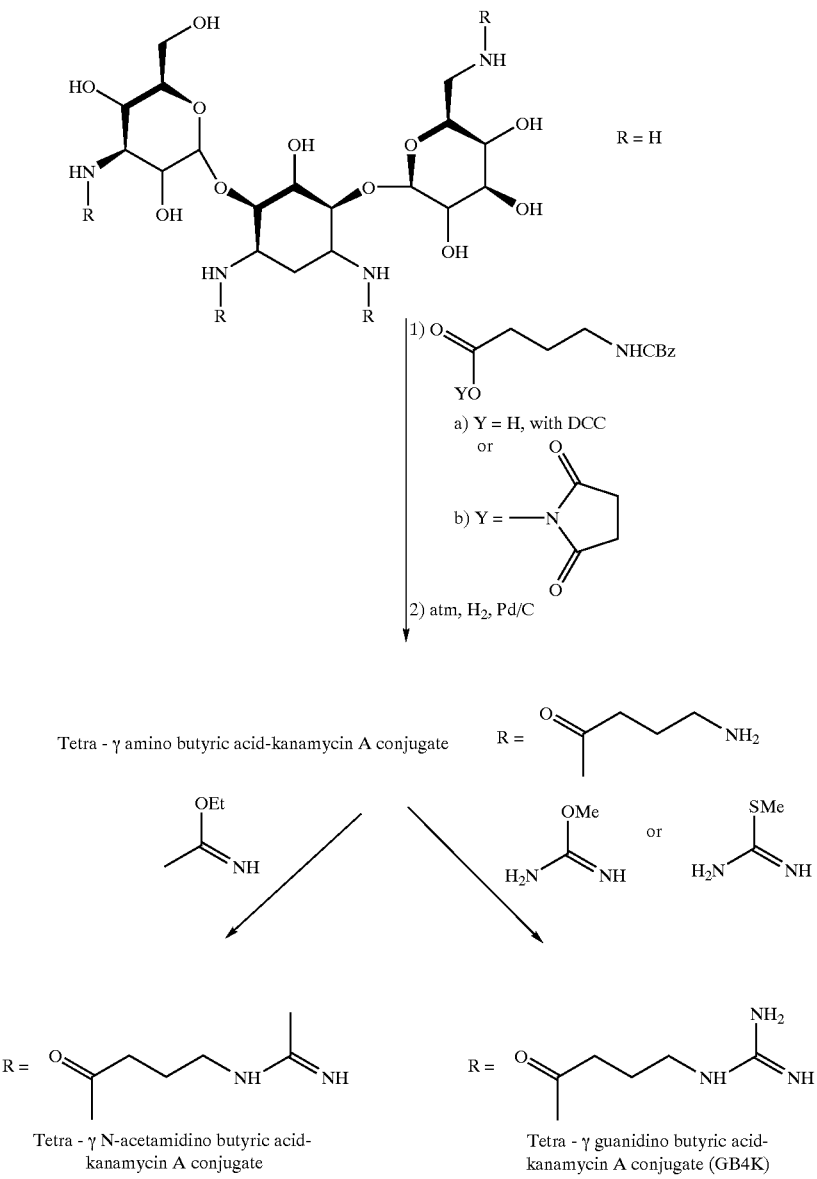

Scheme 5.
Preparation of kanamycin A conjugates.

What is claimed is:

1. A conjugate of the formula:

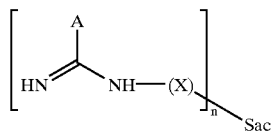

wherein

A is $CH_3$ or $NH_2$; X is a linear or branched $C_1$–$C_8$ alkyl chain optionally containing hydroxy, amino and/or oxo groups; n is an integer from 1 to 6, and Sac is the residue of a mono- or oligo-saccharide, provided that when A is $NH_2$ and X is —$(CH_2)_3$—CH$(NH_2)$—C(=O)—, the monosaccharide residue is not substituted at the position 1, and n is an integer from 2 to 6 when Sac is the residue of an oligosaccharide.

2. A conjugate according to claim 1, wherein A is $CH_3$.

3. A conjugate according to claim 2, wherein Sac is the residue of a monosaccharide.

4. A conjugate according to claim 2, wherein Sac is the residue of an oligosaccharide.

5. A pharmaceutical composition comprising a therapeutically effective amount of a compound according to claim 1, and a pharmaceutically acceptable carrier.

6. An antiviral pharmaceutical composition according to claim 5 in unit dosage form wherein said therapeutically effective amount is an antiviral-effective amount.

7. An antiretroviral pharmaceutical composition according to claim 6, wherein said antiviral effective amount is an antiretroviral effective amount.

8. Methyl 6-deoxy-6-(N-acetamidino)-α-D-mannopyranoside.

9. A conjugate of the formula:

$$\left[ \underset{HN}{\overset{A}{\|}} C - NH - (X)_n \right] Sac$$

wherein

A is $CH_3$, X is a linear or branched $C_1$–$C_8$ alkyl chain optionally containing hydroxy, amino and/or oxo groups; n is an integer from 2 to 6, and Sac is the residue of an aminoglycoside antibiotic.

10. A conjugate according to claim 9, wherein the aminoglycoside antibiotic is neomycin, kanamycin or gentamicin.

11. A conjugate according to claim 10, selected from the group consisting of the conjugates γ-(N-acetamidino)butyric acid-neomycin B and tetra-γ-(N-acetamidino)butyric acid - kanamycin A.

12. A conjugate of the formula:

$$\left[ \underset{HN}{\overset{A}{\|}} C - NH - (X)_n \right] Sac$$

wherein

A is $NH_2$, X is a linear or branched $C_1$–$C_8$ alkyl chain optionally containing hydroxy, amino and/or oxo groups; n is an integer from 1 to 6, and Sac is the residue of a mono- or oligo-saccharide, provided that when X is —$(CH_2)_3$—$CH(NH_2)$—$C(=O)$—, the monosaccharide residue is not substituted at the position 1, and when Sac is the residue of an oligosaccharide, n is an integer from 2 to 6.

13. A conjugate according to claim 12, wherein Sac is the residue of a monosaccharide.

14. A conjugate according to claim 13 selected from the group consisting of the conjugates methyl 6-deoxy-6-guanidino-α-D-mannopyranoside and methyl 6-deoxy-6-(N-L-argininamido)-α-D-mannopyranoside.

15. A conjugate according to claim 12, wherein Sac is the residue of an oligosaccharide.

16. A conjugate according to claim 15, wherein Sac is the residue of an aminoglycoside antibiotic.

17. A conjugate according to claim 16, wherein the aminoglycoside antibiotic is neomycin, kanamycin or gentamicin.

18. The tetraargininamido-kanamycin A conjugate according to claim 17, of the formula:

[structure shown]

19. The triargininamido-gentamicin C conjugate according to claim 17, of the formula:

[structure shown]

20. The tetraargininamido-gentamicin C conjugate according to claim 17, of the formula:

[structure shown]

21. The hexa-argininamido-neomycin B conjugate according to claim 17, of the formula:

[structure shown]

22. The γ-(N-guanidino)butyric acid-neomycin B conjugate according to claim 17, of the formula:
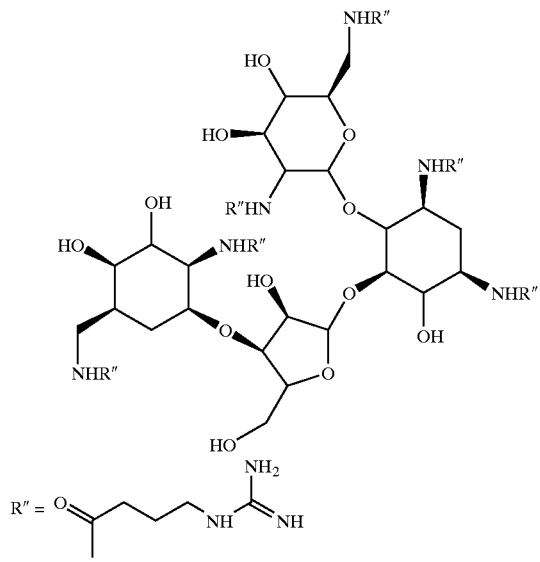
23. The tetra-γ-(N-guanidino)butyric acid-kanamycin A conjugate according to claim 17, of the formula:
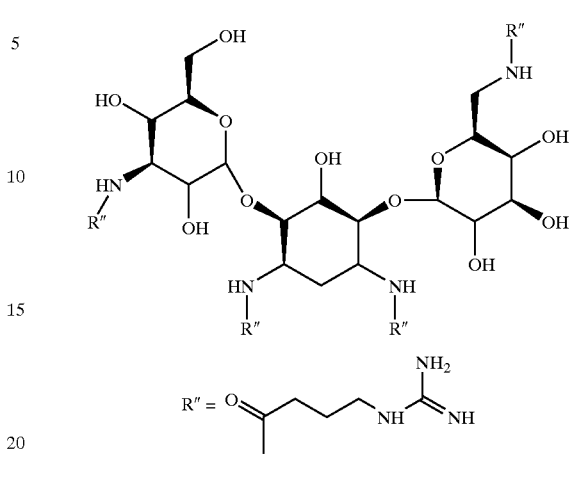
* * * * *